US009192508B2

(12) United States Patent
Boucher et al.

(10) Patent No.: US 9,192,508 B2
(45) Date of Patent: Nov. 24, 2015

(54) APPARATUS, SYSTEMS, AND METHODS FOR CONSTRAINING AND/OR SUPPORTING TISSUE STRUCTURES ALONG AN AIRWAY

(75) Inventors: Ryan P. Boucher, San Francisco, CA (US); Winfried Hohenhorst, Essen (DE); Eric N. Doelling, Sunnyvale, CA (US)

(73) Assignee: SileoMed, Inc., Santa Clara, CA (US)

( * ) Notice: Subject to any disclaimer, the term of this patent is extended or adjusted under 35 U.S.C. 154(b) by 1083 days.

(21) Appl. No.: 12/928,091

(22) Filed: Dec. 3, 2010

(65) Prior Publication Data

US 2011/0155142 A1 Jun. 30, 2011

Related U.S. Application Data

(63) Continuation-in-part of application No. 12/653,078, filed on Dec. 7, 2009, now Pat. No. 8,695,607.

(60) Provisional application No. 61/201,256, filed on Dec. 9, 2008, provisional application No. 61/276,222, filed on Sep. 9, 2009, provisional application No. 61/404,495, filed on Oct. 4, 2010.

(51) Int. Cl.
*A61F 5/56* (2006.01)
*A61F 2/02* (2006.01)
*A61F 2/08* (2006.01)
*A61B 17/00* (2006.01)
*A61M 16/06* (2006.01)

(52) U.S. Cl.
CPC . *A61F 5/566* (2013.01); *A61F 5/56* (2013.01); *A61B 2017/00814* (2013.01); *A61F 2/02* (2013.01); *A61F 2/08* (2013.01); *A61M 16/06* (2013.01)

(58) Field of Classification Search
CPC ............. A61F 5/56; A61F 5/566; A61F 2/02; A61F 2/08; A61B 2017/00814
USPC .................... 128/848; 433/140; 623/9, 23.72; 606/53, 54, 60
See application file for complete search history.

(56) References Cited

U.S. PATENT DOCUMENTS

| 2008/0053461 A1* | 3/2008 | Hirotsuka et al. ............ 128/848 |
| 2008/0066766 A1 | 3/2008 | Paraschac et al. |
| 2008/0078412 A1 | 4/2008 | Buscemi et al. |
| 2011/0155142 A1 | 6/2011 | Boucher et al. |

FOREIGN PATENT DOCUMENTS

WO  WO 2010/068251 A1  6/2010

OTHER PUBLICATIONS

International Search Report and Written Opinion dated Jan. 17, 2012 in International Patent Application Serial No. PCT/US2011/054750.

* cited by examiner

*Primary Examiner* — Alireza Nia
*Assistant Examiner* — Keri J Nelson
(74) *Attorney, Agent, or Firm* — Ryan Kromholz & Manion, S.C.

(57) ABSTRACT

Systems and methods implant structures in, on, or near the floor of the mouth. The structures can be sized and configured to resist buckling of tissue structures in, on, or near the floor of the mouth in a cranial direction. The systems and methods can also be sized and configured, singly or in combination, for stabilizing a hyoid bone, and/or stabilizing a tongue, and/or suspending a tongue, and/or providing neuro-muscular stimulation of tissue structures in, on, or near the floor of the mouth.

14 Claims, 44 Drawing Sheets

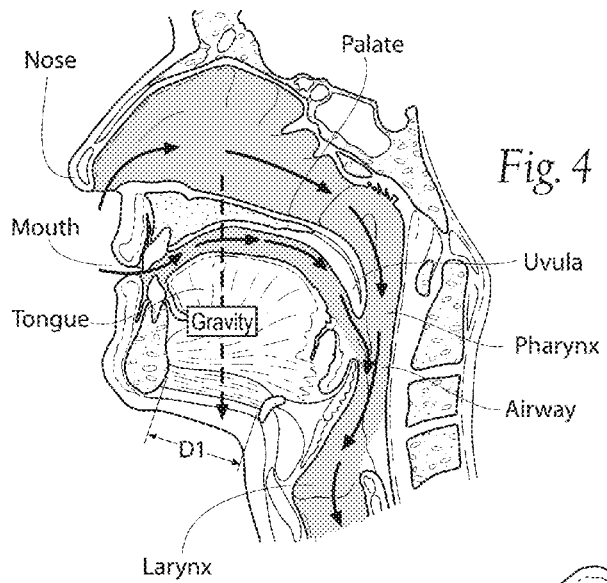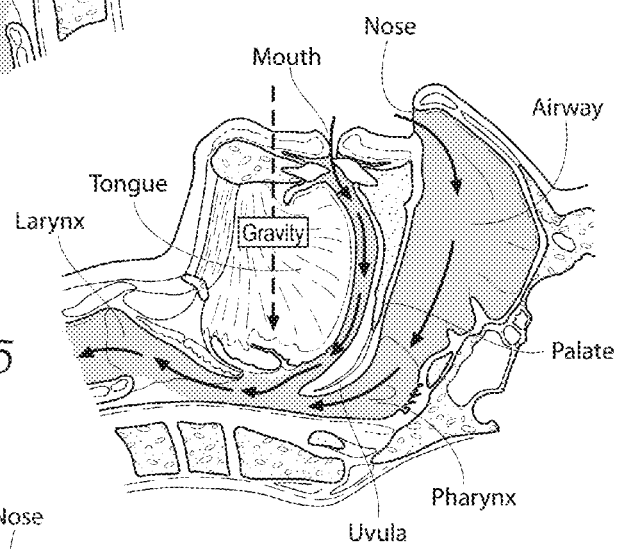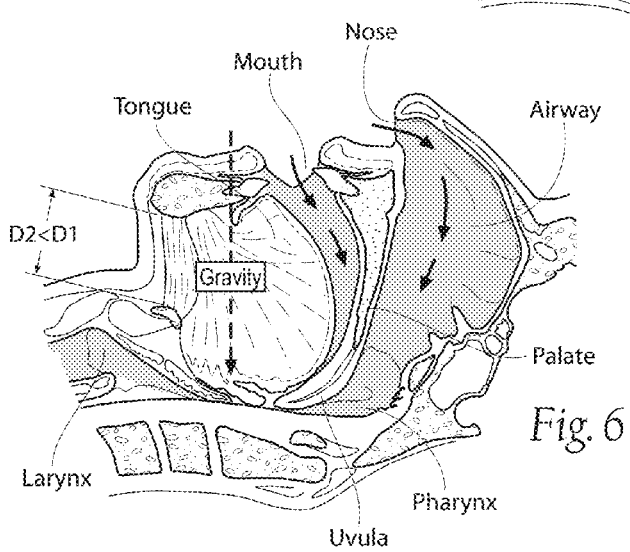

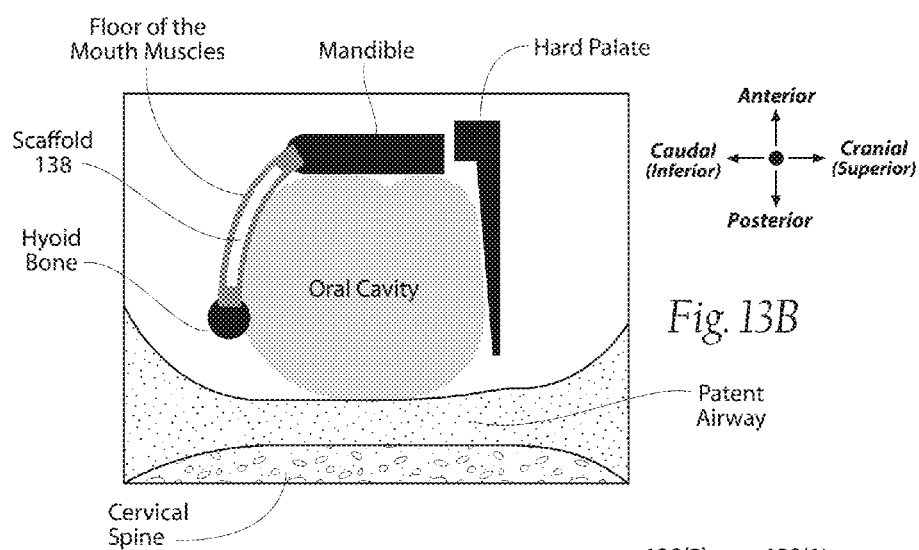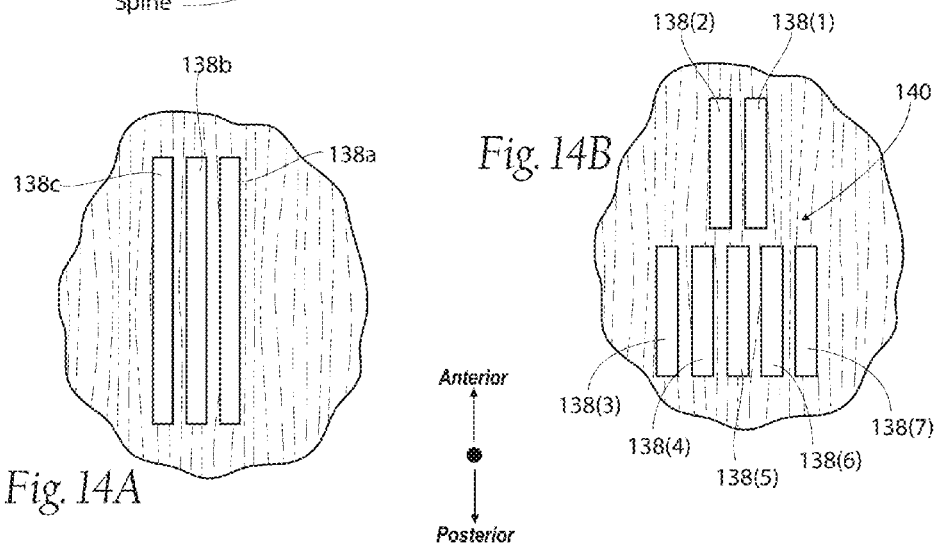

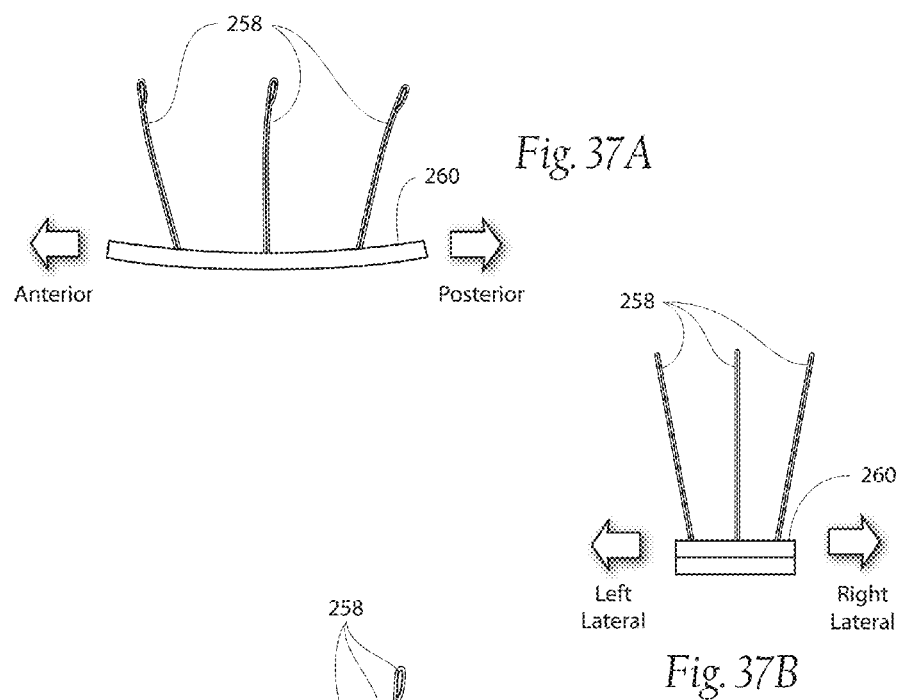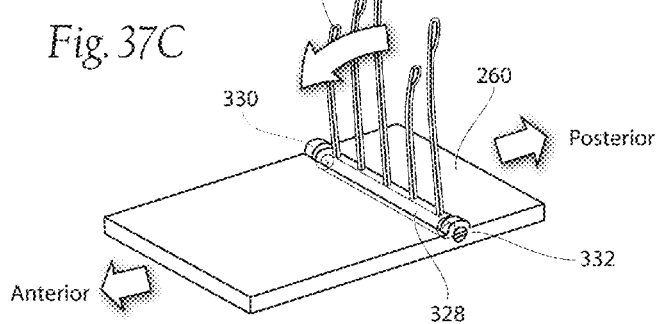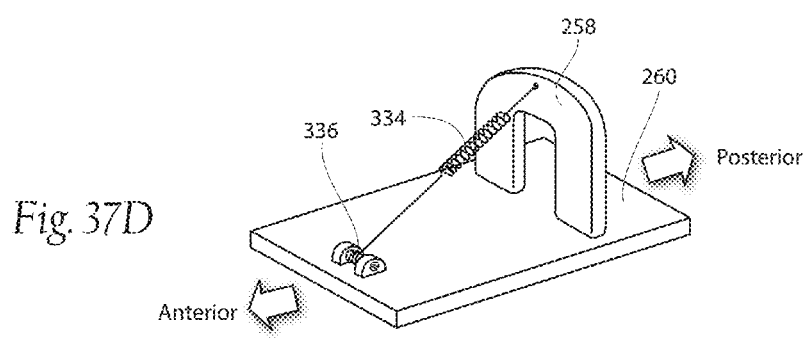

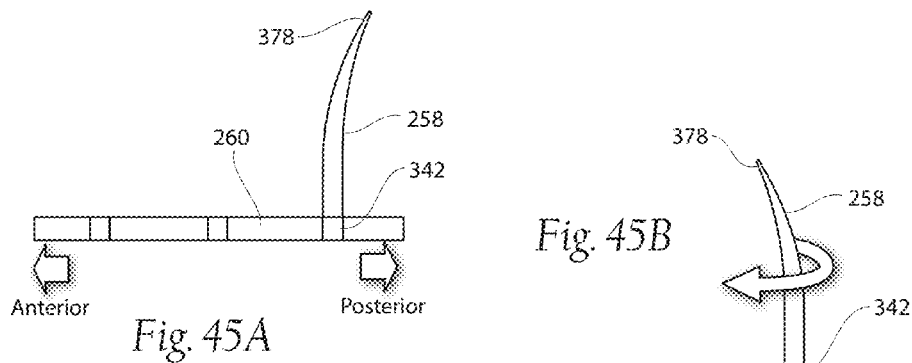
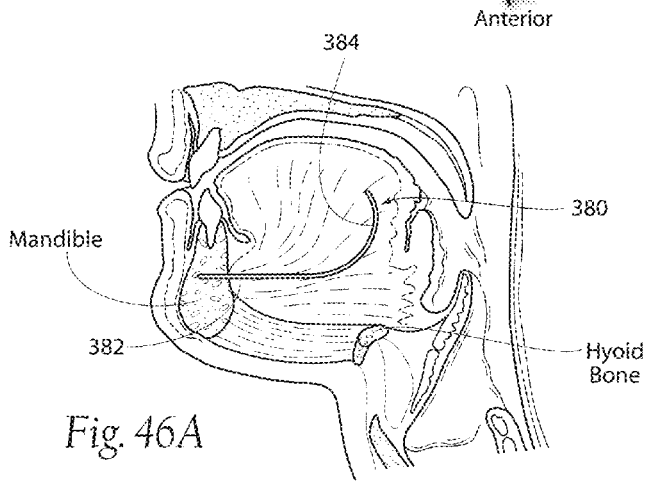
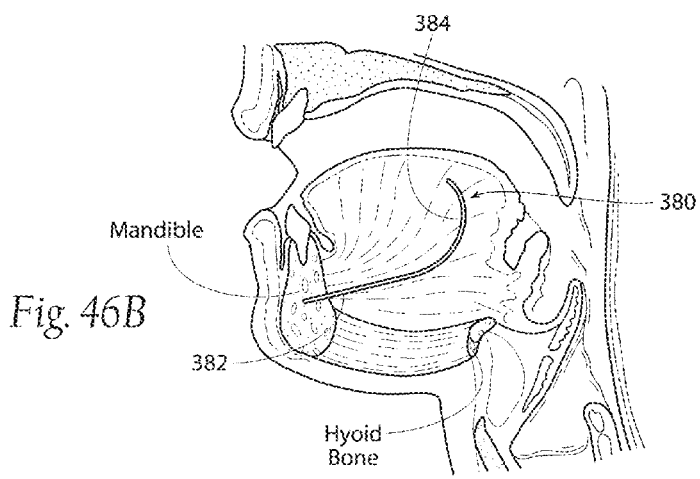

APPARATUS, SYSTEMS, AND METHODS FOR CONSTRAINING AND/OR SUPPORTING TISSUE STRUCTURES ALONG AN AIRWAY

RELATED APPLICATIONS

This application is a continuation-in-part of co-pending U.S. patent application Ser. No. 12/653,078, filed 7 Dec. 2009 and entitled "Apparatus, Systems, and Methods for Constraining and/or Supporting Tissue Structures Along an Airway," which claims the benefit of U.S. Provisional Patent Application Ser. No. 61/201,256 filed 9 Dec. 2008, and U.S. Provisional Patent Application Ser. No. 61/276,222 filed 9 Sep. 2009, which are incorporated herein by reference. This application also claims the benefit of U.S. Provisional Patent Application Ser. No. 61/404,495, filed 4 Oct. 2010.

BACKGROUND OF THE INVENTION

The Greek word "apnea" literally means "without breath." People with untreated sleep apnea stop breathing repeatedly during their sleep, sometimes hundreds of times during the night and often for a minute or longer.

Obstructive sleep apnea (OSA) is the most common category of sleep-disordered breathing. The muscle tone of the body ordinarily relaxes during sleep. At the level of the throat, the human airway is composed of collapsible walls of soft tissue which can obstruct breathing during sleep. Mild, occasional sleep apnea, such as many people experience during an upper respiratory infection may not be important, but chronic, severe obstructive sleep apnea requires treatment to prevent sleep deprivation and other complications.

Individuals with low muscle tone and abundant soft tissue around the airway (e.g., due to obesity), and/or structural features that give rise to a narrowed airway are at high risk for obstructive sleep apnea. The elderly are more likely to have OSA than young people. Men are more typical sleep apnea sufferers than women and children, although it is not uncommon in the latter two.

Common symptoms include loud snoring, restless sleep, and sleepiness during the daytime. Diagnostic tests include home oximetry or polysomnography in a sleep clinic.

Sleep apnea is very common, as common as adult diabetes, and affects more than twelve million Americans, according to the National Institutes of Health. Untreated, sleep apnea can cause high blood pressure and other cardiovascular disease, memory problems, weight gain, impotency, and headaches. Moreover, untreated sleep apnea may be responsible for job impairment and motor vehicle crashes.

Some treatments involve lifestyle changes, such as avoiding alcohol or muscle relaxants, losing weight, and quitting smoking. Many people benefit from sleeping at a 30 degree elevation of the upper body or higher, as if in a recliner. Doing so helps prevent the gravitational collapse of the airway. Lateral positions (sleeping on a side), as opposed to supine positions (sleeping on the back), are also recommended as a treatment for sleep apnea, largely because the gravitational component is smaller in the lateral position. Some people benefit from various kinds of oral appliances to keep the airway open during sleep. There are also surgical procedures to remove and tighten tissue and widen the airway, but these tend to be very intrusive. "Breathing machines" like continuous positive airway pressure (CPAP) may help.

The CPAP machine delivers a stream of compressed air via a hose to a nasal pillow, nose mask or full-face mask, splinting the airway (keeping it open under air pressure) so that unobstructed breathing becomes possible, reducing and/or preventing apneas and hypopneas. This has the additional benefit of reducing or eliminating the extremely loud snoring that sometimes accompanies sleep apnea. Prospective CPAP candidates are often reluctant to use this therapy, since the nose mask and hose to the machine look uncomfortable and clumsy, and the airflow required for some patients can be vigorous. Some patients will develop nasal congestion while others may experience rhinitis or a runny nose. Other conditions that can accompany the use of CPAP include flatulence caused by swallowing too much air; irritation of the skin due to wearing a CPAP mask; upper airway infection; red eye and tear flow; anxiety and feelings of suffocation and/or claustrophobia; and the need to cart around CPAP equipment during travel. Compliance requires self-discipline and resolve. Some patients adjust to the treatment within a few weeks, others struggle for longer periods, and many discontinue treatment entirely.

SUMMARY OF THE INVENTION

The invention provides apparatus, systems, and methods for constraining and/or supporting tissue structures along an airway.

One aspect of the invention provides a scaffold structure sized and configured to be implanted in, on, or near the floor of the mouth to resist buckling of the tissue structures in, on, or near the floor of the mouth in a cranial direction. In one embodiment, the scaffold structure is sized and configured when implanted in, on, or near the floor of the mouth, to preferentially bend in a caudal direction. In one embodiment, the scaffold structure is shaped to possess, when implanted in, on, or near the floor of the mouth, a convex orientation facing the feet.

The scaffold structure can be sized and configured, when implanted in, on, or near the floor of the mouth, to extend longitudinally in an anterior-to-posterior direction, and/or to extend longitudinally in a lateral direction, or combination thereof.

The scaffold structure can include a polymer, or metal, or fiber material, or combinations thereof. The scaffold structure can comprise a trampoline-shaped structure or a formed spring structure. The scaffold structure can include at least one leaf-spring region for anchoring to structures in the oral cavity.

In one embodiment, the scaffold structure includes at least one component that is selectively activated to reshape, and/or stiffen, and/or move the scaffold structure to resist buckling of tissue structures in, on, or near the floor of the mouth in a cranial direction. The component can comprise, e.g., a magnetically actuated material.

In one embodiment, the system further includes a second component sized and configured to stabilize at least one of a hyoid bone and/or a tongue, or to suspend a tongue.

For example, in one embodiment, one or more struts extend from the scaffold structure in a superior direction into a tongue.

In one embodiment, the system further includes a second component sized and configured to provide neuro-muscular stimulation of tissue structures in, on, or near the floor of the mouth.

Another aspect of the invention provides a tongue stabilization system comprising one or more struts that extend from a location in, on, or near the floor of the mouth in a superior direction into a tongue.

The struts can be arranged in an anterior-to-posterior array or a lateral array or a combination thereof. In one embodiment, at least one of the struts includes a biasing force applied to bias the strut in an anterior direction to resist posterior movement of the tongue. In one embodiment, the biasing force is adjustable.

In one embodiment, the system further includes a mount implanted in, on, or near the floor of the mouth, and the at least one strut is coupled to the mount. The mount can include a mounting aperture to receive a strut to couple the strut to the mount. The mounting aperture can be sized and configured to hold the strut in a desired orientation, or in an adjustable range of orientations.

In one embodiment, a spring is coupled to the strut and coupled to the mount anterior to the strut.

In one embodiment, a spring is coupled to the strut and coupled to a tissue structure in the oral cavity anterior to the strut.

Another aspect of the invention provides a method comprising implanting a scaffold structure in, on, or near the floor of the mouth to resist buckling of the tissue structures in, on, or near the floor of the mouth in a cranial direction.

In one embodiment, the method further includes, in conjunction with the scaffold structure, stabilizing a hyoid bone, and/or stabilizing a tongue, and/or suspending a tongue, and/or providing neuro-muscular stimulation of tissue structures in, on, or near the floor of the mouth.

Another aspect of the invention provides a method comprising implanting a structure in, on, or near the floor of the mouth to provide neuro-muscular stimulation of tissue structures in, on, or near the floor of the mouth.

Another aspect of the invention provides a method comprising implanting a structure in, on, or near the floor of the mouth to provide hyoid bone stabilization.

Another aspect of the invention provides a method comprising implanting a structure in, on, or near the floor of the mouth to provide tongue stablization.

Another aspect of the invention provides a method comprising implanting a structure in, on, or near the floor of the mouth to provide tongue suspension.

BRIEF DESCRIPTION OF THE DRAWINGS

FIG. 4 is an anatomic side section view of an oral cavity, pharynx, and larynx of an adult human, standing with the mouth closed, annotated to show the passage of air through a normal, unobstructed airway when the person is upright and active.

FIG. 5 is an anatomic side section view of an oral cavity, pharynx, and larynx of an adult human, in a supine sleep position with the mouth closed, annotated to show the passage of air through the airway when the person is asleep, and also showing the effects of gravity on tissue structures along the airway that can narrow the airway during sleep.

FIG. 6 is an anatomic side section view of an oral cavity, pharynx, and larynx of an adult human, in a supine sleep position with the mouth opened, showing the effects of gravity and an opened mouth on tissue structures along the airway, being annotated to show the collapse of certain tissue structures into the airway and the resultant obstruction of airflow.

FIG. 13B is a diagrammatic side view of an oral cavity and an airway, like that shown in FIGS. 1C and 1D, showing how the presence of a scaffold as shown in FIG. 13A affects airway patency.

FIG. 14A/B/C/D are plane views of scaffold structures like that shown in FIGS. 12A/B/C/D implanted in arrays in, on, or near tissue structures in the floor of the mouth.

FIGS. 37A and 37B are lateral side and edge views of systems comprising arrays of one or more anterior-to-posterior and laterally placed struts, like that shown in FIG. 35B, showing how the angular orientation of the struts can be varied to achieve the desired therapeutic objectives.

FIGS. 37C, 37D, and 37E are perspective and side views of systems comprising one or more struts that extend in a superior direction into the tongue to provide tongue stabilization, and that are biased by springs to resist posterior movement of the tongue.

FIGS. 45A and 45B are side views of a curved strut that can be rotated into a desired angular orientation.

FIGS. 46A and 46B are anatomic view of an oral cavity, pharynx, and larynx of an adult human, with the mouth, respectively, closed and opened, showing a representative embodiment of a flexible tongue lever system.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Pertinent Anatomy

A. The Oral Cavity or Mouth

Figure 1A:
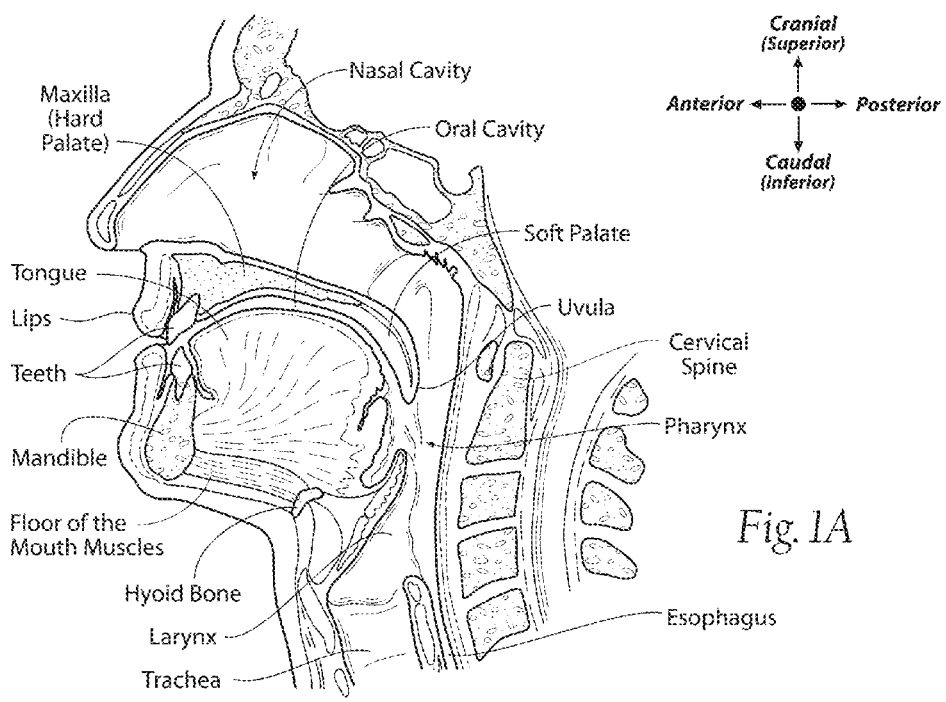
FIG. 1A is an anatomic side section view of an oral cavity, pharynx, and larynx of an adult human, with the mouth closed.

FIG. 1A is an anatomic view (in section) of an oral cavity in the head of an adult human. In human anatomy, the oral cavity—which will also be called the mouth—constitutes the orifice through which food and air enter the body.

Figure 2A:
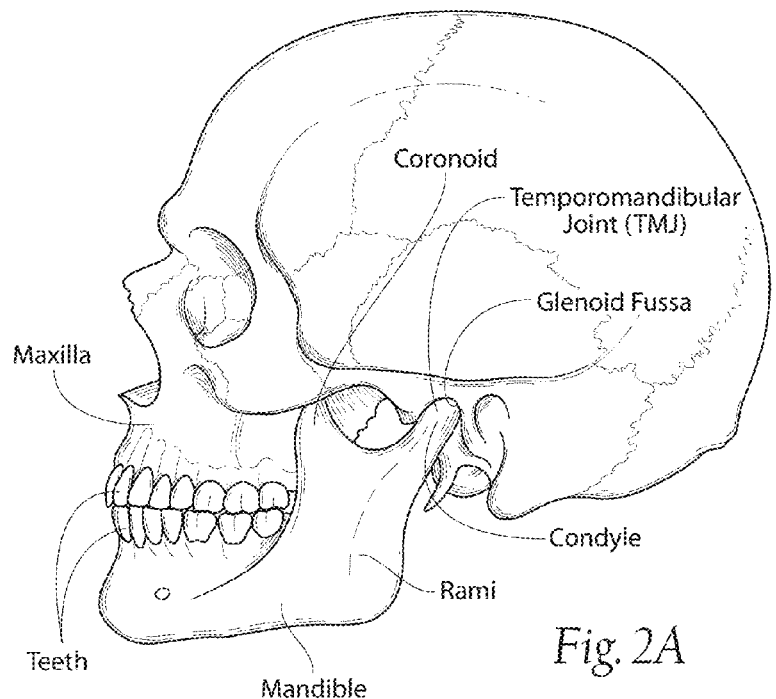
FIG. 2A is an anatomic side elevation view of a human skull, with the jaws closed.
Figure 2B:
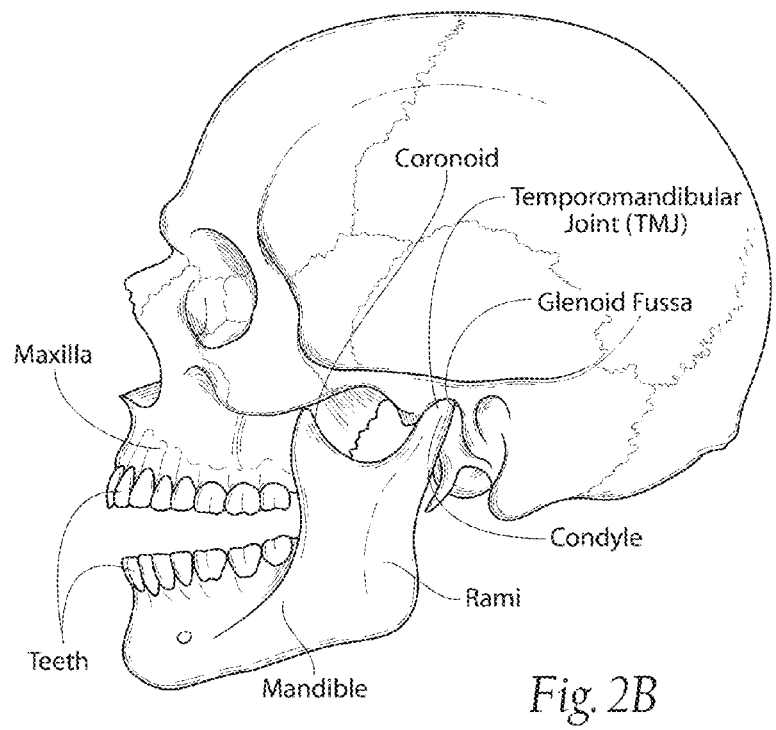
FIG. 2B is an anatomic side elevation view of a human skull, with the jaws opened.

As further delineated in FIGS. 2A and 2B, a pair of bones, called the jaws, form the skeletal framework of the mouth. The jaws contain teeth and include a movable lower jaw (the mandible) and a fixed upper jaw. The jaws function by moving in opposition to each other (as FIGS. 1A/B and 2A/B show) and are used for biting, chewing, and the handling of food.

Figure 1B:
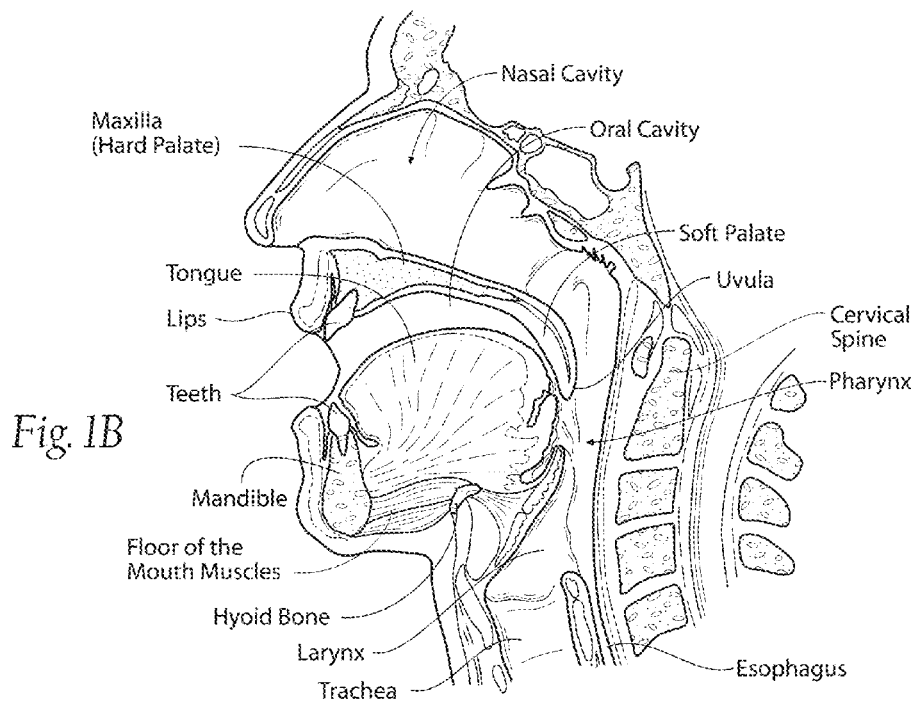
FIG. 1B is an anatomic side section view of an oral cavity, pharynx, and larynx of an adult human, with the mouth opened.

Referring back to FIGS. 1A and 1B, the interior boundaries of the oral cavity are defined by the lips, the cheeks (not shown), the hard and soft palates, and the throat or pharynx. The oral cavity or mouth opens to the outside at the lips (which will also be called the front or anterior region of the oral cavity). Lowering of the mandible relative to the maxilla opens the mouth, as FIG. 1B shows. The oral cavity empties into the pharynx (which will also be called the back or posterior region of the oral cavity).

FIG. 1A illustrated the nomenclature that will be used to depict direction. Anterior and posterior mean front and back, respectively, as just described. Superior or cranial and inferior or caudal mean up and down, respectively.

As FIGS. 1A and 1B show, the pharynx is a cone-shaped passageway leading from the oral cavity (and nasal cavity) to the esophagus and larynx. The esophagus leads to the stomach. It is the path through which food entering the oral cavity is carried into the stomach for digestion in the digestive system. The larynx is a hollow, tubular structure connected to the top of the windpipe (trachea). Air entering the oral cavity passes through the larynx on its way to the lungs. The larynx also produces vocal sounds, and for this reason is also called the voice box. The larynx also prevents the passage of food and other foreign particles into the lower respiratory tracts.

The chief structures of the mouth are the teeth, palate, and tongue. The teeth, carried by the articulating jaws, tear and grind ingested food into small pieces that are suitable for digestion. The palate separates the mouth from the nasal cavity, allowing separate passages for air and for food. The tongue is a large muscle firmly anchored to the floor of the mouth. The tongue positions and mixes food and also carries sensory receptors for taste. In addition to its primary role in the intake and initial digestion of food and the intake of air during breathing, the mouth and its structures are essential in humans to the formation of speech.

1. The Palate (The Roof of the Mouth)

The palate (see FIGS. 1A and 1B) constitutes the roof of the mouth. It separates the oral and nasal cavities. The palate consists of an anterior hard palate of bone and, in humans, a posterior soft palate that has no skeletal support and terminates in a fleshy, elongated projection called the uvula.

The hard palate composes two-thirds of the total palate area. The hard palate is a plate of bone covered by a moist, durable layer of mucous-membrane tissue, which secretes small amounts of mucus. This layer forms several ridges that help grip food while the tongue agitates it during chewing. The hard palate provides space for the tongue to move freely and supplies a rigid floor to the nasal cavity so that pressures within the mouth do not close off the nasal passage.

The soft palate is composed of muscle and connective tissue, which give it both mobility and support. This palate is very flexible. When elevated for swallowing and sucking, it completely blocks and separates the nasal cavity and nasal portion of the pharynx from the mouth and the oral part of the pharynx. While elevated, the soft palate creates a vacuum in the oral cavity, which keeps food out of the respiratory tract.

2. The Floor of the Mouth

The floor of the mouth (see FIG. 3A) is a tissue region that is bounded anteriorly by the mandible and posteriorly by the hyoid bone. The floor of the mouth is immediately surrounded by other tissue structures, such as muscles attached to the hyoid bone and/or mandible (as will be described later), which are mutually interconnected and mutually affected by the condition and orientation of tissue in the floor of the mouth. The floor of the mouth can be seen only when the tongue is raised. In the midline is a prominent fold (called the frenulum linguae), to which the tongue is anchored.

3. The Tongue

Figure 3A:
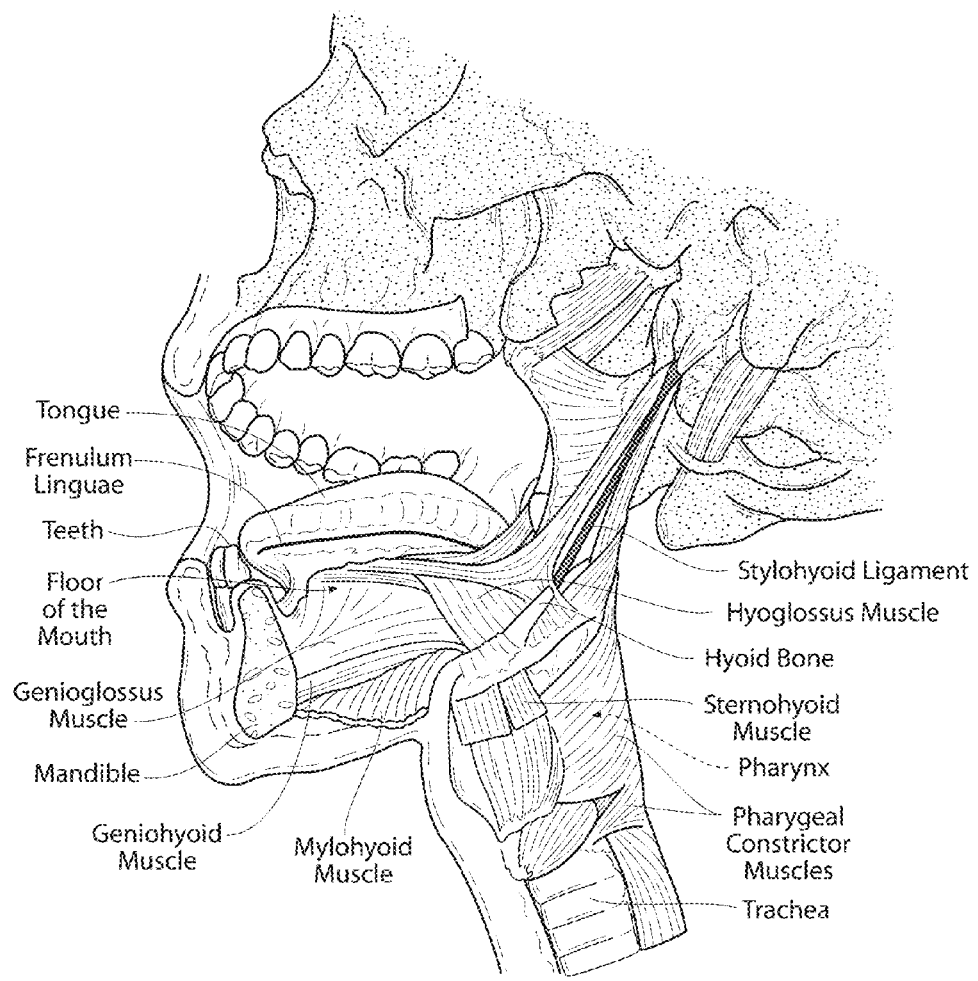
FIG. 3A is an anatomic lateral view of the oral cavity shown in FIG. 1B, with superficial and deep facial structures and left half of the mandible removed to show muscles of the tongue and pharynx, some of which have been cut for the purpose of illustration.

The tongue (shown enlarged in FIG. 3B, and which is also shown in FIGS. 1A and 1B and 3A) is a muscular organ located on the floor of the mouth. The tongue is a mobile muscular organ that can assume a variety of shapes and positions. The tongue rests partly in the oral cavity and partly in the pharynx (FIGS. 1A and 2B show).

The tongue is an extremely mobile structure in humans and an important accessory organ in such motor functions as speech, chewing, and swallowing. In conjunction with the cheeks, it is able to guide and maintain food between the upper and lower teeth until mastication is completed.

At rest, the tongue occupies essentially all of the oral cavity proper. The tongue is involved with mastication, taste, deglutition, and oral cleansing. Its two major functions are forming words during speaking and squeezing food into the pharynx when swallowing.

4. The Pharynx (Pharyngeal Airway)

Referring back to FIGS. 1A and 1B, the pharynx serves both respiratory and digestive functions. For the respiratory function, the pharynx serves as the essential airway for the body. Blockage of the airway of the pharynx can lead to a cessation of breathing and resultant disruption or interruption of the normal body functions.

Figure 3B:
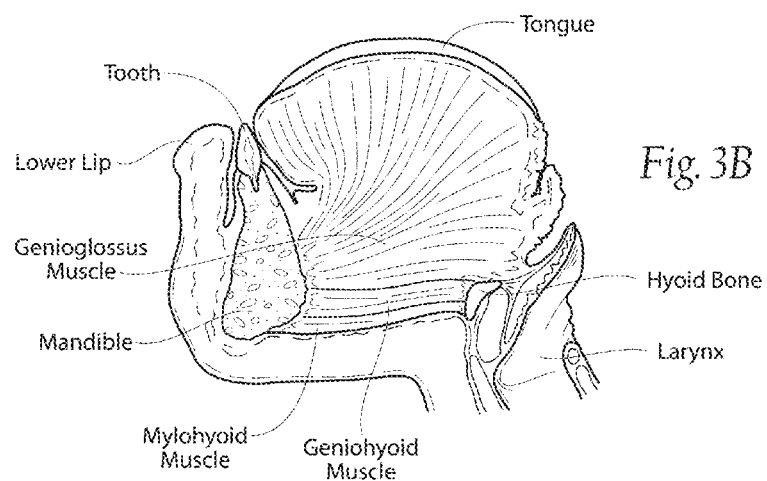
FIG. 3B is an anatomic side elevation view of the genioglossus and intrinsic muscles of the tongue.
Figure 3C:
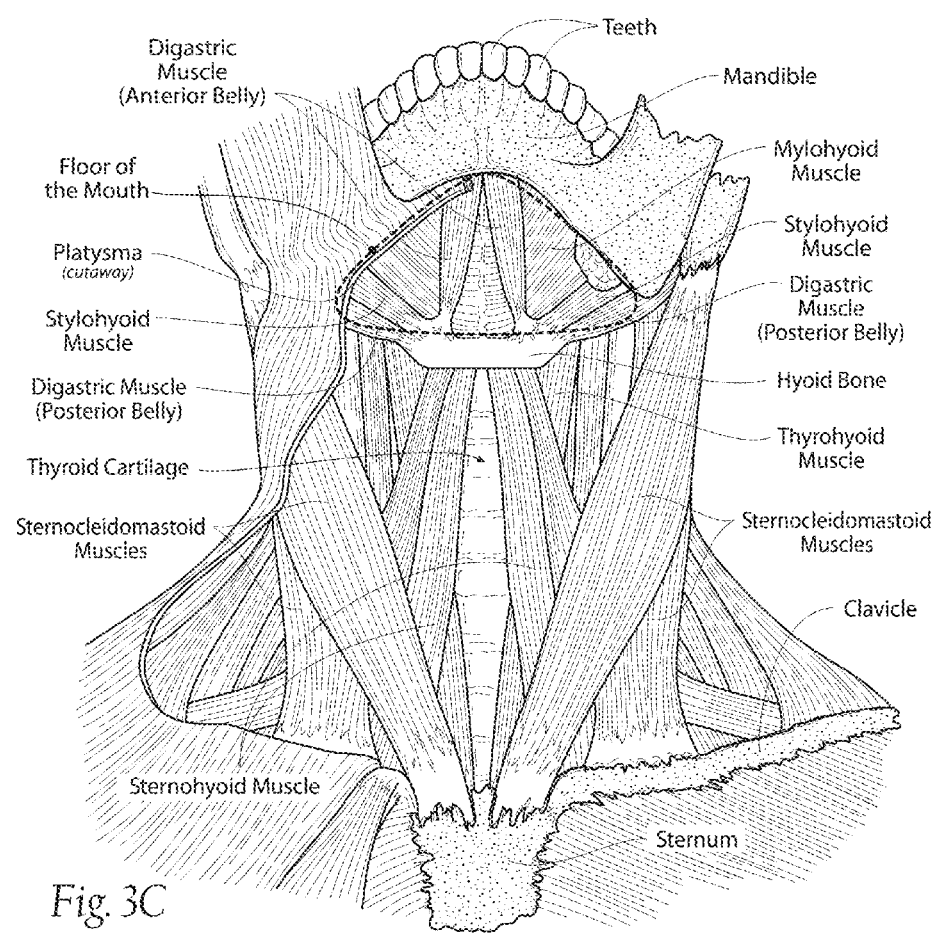
FIG. 3C is an anatomic anterior view of the major muscles of the neck, also showing the hyoid bone and the muscles connected to it.
Figure 3D:
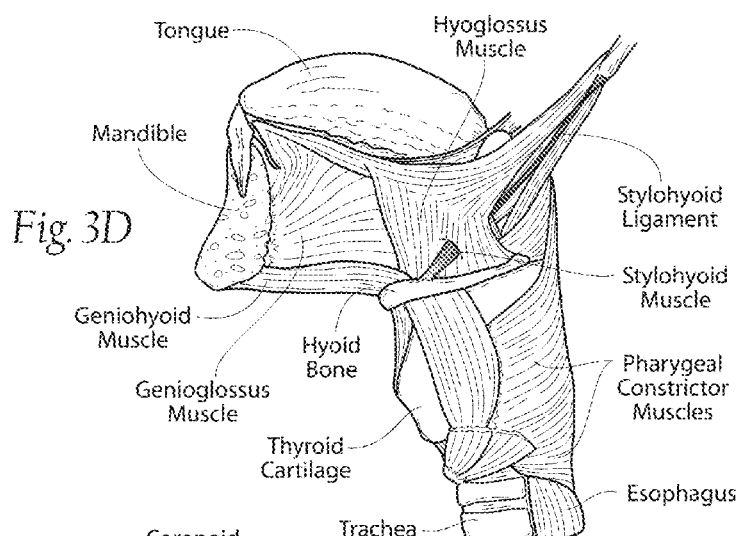
FIG. 3D is an anatomic side elevation view of the extrinsic muscles of the tongue, external larynx, and pharynx.

As FIG. 3D shows, thick fibers of constrictor muscles and connective tissue attach the pharynx to the base of the skull and surrounding structures. Both circular and longitudinal constrictor muscles occur in the walls of the pharynx. The circular muscles form constrictions that help push food to the esophagus and prevent air from being swallowed. The longitudinal muscles lift the walls of the pharynx during swallowing.

B. The Mandible

Please ref to FIGS. 2A and 2B. The mandible is the lower jaw. It is a U-shaped bone having alveolar processes that house the mandibular teeth.

The ascending parts of the mandible at the side are called rami (branches). The joints by means of which the lower jaw is able to make all its varied movements are between a rounded knob, or condyle, at the upper back corner of each ramus and a depression, called a glenoid fossa, in each temporal bone. The hinge-type joint that is formed between these articular surfaces is called the temporomandibular joint (TMJ). Another, rather sharp projection at the top of each ramus and in front, called a coronoid process, does not form part of a joint. Attached to it is the temporalis muscle, which serves with other muscles in shutting the jaws.

Several muscle groups (not shown) act on the TMJ to (i) elevate the mandible, closing the jaws; (ii) protrude the jaw; (iii) depress the chin; (iv) produce side-to-side movement of the jaw; (v) elevate the mandible, closing the jaws; and (vi) produce a grinding motion for cutting food.

C. The Neck

The neck (see FIG. 3C) is the portion of the body joining the head to the shoulders and chest. The neck is a major conduit between the head, trunk, and limbs. Many important anatomic structures are crowded together in the neck, such as muscles, veins (e.g., the jugular veins), arteries (e.g., the carotid arteries), vertebrae (e.g., the seven cervical vertebrae and enclosed spinal cord), the pharynx, and part of the esophagus. A broad, thin plane of muscular fibers, called the platysma myoides or platisma, extends immediately beneath the superficial fascia of each side of the neck. Food and air entering the oral cavity must pass through the neck.

Also present in the neck is the hyoid bone, as FIG. 3D prominently shows. The hyoid bone lies in the anterior part of the neck at the level of the C3 vertebra in the angle between the mandible and the thyroid cartilage, which is the largest cartilage of the larynx.

1. The Hyoid Bone

A primary function of the hyoid bone is to serve as an anchoring structure for the tongue. As FIG. 3D shows, the hyoid bone is situated at the root of the tongue in the front of the neck and between the mandible and the thyroid cartridge. The hyoid bone has no articulation with other bones. It serves a purely anchoring function. The hyoid bone is suspended from the styloid processes of the temporal bones by the stylohyoid ligaments (as FIGS. 3C and 3D show, as also shown in FIG. 3A). The hyoid bone is firmly bound to the thyroid cartilage (as FIG. 3C shows in an anterior view). It serves as an anchoring point for muscles of the tongue and, thus, as a prop to the keep the tongue from blocking the airway, as will be described in greater detail later.

Figure 3E:
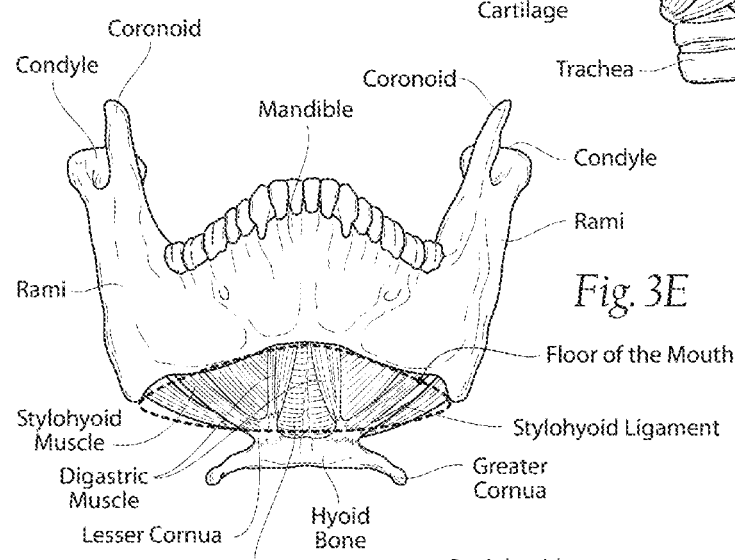
FIG. 3E is an anatomic anterior view of the mandible and suprahyoid muscles and floor of the mouth, viewed from below.
Figure 3F:
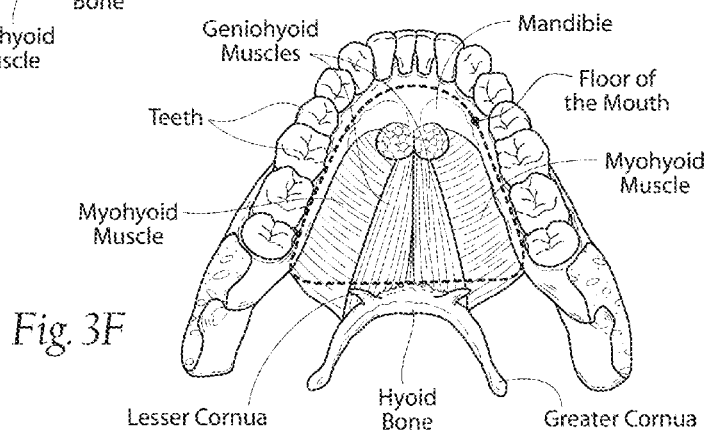
FIG. 3F is an anatomic superior view of the floor of the mouth showing the mylohyoid and geniohyoid muscles.

As best shown in FIGS. 3E and 3F, the hyoid bone consists of a body, a pair of larger horns (the greater cornua), and a pair of smaller horns (the lesser cornua). The hyoid bone is more or less in the shape of a U, with the body forming the central part, or base, of the letter. In the act of swallowing, the hyoid bone, tongue, and larynx all move upward rapidly.

The greater cornua are the limbs of the U. Their outer ends generally are overlapped by the large sternocleido-mastoid muscles (see FIG. 3C), which run from the sternum and clavicle to the mastoid region at the base of the skull on each side of the head just below and behind the ear in humans. The lesser cornua are small projections from the places called the junctions of the body and the greater cornua.

2. The Genioglossus Muscle is Attached to the Hyoid Bone

The genioglossus muscle is attached to the hyoid bone (see FIGS. 3A, 3B, and 3D). Fan-shaped, the genioglossus muscle contributes to most of the bulk of the tongue. The "root of the tongue" is defined as the inferior, relatively fixed part of the tongue that is attached to the hyoid bone and mandible. Acting bilaterally, the genioglossus muscle depresses the central part of the tongue, creating a central groove or furrow. Acting unilaterially, the genioglossus muscle will deviate (or "wag") the tongue toward the contralateral side.

3. Other Muscles in the Neck Are Attached to the Hyoid Bone

In the anteriolateral part of the neck, the hyoid bone provides for attachments for other. Among these are certain suprahyoid muscles superior (above or cranial) to the hyoid bone.

Suprahyoid muscles attached to the hyoid bone include the mylohyoid muscles (shown in FIGS. 3A and 3B). The mylohyoid muscles originate from the mylohyoid line of the mandible (which lies along a lateral side of the mandible between the angle of the mandible and the front of the mandible, also called mental protuberance). The mylohyoid muscles form the mobile but stable floor of the mouth and a muscular sling interior to the tongue that serves as a diaphragm. These muscles support the tongue and elevate it and the hyoid bone when swallowing or protruding the tongue.

Suprahyoid muscles attached to the hyoid bone also include the two geniohyoid muscles (also shown in FIGS. 3A and 3B). The two geniohyoid muscles originate close to the point at which the two halves of the mandible meet. The geniohyoid muscles are superior to the mylohyoid muscles, where they reinforce the floor of the mouth. The fibres of the muscles extend downward and backward, close to the central line, to be inserted into the body of the hyoid bone. Contraction of the muscles pulls the hyoid bone upward and forward, to shorten the floor of the mouth and widen the pharynx.

Suprahyoid muscles attached to the hyoid bone also include the two digastric muscles ((see FIGS. 3C and 3E), which also originate from the diagastric fossa of the mandible and the mastoid notch of temporal bone. The diagrastric muscles descend toward the hyoid bone and are joined by an intermediate tendon. A fibrous sling derived from the deep cervical fascia allows each muscle to slide anteriorly and posteriorly as it connects this tendon to the body and greater cornua of the hyoid bone. The digastric muscles depress the mandible, while also raising and steadying the hyoid bone during swallowing and speaking.

Inserting into the middle part of the lower border of the hyoid bone are the sternohyoids (shown in FIGS. 3C and 3E), which are long muscles arising from the breastbone and collarbone and running upward and toward each other in the neck. Other muscles attached to the hyoid bone are the thyrohyoid (shown in FIG. 3C), arising from the thyroid cartilage of the larynx (which depresses the hyoid bone and elevates the larynx); the omohyoid (not shown), which originates from the upper margin of the shoulder blade and the suprascapular ligament (which depresses, retracts, and steadies the hyoid bone); and the stylohyoid (shown in FIGS. 3B, 3C, and 3E), arising from the styloid process of temporal bone (which elevate and retracts the hyoid bone, thereby elongating the floor of the mouth).

4. Swallowing

The position of the hyoid bone with relation to the muscles attached to it has been likened to that of a ship steadied as it rides when anchored "fore and aft." Through the muscle attachments, the hyoid bone plays an important role in mastication, in swallowing, and in voice production.

For example, at the beginning of a swallowing motion, the geniohyoid and mylohyoid muscles elevate the hyoid bone and the floor of the mouth simultaneously. These muscles are assisted by the stylohyoid and digastric muscles. The tongue is pressed upward against the palate and the food is forced backwards.

II. Collapse of the Airway

As shown in FIG. 4, the airway is the path that air follows to get into and out of the lungs. The mouth and nose are the normal entry and exit ports. Entering air passes through the mouth, between the tongue and palate, to the back of the throat (pharynx), and continues through the voice box (larynx), down the trachea, and finally out the branching tubes in the lungs, known as bronchi (not shown). A normal breath of air passes through the oral or nasal passages, behind the palate, uvula, and root of the tongue, then into and through the pharyngeal airway, and between the vocal cords of the larynx into the lungs.

As shown in FIG. 4, under normal breathing conditions, in a healthy person who is awake, active, and upright, the force of gravity naturally draws the tongue, tissue structures in the floor of the mouth, and tissue in the neck in a caudal direction, i.e., toward the feet. The force of gravity provides, when a person is upright, a natural bias to the tongue, tissue structures in the floor of the mouth, and tissue in the neck toward the feet mostly out of the path that air follows in the oral cavity. The caudal gravitational bias provided when a person is upright maintains a desired tongue orientation out of the airway in the oral cavity, thereby providing beneficial spacing between tongue and the palate, as well as maintains a desired orientation of neck tissue out of the airway.

Further, when a healthy person is awake and active, the coordinated activity of muscles of the tongue, floor of the mouth, neck, upper part of the pharyngeal airway or throat, and/or mandible serves also to keep the airway open to allow air to flow through the nasal passages, behind the palate, uvula, and tongue base, through the airway, and between the vocal cords and into the lungs.

However, during sleep (see FIG. 5), the tongue, tissue structures in the floor of the mouth, and/or tissue in the neck can shift or collapse as they lose tension and as the sleeping body position alters the influence of gravity, into the airway. The undesired shifting or collapse of the tongue, tissue structures in the floor of the mouth, and/or tissue in the neck into the airway during sleep can be attributed to one or a combination of causes.

One cause is gravity. During sleep, a person is no longer upright, but is instead lying down in a prone, supine, or side position. The pull of gravity on tissue of a person lying down is not toward the feet. Instead, the force of gravity on a person lying down serves to shift the orientation of the tongue, and/or tissue structures in the floor of the mouth, and/or tissue in the neck inward and/or toward the airway.

Another cause is that, during sleep, many of the muscles in or affecting the tongue, neck, upper part of the pharyngeal airway, and/or mandible can undergo phasic changes in their electrical activity synchronous with respiration, leading to relaxation of these muscles. During one particular stage of sleep, the stage of rapid eye movement (REM), the muscles may completely relax. The muscles also completely relax during exhalation, prior to the beginning of inhalation.

Also, during sleep, muscles affecting the mandible can relax. The mandible drops (as FIG. 6 shows), and the mouth opens. During sleep, the head may also rotate inferiorly in flexion, or translation may occur within the TMJ to cause a posterior sliding of the mandible. The shift in mandible and/or head orientation during sleep leads to a shortening of the native anterior-to-posterior distance between the mandible and hyoid bone within the floor of the mouth.

The native anterior-to-posterior distance between the mandible and hyoid bone is shown as D1 in FIG. 4. A shortened anterior-to-posterior distance between the mandible and the hyoid bone, caused by a shift in the mandible and/or head orientation during sleep is shown as D2 in FIG. 6. As a comparison between D1 (FIGS. 4) and D2 (FIG. 6 shows, D2 is less than D1.

As the anterior-to-posterior distance is reduced by mandible and head orientation, the tongue and tissue structures in the floor of the mouth, which occupy this space, are shifted inward and toward the airway.

Also, during sleep, as a result of the diminution or absence of native muscle activity, the position of the root of the tongue can shift in a posterior direction, toward and into the airway. Further, during sleep, the diminution or absence of native muscle activity in the neck can lead to the collapse of tissue in the neck toward and into the airway.

As FIG. 5 shows, for many individuals, the airway remains open enough, despite the sleep-related effects of gravity on tissue, and/or changes in mandible and head orientation, and/or relaxation of one or more of muscles affecting the tongue, floor of the mouth, or neck, to permit the flow of air during sleep.

As shown in FIG. 6, other individuals, however, are, for various reasons, more prone to experiencing more chronic or sever breathing restrictions as the airway narrows. For such individuals, narrowing of the airway during sleep can be accompanied by a sleep disordered breathing condition, such as habitual snoring or obstructive sleep apnea (OSA). Such individuals may even experience a cessation of breathing, which leads to a marked fall in blood oxygen levels, terminating in arousal, making it impossible to achieve deep, restorative sleep.

For example, in some individuals, due to hereditary, disease, neuromuscular dysfunction, or obesity, tissue structures within the mouth, such as the soft palate, uvula, and/or tongue may be enlarged or have lost compliance, or the walls of the pharyngeal airway itself may have narrowed due to tissue enlargement or lack of tissue compliance in regions of the neck. For such individuals, relaxation of muscles of the mandible, tongue, neck, and/or upper part of the pharyngeal airway, can lead to tissue in the floor of the mouth, and/or at the root of the tongue, and/or along the neck falling into the oral, nasal, or pharyngeal regions of the airway, thereby obstructing or completely closing the airway for breathing. In some individuals, this result is exacerbated if the person is resting in a supine position, flat on their back. Loud snoring and labored breathing can occur. When complete blockage of the airway occurs (as FIG. 6 shows), air cannot reach the lungs. Breathing stops, until the shortage of oxygen in the blood stream awakes the person, or causes the level of sleep to become more shallow. If these episodes repeatedly occur during sleep, the condition is called obstructive sleep apnea. Partial blockage of the airway can also lead to a drop in the blood oxygen level (called oxygen desaturation) and a condition called hypopnea. Hypopnea can also lead to obstructive sleep apnea.

III. Implants in, on, or Near the Floor of the Mouth

A. Overview

As FIGS. 1A and 1B show, the oral cavity is framed by relatively stable structures—i.e., the rigid structures comprising the hard palate and cervical spine—and the floor of the mouth. The floor of the mouth comprises muscles such as the mylohyoid and geniohyoid. The floor of the mouth is bounded by the rigid, movable structures of the mandible (anterior) and the hyoid bone (posterior). The muscles of the floor of the mouth extend between these rigid, movable structures. Along with the mandible and the hyoid bone, the muscles in the floor of the mouth also serve as an anchoring structure for the tongue (the genioglossus muscle). The region behaves like a trampoline, stabilizing these structures, while accommodating relative movement among them.

Figure 1C:
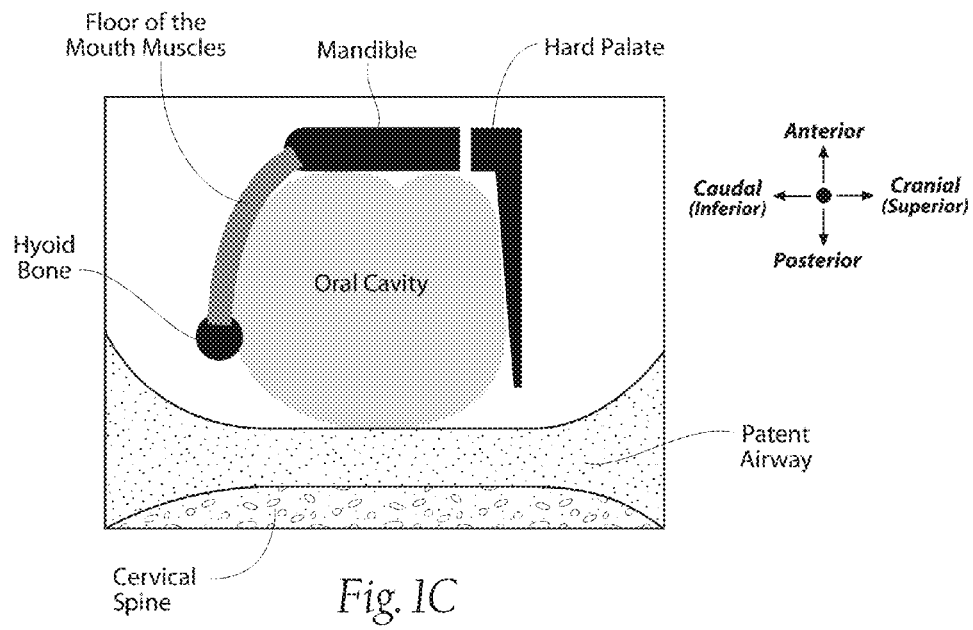
FIGS. 1C and 1D are diagrammatic views of an oral cavity and an airway, showing how a change in the frame size of the oral cavity affects airway patency.

While awake, the frame size is maintained by active tension in the floor of the mouth muscles (i.e., keeping the trampoline taunt). The active tension in the frame in turn maintains the anterior position of the mandible, creating more volume in the oral cavity and thus an airway of sufficient diameter. This is also shown diagrammatically in FIG. 1C.

Figure 1D:
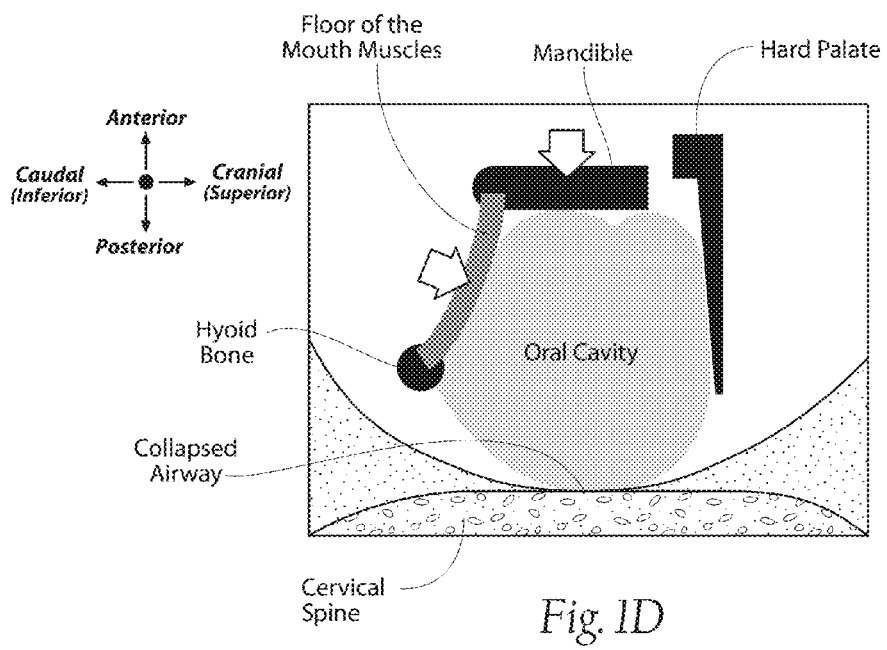

However, absence of muscle activity during sleep, gravity, and the negative pressure cascade during the breathing cycle all create conditions for the tongue to slide in a posterior direction and close the airway. This is shown diagrammatically in FIG. 1D. During sleep, the floor of the mouth muscles lose active tension, and the trampoline becomes slack. The mandible drops and falls back (in a posterior direction) due to lack of tension in other muscles. The slack muscles in the floor of the mouth buckle or bend inward, because the tongue pulls the muscles in the floor of the mouth inward. The mandible repositions toward the airway, shortening the distance between the mandible and the hyoid bone. The frame size of the oral cavity decreases. The tongue slides to the posterior and closes the airway.

Figure 7A:
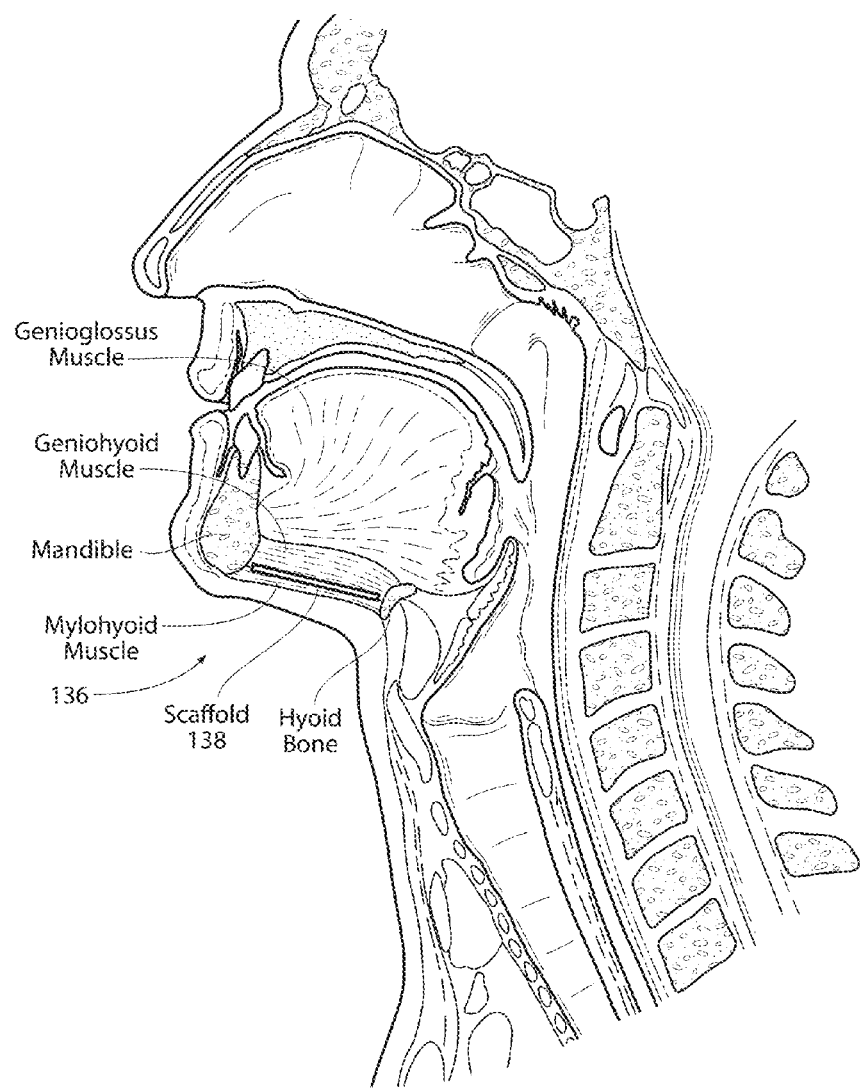
FIGS. 7A, 7B, 7C, 7D, and 7E are anatomic views of an oral cavity and adjacent structures an adult human, with the mouth closed, showing the presence of a scaffold structure implanted in, on, or near tissue structures in the floor of the mouth (more particularly, between the mylohyoid and geniohyoid muscles), which mechanically supports the tissue structures in a desired orientation to stabilize the tissue structures and affirmatively resist their movement into an airway.
Figure 7B:
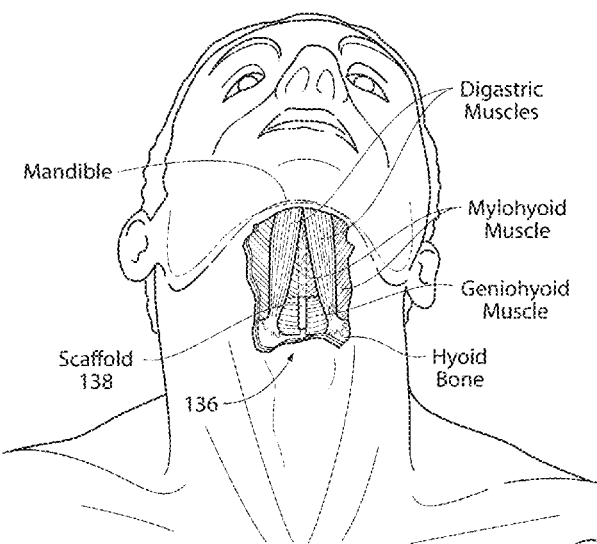
Figure 7C:
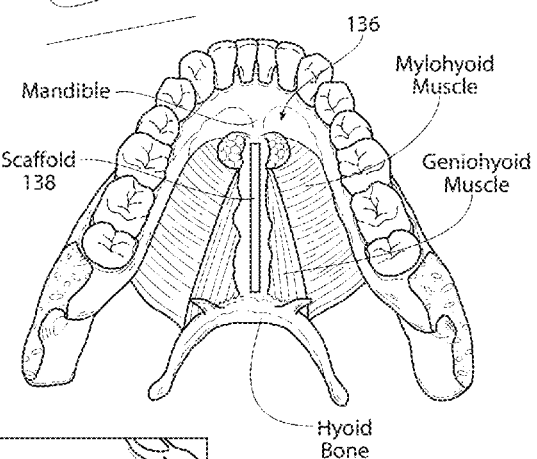

FIGS. 7A, 7B, and 7C show a system 136 comprising at least one scaffold structure 138 placed in, on, or near selected tissue regions in the floor of the mouth. In use, the scaffold structure 138 helps an individual with a sleep disordered breathing condition, such as habitual snoring or obstructive sleep apnea (OSA), achieve deep, restorative sleep. As FIGS. 7A, 7B, and 7C show, at least one of the scaffold structures 138 is placed in, on, or near the selected tissue regions in the floor of the mouth between the anterior part of the mandible and the hyoid bone.

The diverse tissue structures occupying the floor of the mouth comprise layers of dermis, fat, and muscle, which are mutually interconnected from the epidermis inward to the genioglossus muscle, tongue and base of the tongue. Due to their native, interconnected morphology, the application of a force to brace, move, or constrain one of these tissue structures in effect braces, moves, or constrains them all to various degrees. By analogy, this structure has previously compared to a trampoline, which provides for both motion and stabilization of the tongue. The scaffold structure 138, in effect, stiffens and shapes the trampoline.

The scaffold structure 138 comprises a body made from a biocompatible metallic or polymer or fiber material, or a combination thereof, or a metallic or polymer or fiber material that is suitably coated, impregnated, or otherwise treated with a material to impart biocompatibility, or a combination of such materials.

The physical characteristics of the scaffold structure 138 body are selected in term of length, thickness, elasticity, tensile strength, flexure (Standard Gurley Units), compressibility, spring constant, torque, shape, etc., so that, when placed in tissue, the scaffold structure 138 mechanically supports the selected tissue region in a desired orientation in the floor of the mouth, even in the absence or diminution of native muscle activity in that region. To achieve this function, the scaffold structure 138 can comprise a rigid material, or a semi-rigid, or an elastic and/or flexible material with a selected spring constant (e.g., a spring constant sized and configured to work without damaging tongue tissue), or an electrically actuated shaped material, or a thermally activated shaped material, or a mechanically actuated material (e.g., similar to a hair clip), or a magnetically actuated material, or combinations thereof.

Figure 12:
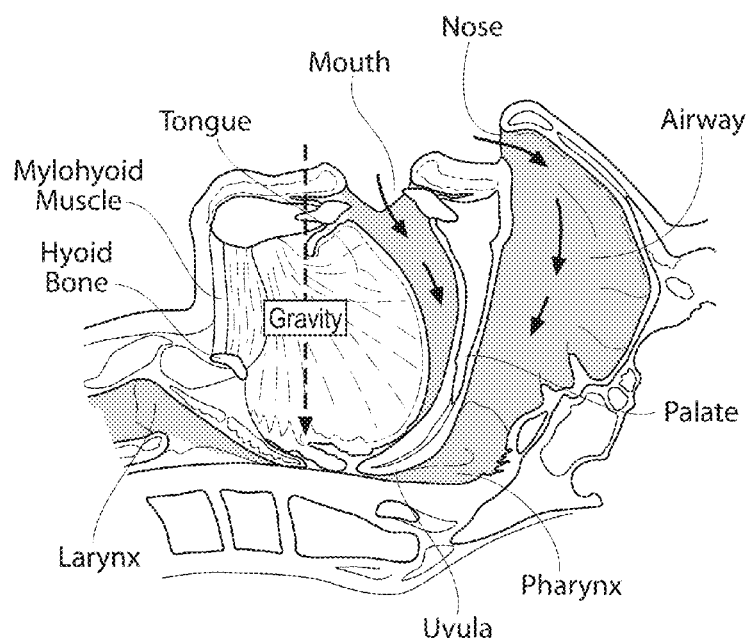
FIG. 12 is an anatomic side section view of an oral cavity, pharynx, and larynx of an adult human, in a supine sleep position with the mouth opened, showing the effects of gravity and an opened mouth on tissue structures along an airway, being annotated to show the collapse of certain tissue structures into the airway and the resultant obstruction of airflow.
Figure 13A:
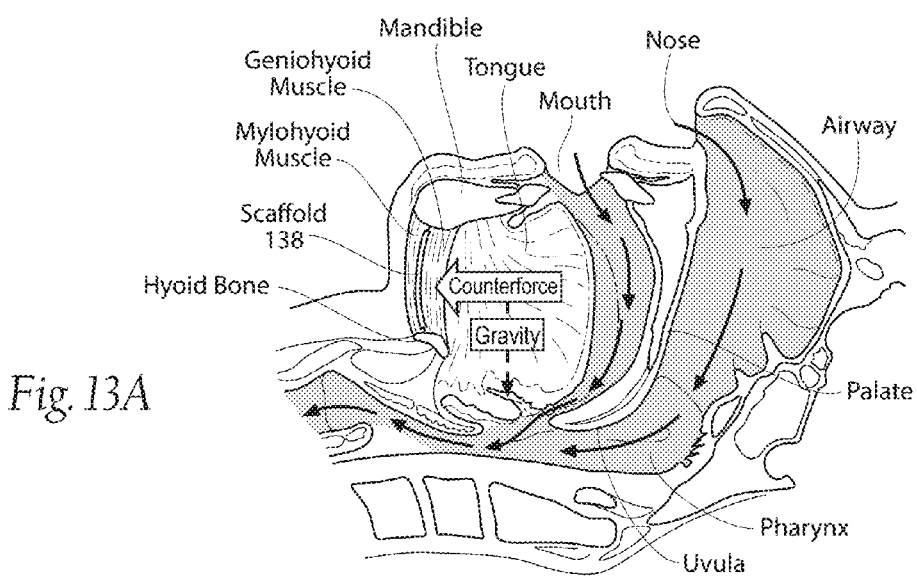
FIG. 13A is an anatomic side section view of the oral cavity of the individual shown in FIG. 12, annotated to show a scaffold structure like that shown in FIGS. 7A to 7D functioning to mechanically support tissue structures in, on, or near the floor of the mouth and affirmatively resist their movement into an airway.

As shown in FIGS. 12 and 13A, the desired orientation provided by the scaffold structure's mechanical support can, e.g., serve to resist undesired posterior movement of a tongue during sleep. As previously described with respect to FIG. 1D (and as also shown anatomically in FIG. 12), a lack of native muscle activity in the floor of the mouth during sleep can cause the root of the tongue to fall posteriorly, to narrow or obstruct the airway. As previously described, the mandible drops and falls back (in a posterior direction); the muscles in the floor of the mouth buckle or bend inward; and the mandible repositions toward the airway, shortening the distance between the mandible and the hyoid bone. This change in distance and tension between the mandible and hyoid bone leads to a decrease in the frame size of the oral cavity. The decrease in frame size causes the tongue to collapse into the airway. The tongue slides in a posterior direction and closes the airway.

As FIG. 13A shows, the mechanical support of the scaffold structure 138 in the floor of the mouth conditions tissue to support the tongue in a desired anterior orientation, in effect mimicking native muscle activity that supports the tongue through interaction with the hyoid bone. Referring again to the analogy, the scaffold structure 138 stiffens and shapes the trampoline. This is shown diagrammatically in FIG. 13B. The scaffold structure 138 increases the tension in the floor of the mouth, preventing inward buckling and stabilizing the floor of the mouth to increase resistance to posterior tongue collapse. The scaffold structure 138 increases the distance and maintains tension between the mandible and hyoid bone, biasing the position of the mandible toward a mouth closed, chin up, jaw forward orientation. The mechanical support of the scaffold structure 138 in the floor of the mouth stabilizes the tissue region in the absence of the native muscle activity during sleep, to resist posterior movement of the tongue into the pharyngeal airway.

The desired orientation provided by the scaffold structure's mechanical support can also, e.g., serve to bias the displacement of tissue structures in, on, or near the floor of the mouth away from the airway when the mandible opens. As previously described, when the mandible opens (articulates downward), the anterior-to-posterior distance between the mandible and hyoid bone shortens, and tissue structures in, on, or near the floor of the mouth shift. Typically, due to the gravity position of the individual when sleeping (no longer upright), and the relaxation of muscles during sleep, when the mouth opens, tissue structures in, on, or near the floor of the mouth tend to shift toward the airway. The scaffold structure's mechanical support resists this tendency, by the creation of a counter force that directs the tissue structures out of the airway, as shown by the counterforce arrow in FIG. 13A. The scaffold structure 138 thereby reshapes the floor of the mouth. The outward force counteracts the inward force due to gravity. The scaffold structure 138 thereby stabilizes the frame size of the oral cavity, resisting a decrease (i.e., reduction) in the frame size, while also stabilizing the frame size in this desirable condition. The presence of the scaffold structure 138 provides a subtle shift in the balance of forces in the oral cavity during sleep, to stabilize the tongue base and maintain oral cavity volume by stabilizing and thereby resisting a decrease (reduction) in the frame size and/or by shifting the balance of forces sufficiently to actually increase the frame size. Even a small increase in the cross sectional area of the airway results in an exponential improvement in airway stability.

The desired orientation provided by the scaffold structure's mechanical support can also, e.g., affirmatively serve to resist posterior translation of the TMJ, without opening the mouth during sleep. As previously described, a lack of native muscle activity can cause a posterior translation of the TMJ, which, in turn, can cause a narrowing of the pharyngeal airway. The mechanical support of the scaffold structure 138 in the floor of the mouth conditions tissue to resist posterior translation of the TMJ during sleep, to stabilize the tissue region in the absence of the native muscle activity during sleep, to resist narrowing or closure of the pharyngeal airway.

An exterior surface of the scaffold structure 138 can be roughened or the scaffold structure 138 can be perforated, to encourage tissue in-growth and prevent migration within tissue. The roughened surface can comprise, e.g., a microporous surface to prevent migration and/or promote tissue in-growth. In this arrangement, a resorbable suture material can be used to initially stabilize the scaffold structure's position in tissue, until tissue in-growth occurs.

Additionally, or instead of promoting tissue in-growth, the scaffold structure 138 may be sutured to surrounding tissue or bone (mandible and/or hyoid bone), as desired, for stabilization. However, suturing is not believed to be necessary in all instances. Local tissue morphology will dictate whether suturing is required for stabilization. The most desired location for suturing is around the hyoid bone and/or to the connective tissue attached to the hyoid bone.

The scaffold structure 138 can be surface-treated to limit fibrous encapsulation, e.g., by ePTFE encapsulation, to maintain tissue flexibility around the device.

The scaffold structure 138 can be placed anywhere in, on, or near the floor of the mouth from the superficial dermis of the skin up to but desirably not substantially within the genioglossus muscle itself (i.e., in, or, or near the floor of the mouth). Because of the interconnected nature of tissue structures in this region, by stabilizing or bracing one of the tissue structures within the region, other interconnected tissue structures to can be stabilized and/or constrained.

B. Representative Embodiments

1. Anterior to Posterior Scaffold Structures

FIGS. 7 A/B/C show one basic representative embodiment of a scaffold structure 138, which is sized and configured to be implanted in a general anterior-to-posterior orientation in, on, or near selected tissue regions in the floor of the mouth.

The scaffold structure 138 can comprise a rigid, or semi-rigid, or flexible material, depending upon its size and shape. As shown, the scaffold structure 138 includes a side profile, measured in the inferior to superior direction when implanted, which is relatively thin but still possessing an organic shape that will not cut or damage tissue and will promote acceptance by the body. Representative side profiles can range, e.g., up to about 10 mm; however, a side profile of between about 1 mm and 4 mm is believed to be most desirable. This attributes lends comfort to the scaffold structure 138 when implanted.

In this arrangement, the scaffold structure 138 can be generally rectangular in shape, having a length greater than its width, to maintain a desired anterior-to-posterior orientation when implanted. Further, as shown in FIG. 7 A/B/C, the scaffold structure 138 can be sized in length to rest comfortably in the anterior-to-posterior space between the hyoid bone and the mandible. A representative length ranges between about 25 mm and about 45 mm. In a representative embodiment, the scaffold structure 138 can span essentially the entire anterior-to-posterior distance from the hyoid bone to the mandible, as FIGS. 7 A/B/C show. In another representative embodiments, the anterior region and the posterior region of the scaffold structure 138 rest about 5 mm from the mandible and hyoid bone, respectively. In these arrangements, and whenever the scaffold structure 138 is sized and configured to occupy a relatively large tissue volume, it becomes preferred that the scaffold structure 138 be flexible, allowing contraction so not to interfere with swallowing (i.e., smaller scaffold structures need not be as flexible as larger scaffold structures).

Figure 7D:
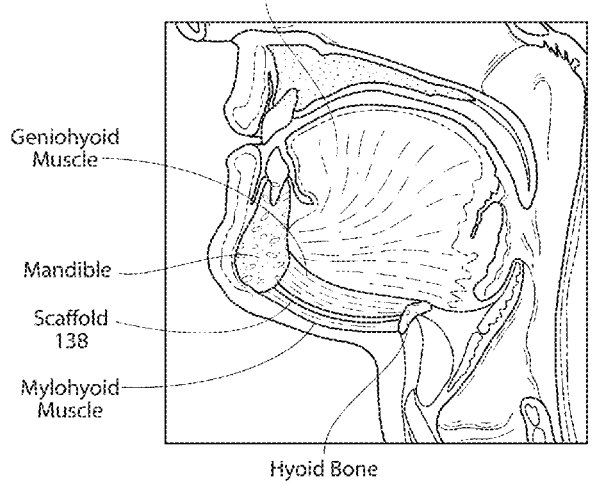

In the situation where a larger scaffold structure 138 is implanted, as FIG. 7D shows, it also becomes preferred that the scaffold structure 138 be further configured, when implanted in an anterior-to-posterior orientation in, on, or near the floor of the mouth, to resist buckling of tissue structures in, on or near the floor of the mouth in a cranial direction (i.e., inward into the oral cavity toward the top of the head) and/or to preferentially bend in a caudal direction (i.e., toward the feet). The body of the scaffold structure can rigid and molded or pre-shaped to possess a convex orientation facing the feet, or, if desired, be less rigid and preferably weakened (e.g., include areas of reduced thickness or slotted preferentially) or possess a spring constant, which preferentially bends the scaffold structure in the caudal direction. Thus, when the muscles in the floor of the mouth relax during sleep, or when the mandible opens/falls back (see also FIG. 13A), the scaffold structure 138 will either possess a pre-shape orientation toward the feet or will preferentially bend toward the feet and not into the oral cavity. The preferential bending should occur with minimal force, i.e. less than what would cause posterior displacement of the hyoid bone. Alternatively, however, the scaffold structure 138 could require more force to preferentially bend toward the feet and can be coupled with a hyoid bone stabilization device or procedure done in conjunction or separately, as will be described in greater detail later.

Figure 7E:
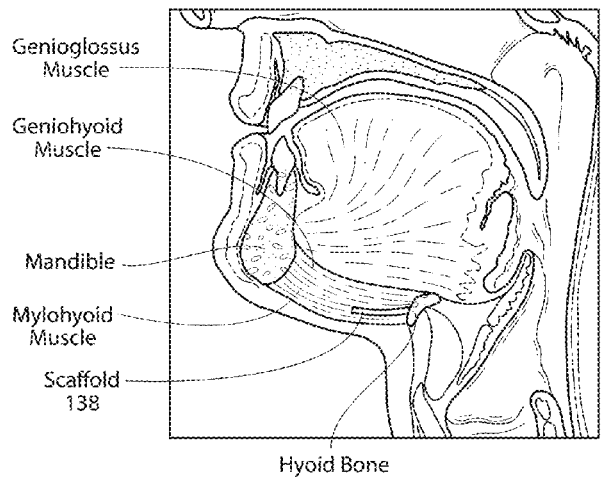

In another representative embodiment, the scaffold structure 138 can rest closer to or farther from the mandible and/or hyoid bone. For example, as FIG. 7E shows, the scaffold structure 138 can rest close to or even against the hyoid bone and extend only far enough in an anterior direction to reach the most unstable tissue region in the floor of the mouth, which is often closer to the hyoid bone than to the mandible. In this case, the distance from scaffold structure 138 anteriorly to the mandible may be quite large, e.g., 2 cm.

Figure 8:
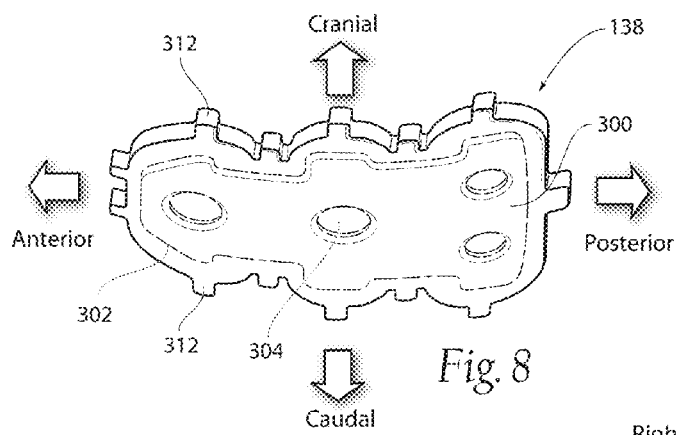
FIG. 8 is a perspective view of a representative embodiment of a scaffold structure sized and configured to be implanted in, on, or near tissue structures in the floor of the mouth to resist buckling of the tissue structures in a cranial direction (i.e., inward into the oral cavity toward the top of the head) and/or to preferentially bend in a caudal direction (i.e., toward the feet), the scaffold structure being rigid and molded or pre-shaped to possess a convex orientation facing the feet.
Figure 9:
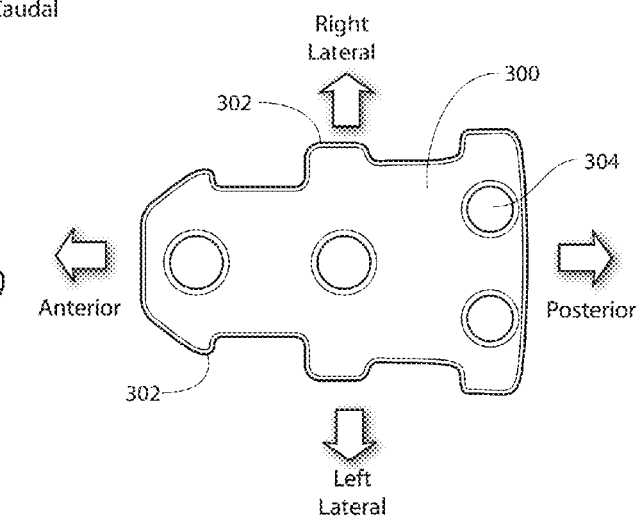
FIG. 9 is a top view of the rigid skeleton of the scaffold structure shown in FIG. 8.
Figure 10A:
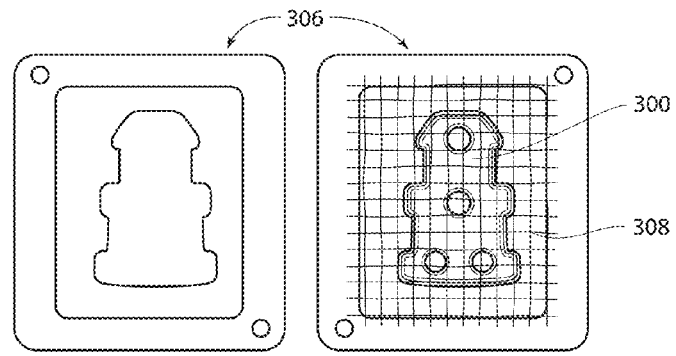
FIG. 10A is a top view of a mold into which the rigid skeleton shown in FIG. 9 is placed along with a fabric, and into which silicone is introduced to encapsulate the skeleton and fabric.
Figure 10B:
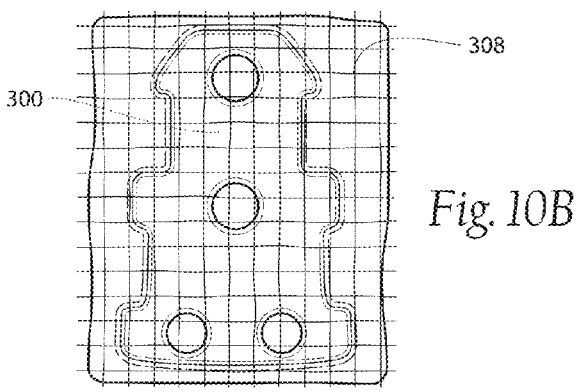
FIG. 10B is a top view of the skeleton and fabric after having been encapsulated with silicone inside the mold shown in FIG. 10A.
Figure 11A:
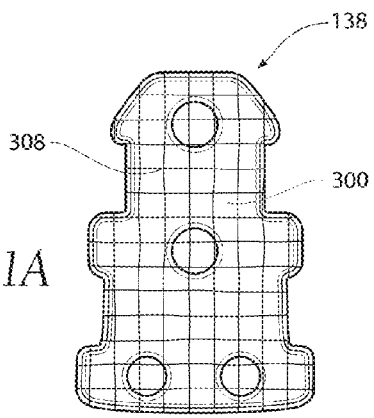
FIG. 11A is the skeleton and fabric encapsulated with silicone, as shown in FIG. 10B, after trimming the edges of the fabric and silicone near the skeleton.
Figure 11B:
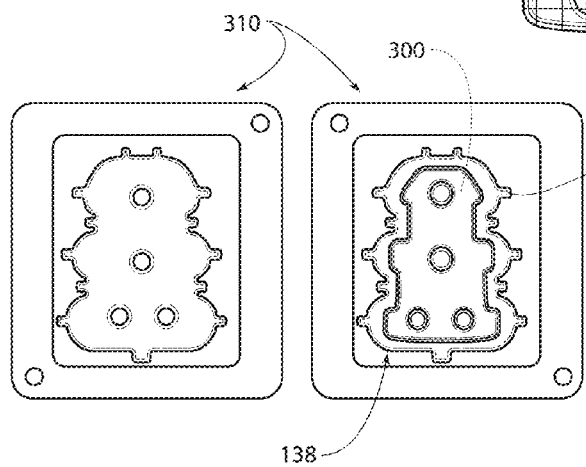
FIG. 11B is the skeleton and fabric encapsulated with silicone, after the edges have been trimmed as shown in FIG. 11A, placed within a mold to introduce more silicone to extend the edges and to add silicone fingers that project beyond the preformed edges of the skeleton, to finalize the manufacture of the scaffold structure shown in FIG. 8.

FIG. 8 is a representative embodiment of a scaffold structure 138 sized and configured for implantation in, on, or near the floor of the mouth. The scaffold structure 138 includes a rigid metallic skeleton 300 (see FIG. 9), formed, e.g., from titanium (about 2 mm in thickness). The metallic skeleton 300 includes preformed projecting edges 302 to resist migration of the structure when implanted in tissue, as well as preformed perforations 304 for tissue in-growth and suturing when implanted. The metallic skeleton 300 is pre-shaped to possess a convex orientation, which, when implanted in, or, or near the floor of the mouth, is oriented toward the feet. The titanium skeleton 300 is first placed within a mold 306 with a polymeric fabric 308 (e.g., polyester fabric, CR Bard Corporation, Billerica, Mass.) (see FIG. 10A. In the mold 306, medical implant grade silicone (MED Series, Nusil Corporation, Carpenteria, Calif.) is molded around the titanium skeleton 300 and fabric 308 (see FIG. 10B).). The fabric 308 helps to maintain the structure's integrity and prevent tearing or overstretching of the silicone near the titanium surface, while also maintaining the shape or form of the silicone. The fabric 308 can also add a roughened and/or microporous surface on the skeleton 300 to prevent migration and/or promote tissue in-growth. After this initial molding process, a cutting guide is used to cut fabric and silicone along the edges to about 1.5 mm from the edges of the metallic skeleton 300 (see FIG. 11A). In a second mold 310, the cut silicone/fabric edges are extended, by further introducing silicone to extend the edges and to add silicone fingers 312 that project beyond the preformed edges of the skeleton 300 (projecting about 2 mm) (see FIG. 11B).

Overall, once formed, the scaffold structure 138 measures about 25 to 45 mm along the longitudinal axis (anterior-to-posterior), about 15 to 25 mm along the anterior lateral axis, and about 25 to 35 mm along the posterior lateral axis (i.e., the structure 138 tapers anterior-to-posterior), with a convex curvature having a radius of about 2.9 inches. Once formed, the scaffold structure 138 measures about 3 mm in thickness. When implanted in, on, or near the floor of the mouth, the longitudinal axis of the structure 138 is aligned along the anterior-to-posterior axis of the floor of the mouth between the mandible and hyoid bone, and the convex orientation of the scaffold structure faces the feet.

In use, when the scaffold structure 138 is implanted in a tissue structure in, on, or near the floor of the mouth with the longitudinal length of the scaffold structure oriented in an anterior-to-posterior direction, inferior/posterior rotation or posterior translation of the mandible tends to shorten the anterior-to-posterior distance between the hyoid bone and the mandible. As before described, a reduction in the anterior to posterior distance between the mandible and hyoid bone, if not resisted, will displace tissue structures in, on, or near the floor of the mouth cranially, toward the airway, as FIG. 12 shows. In contrast, as FIGS. 13 a/B show, the presence of the scaffold structure 138 will stiffen tissue structures in, on, or near the floor of the mouth, thereby resisting their displacement toward the airway. In this way, the scaffold structure 138 serves to stabilize tissue structures to resist their collapse in a cranial direction into the airway. The physical properties of the scaffold structure 138 should be moderated so that presence of the scaffold structure 138 does not cause posterior motion of the hyoid bone with mandible motion.

The pre-shaped convex orientation and/or preferential bending of a given scaffold structure 138 toward the feet can affirmatively influence mandibular motion. Even without affirmatively restricting mandibular motion, the scaffold structure 138 can respond to mandibular motion in a beneficial way, to force compressed tissue in the floor of the mouth to bend out (away from the floor of the mouth), rather than bend inward toward the airway (which is its native inclination, which is further assisted by the force of gravity when the individual is in a sleeping position).

2. Scaffold Structure Arrays

As FIG. 14A shows, more than a single scaffold structure 138 may be placed within a targeted tissue region in, on, or near the floor of the mouth. For example, as shown in FIG. 13A, three scaffold structures 138(a), 138(b), and 138(c), each having a width of about 3 mm can be placed in along the anterior-to-posterior distance of the tissue region, for a composite width of about 10 mm. Thus, a plurality of scaffold structures 138(a), 138(b), and 138(c) of lesser width (e.g., 1 mm to 3 mm) can be implanted in tandem to create wider transverse scaffold structure array. As FIG. 14B shows, the position of scaffold structures 138(1), 138(2), 138(3), 138(4), 138(5), 138(6), 138(7) can also be staggered along the anterior-to-posterior distance, forming an anterior-to-posterior array of scaffold structures 138(n). The number of scaffold structures 138(n), and thus the composite transverse width and anterior-to-posterior length of the array vary. The array of scaffold structures 138(n) can increase in width in an anterior-to-posterior direction (as FIG. 14B shows), so that the anterior width of the array (e.g., 10 mm to 20 mm) increases to a greater posterior width (e.g., 20 mm to 30 mm), providing with multiple scaffold structures a trapezoid shaped array. An array of scaffold structures 138(1), 138(2), and 138(3), if desired, can extend in a transverse orientation (as FIG. 14C shows), or in an oblique orientation (as FIG. 14D shows), or in prescribed and/or random combinations of anterior-to-posterior, transverse, and/or oblique orientations.

3. Molded Scaffold Structures

Figure 15A:
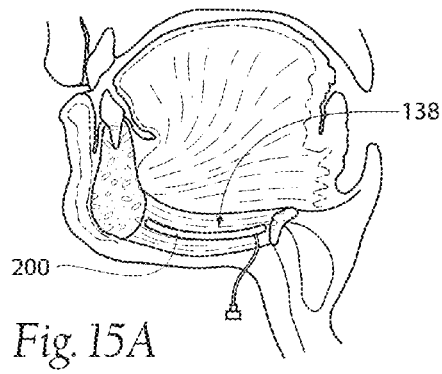
FIGS. 15A and 15B are anatomic views of an oral cavity, pharynx, and larynx of an adult human, with the mouth closed, showing the presence of a molded scaffold structure implanted in, on, or near tissue structures in the floor of the mouth.
Figure 15B:
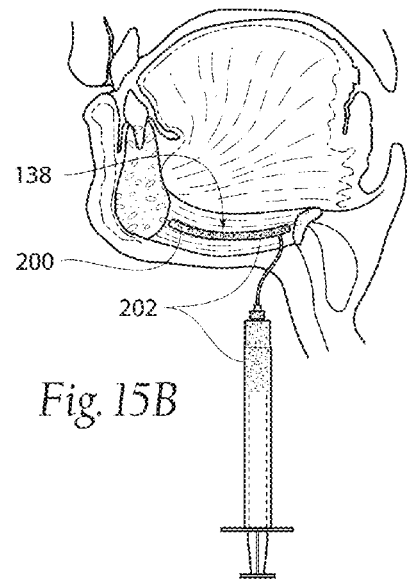

As FIGS. 15 A/B show, the scaffold structure 138 can also comprise a molded body 200 with an open interior sized and configured for the introduction of a shaping media 202, like air or liquid. The introduction of the shaping media 202 (see FIG. 15B) stiffens and/or shapes the body 200 in a desired way (e.g., causing the body 200 to assume a configuration that resists buckling in a cranial direction and/or to preferentially bend toward the feet). In this arrangement, the shaping media 202 can be introduced to stiffen and/or shape the body 200 at night, and the shaping media 202 removed during the day (as FIG. 15A shows) when stiffening and/or shaping is not required. The stiffening and/or shaping of the body 200 can be titrated, by adding more or less shaping media 202, to achieve the desired therapeutic effect. The shaping media 202 can comprise, e.g., a shape setting polymer.

The mechanical support that the resulting molded scaffold structure 138 provides stabilizes the tissue region, thereby providing affirmatively resistance to movement of the selected tissue region out of the desired orientation, which would otherwise occur due to the absence or diminution of native muscle activity in that region. The mechanical support that the scaffold structure 138 provides can also serve to dampen vibration of the tissue region, thereby moderating loud breathing or snoring during sleep.

4. In-Situ Scaffold Structures

Many upper airway condition of an individual can be characterized at least in part by a reduced stiffness of tissue structures in the floor of the mouth, between the anterior part of the mandible and the hyoid bone. Apparatus, systems, and methods can be provided that comprise an implant sized and configured to be implanted into tissue in, on, or near the floor of the mouth, which possesses the capability to stiffen and/or shape tissue structures in, on, or near the floor of the mouth.

As before described, a preformed scaffold structure 138 can be implanted having mechanical properties that stiffen and/or shape tissue structures in, on, or near the floor of the mouth, to resist movement of the tissue structures out of a desired orientation and into the airway, thereby moderating or preventing the incidence of sleep apnea.

Figure 15C:
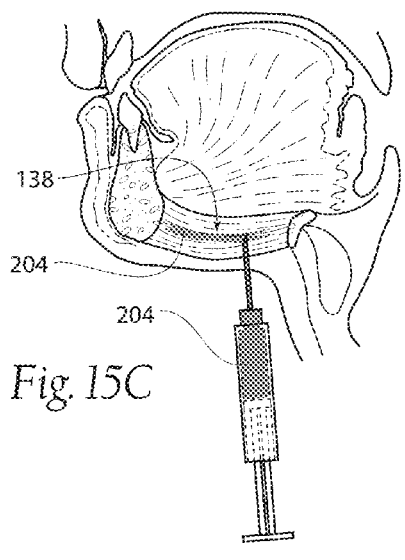
FIG. 15C is an anatomic view of an oral cavity, pharynx, and larynx of an adult human, with the mouth closed, showing the presence of an in-situ scaffold structure implanted in, on, or near tissue structures in the floor of the mouth.

Alternatively, as FIG. 15C shows, a fluid or material 204 can be injected directly into tissue in, on, or near the floor of the mouth (and not necessarily into a body or mold). In one embodiment, the material 204 stiffens and/or shapes by curing in situ by itself (e.g., by cross-liking) or in response to applied external energy such as light, ultrasound, heat, or radio frequency energy.

In another embodiment, the material 204 comprises an array of unitary structures or a bolus of particles, such as spheres or micro-beads or structures having other geometry, which are sized and configured to be distributed in one or more tissue structures in, on, or near the floor of the mouth. The unitary structures or particles can comprise, e.g., ceramic particles or titanium or pure carbon or other bio-compatible particles, such as vitreous carbon, zirconia ($ZrO_2$), alumina ($Al_2O_3$) or a polymeric. The unitary structures or particles can be carried in a liquid or gel medium. The unitary structures or particles can have disparate particle size distributions (i.e., a mix of two or more sizes of particles with the smaller particles filling interstitial spaces between larger particles). The unitary structures or particles can be implanted, e.g., by a needle to inject the bolus into one or more tissue structures in, on, or near the floor of the mouth. Multiple bolus injections can be made into one or more tissue structures in, on, or near the floor of the mouth, to form spaced apart deposits of the unitary structures or particles.

The distribution of unitary structures or particles adds mass to the tissue structures in, on, or near the floor of the mouth into which they are implanted, thereby stiffening and/or shaping the tissue structures in, on, or near the floor of the mouth and adding resistance to displacement. The unitary structures or particles can be sintered, or otherwise coated with a tissue growth inducing material, to encourage tissue in-growth to secure the unitary structures or particles in place. Also, placement of the unitary structures or particles can induce a fibrotic response, further acting to stiffen and/or shape the tissue structures in, on, or near the floor of the mouth. A sintered or coated unitary structure can enhance the fibrotic response and resulting stiffening.

The resulting scaffold structure 138 can also comprise a region of tissue in, on, or near the floor of the mouth that has been ablated, e.g., by the application of radio frequency energy, heat, laser, or cold, to form lesions and stiffen.

The mechanical support that the in situ scaffold structure 138 provides stabilizes the tissue region, thereby providing affirmatively resistance to movement of the selected tissue region out of the desired orientation, which would otherwise occur due to the absence or diminution of native muscle activity in that region. The mechanical support that the scaffold structure 138 provides can also serve to dampen vibration of the tissue region, thereby moderating loud breathing or snoring during sleep.

5. Trampoline Scaffold Structures

As before described, the muscles in, on, or near the floor of the mouth extend between rigid, movable structures. Along with the mandible and the hyoid bone, the muscles in the floor of the mouth also serve as an anchoring structure for the tongue. The region behaves like a trampoline, stabilizing these structures, while accommodating relative movement among them.

Figure 16:
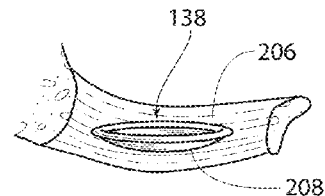
FIG. 16 is an anatomic view showing the presence of a trampoline scaffold structure implanted in, on, or near tissue structures in the floor of the mouth.

The scaffold structure 138 can mimic the structure of the floor of the mouth. In this arrangement, as shown in FIG. 16, the scaffold structure comprises a peripheral frame 206 sized and configured for implantation in, on, or near the floor of the mouth. The frame 206 supports an interior material 208 that is flexible, thereby forming a resilient, trampoline-like scaffold structure 138.

The interior flexible material 208 can comprise, e.g., flexible webbing or mesh material, or any synthetic fiber having elasticity, e.g., a polyurethane-polyurea copolymer such as "Spandex" or "Elastane" or "Lycra" or "Elaspan" or "Creora" or "ROICA" or "Dorlastan" or "Linel" or "ESPA". Alternatively, the entire trampoline scaffold structure 138 could comprise a flexible and/or elastic material formed in a saucer-like shape, e.g., silicone, or a nitinol material or nitinol mesh material or a stainless steel spring material embedded in an elastic or flexible polymer, such as polyurethane or "Spandex" or other materials listed above, or combinations thereof. The trampoline scaffold structure 138 is sized and configured to resist tissue buckling in a cranial direction and/or to preferentially bend in the caudal orientation, as previously described.

6. Spring Scaffold Structure

The scaffold structure 138 can comprise a formed spring structure 314 (see FIG. 17A) sized and configured to be implanted in, on, or near the floor of the mouth. The formed spring structure 314 applies tension to resist buckling of tissue structures in, on, or near the floor of the mouth in a cranial direction. As FIG. 17A, the spring structure 314 is desirably formed with a convex curve that, when implanted, is oriented in the direction of the feet. The curved configuration preferentially bends or biases the spring structure 314 in a caudal direction to increase the volume of the oral cavity.

The curved spring structure 314 can be made from a biocompatible metallic or polymer or fiber material, or a combination thereof, or a metallic or polymer or fiber material that is suitably coated, impregnated, or otherwise treated with a material to impart biocompatibility, or a combination of such materials.

Figure 17A:
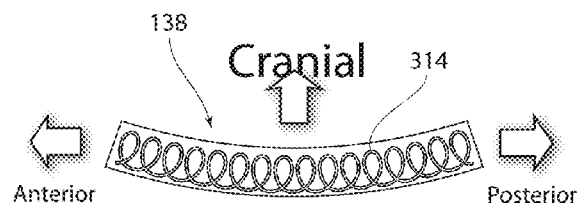
FIG. 17A is a side view of a representative embodiment of scaffold structure comprising a formed spring structure sized and configured to be implanted in, on, or near the floor of the mouth, to apply tension to resist buckling of tissue structures in, on, or near the floor of the mouth in a cranial direction, the spring structure being desirably formed with a convex curve that, when implanted, is oriented in the direction of the feet to preferentially bend or bias the spring structure in a caudal direction to increase the volume of the oral cavity.
Figure 17B:
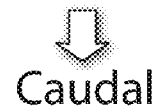
FIG. 17B is a side view of a scaffold structure comprising a spring structure that is initially formed to include bioadsorbable components placed between the helical coils that comprise the spring structure, the components normally holding the helical coils apart, but after the components are absorbed by surrounded tissue, the helical coils move together, and the spring structure assumes a normally curved configuration as shown in FIG. 17A.

As FIG. 17B shows, the spring structure 314 can be initially formed to include bioadsorbable components 316 placed between the helical coils that comprise the spring structure 314. The components 316 normally hold the helical coils apart, serving to urge the spring into a generally linear configuration, as shown in FIG. 17B. After implantation, as the bioadsorbable components 316 are progressively absorbed by surrounded tissue, the helical coils move together, and the spring structure 314 assumes its normally curved configuration, as shown in FIG. 17A. As the spring structure 314 returns to its normally curved configuration, it progressively applies tension to surrounding tissue to resist buckling of tissue structures in, on, or near the floor of the mouth in a cranial direction.

7. Lateral Scaffold Structure

Figure 18A:
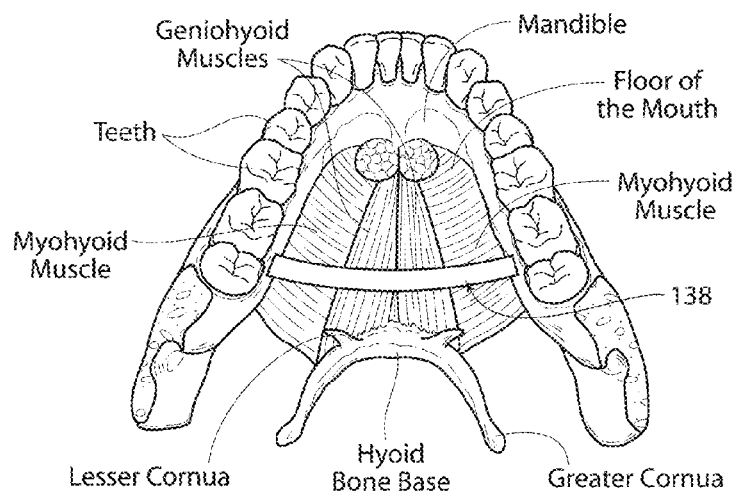
FIGS. 18A and 18B are anatomic views showing the presence of laterally oriented scaffold structures implanted in, on, or near tissue structures in the floor of the mouth.

Scaffold structures 138 that are sized and configured to be implanted in a general anterior-to-posterior orientation in, on, or near selected tissue regions in the floor of the mouth have been described. Alternatively, as FIG. 18A shows, scaffold structures 138 that are sized and configured to be implanted in a general lateral orientation in, on, or near selected tissue regions in the floor of the mouth can be used. Such laterally extending implants 138 can be wider than they are long, and need not have much longitudinal length to perform their intended therapeutic effect.

In one arrangement, as shown in FIG. 18A, a representative lateral scaffold structure 138 extends laterally substantially entirely across the floor of the mouth in, on, or near tissue structures between the lateral aspects of the mandible.

Figure 18B:
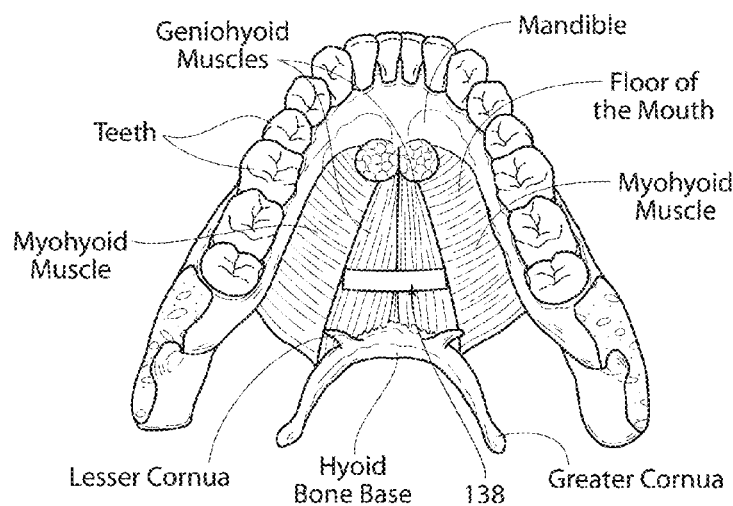

In another arrangement, as shown in FIG. 18B, a representative lateral scaffold structure 138 extends laterally in, on, or near tissue structures of the floor of the mouth near and anterior to the hyoid bone (that is, nearer to the hyoid bone than to the anterior mandible). Localized placement of a lateral scaffold structure 138 in this particular tissue region in, on, or near the floor of the mouth near and anterior to the hyoid bone can bring about stability to the entire floor of the mouth, and counteract and/or otherwise resist rotational movement of the hyoid bone and bending of tissue close to the hyoid bone toward the airway. The lateral scaffold structure 138 can be attached to the hyoid bone in one or several locations. As will be described in greater detail later, a lateral scaffold structure 138 located near the hyoid bone can be associated or integrated with a hyoid bone stabilization device.

8. Energy-Activated Scaffold Structures a. Overview

A given scaffold structure 138 can include components that are selectively activated, deactivated, and/or titrated by electrical, thermal, mechanical and/or magnetic energy to reshape, stiffen, or move the scaffold structure 138 to resist buckling of tissue structures in, on, or near the floor of the mouth in a cranial direction and/or to preferentially bend or bias the scaffold structure 138 in a caudal direction to increase the volume of the oral cavity.

b. Representative Embodiments

For example, in the representative embodiment generally shown in FIG. 19A, one or more magnets or ferrous materials 210 can be incorporated into any scaffold structure 138 that is sized and configured to be implanted in the floor of the mouth, as have been or will be described. The scaffold structure 138 itself can be flexible or rigid, or a combination thereof, and itself comprise ferrous and non-ferrous materials. As shown in FIG. 19B, one or more magnets or ferrous materials 210 can be incorporated into a scaffold structure 138 comprising a curved spring structure.

Figure 19A:
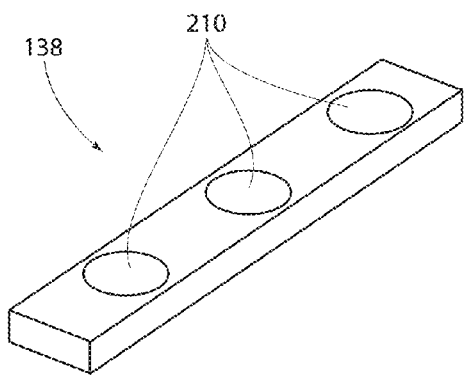
FIG. 19A is a side perspective view of a representative embodiment of a scaffold structure like that shown in FIG. 7A/B/C/D/E, but further including one or more magnets or ferrous materials.
Figure 19B:
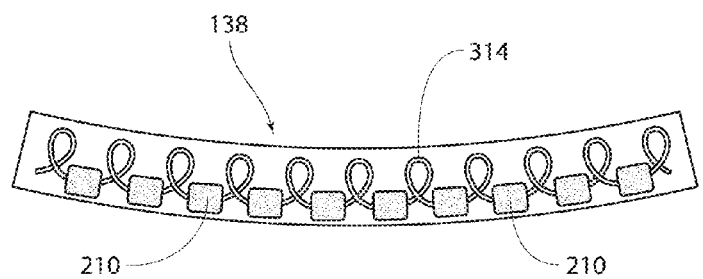
FIG. 19B is a side perspective view of a representative embodiment of a scaffold structure comprising a curved spring structure like that shown in FIG. 17A, but further including one or more magnets or ferrous materials.
Figure 19C:
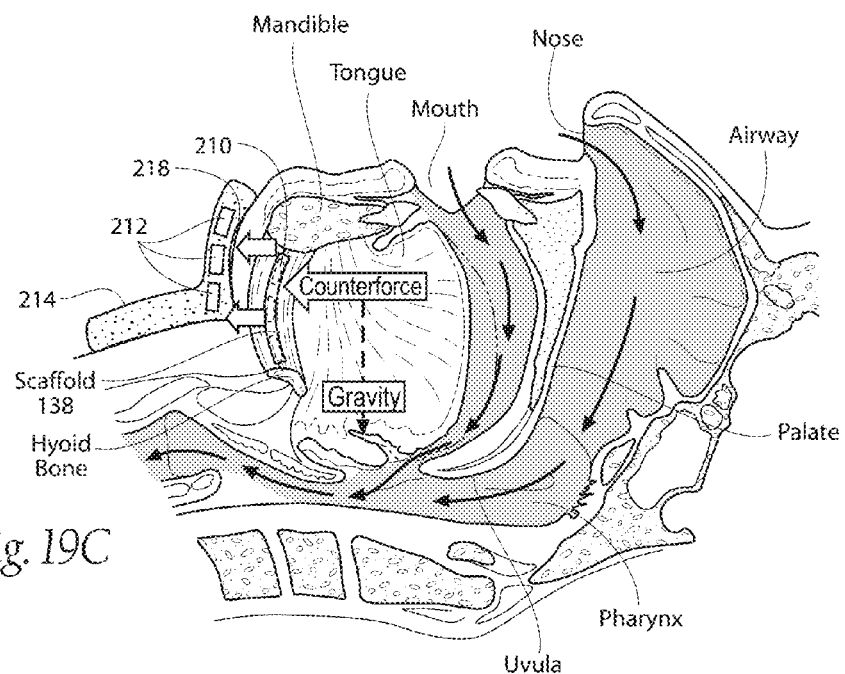
FIG. 19C is an anatomic side section view of an oral cavity, pharynx, and larynx of an adult human, with the mouth opened, showing an external carrier support that magnetically interacts with the scaffold structure shown in FIG. 19A.
Figure 19D:
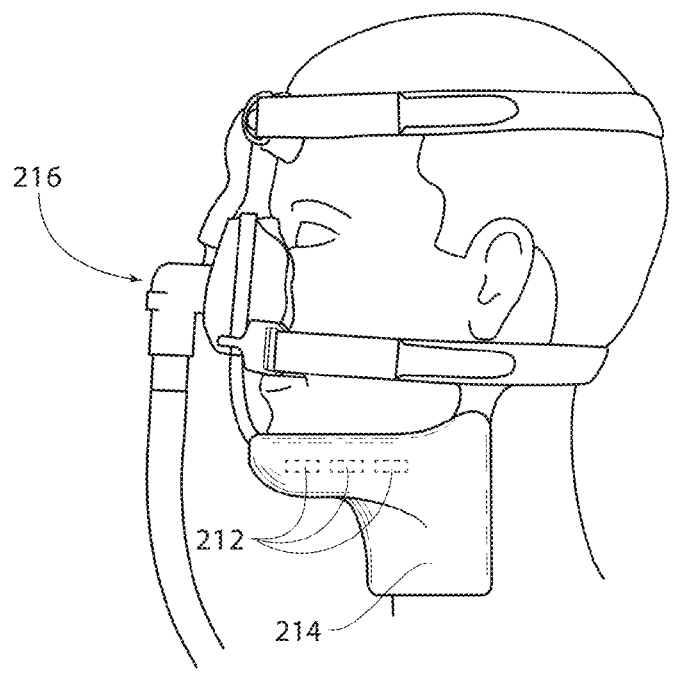
FIG. 19D is a side elevation view of the external carrier support shown in FIG. 19C, which magnetically interacts with the scaffold structure shown in FIG. 19A, and being further integrated with a CPAP mask.

In a representative arrangement, as shown in FIG. 19C, an external array of magnets 212 (e.g., on an external carrier structure 214) interact with the magnets 210 carried by the scaffold structure 138 (i.e., by magnetic attraction between magnets of different polarities) to preferentially condition the scaffold structure 138 to resist buckling of tissue structures in, on, or near the floor of the mouth in a cranial direction and/or to preferentially bias or brace muscles in the floor of the mouth tissue in a caudal direction, or otherwise cause a bending or elongation or stiffening or activation of the scaffold structure 138, to displace the floor of the mouth away from the oral cavity. As FIG. 19D shows, the external structure 214 can be integrated with a CPAP mask or headgear 216.

In this arrangement, as before described, the body of the scaffold structure 138 can, if desired, be preferably weakened (e.g., include areas of reduced thickness or slotted preferentially) or possess a spring constant, which preferentially bend the scaffold structure 138 in the desired caudal direction.

Figure 19E:
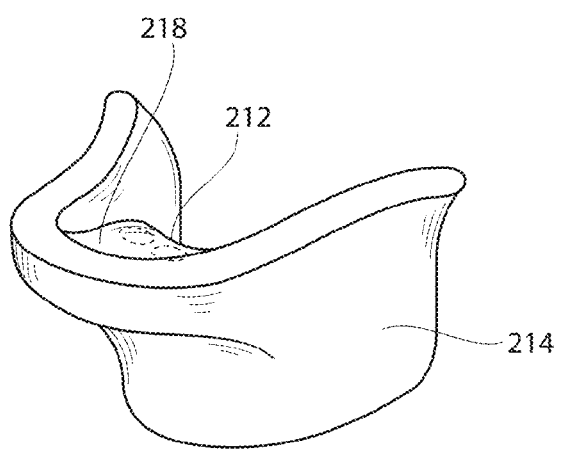
FIG. 19E is a side perspective view of the external carrier support shown in FIG. 19C, which magnetically interacts with the scaffold structure shown in FIG. 19A, and further showing the concave pocket region that receives tissue underlying the floor of the mouth during use.

The external carrier structure 214 (or any external structure that is intended to be placed into association with tissue structures in, on, or near the floor of the mouth) is sized and configured to not compress tissue structures in, on, or near the floor of the mouth to encourage tongue prolapse or to block the desirable lowering of the tongue and its beneficial effects upon the airway. External pressure upon the exterior of the chin under the floor of the mouth, such that the floor of the mouth is elevated or shifted in toward the larynx, is undesirable, as this, too, can interfere with the objective of resisting inward buckling of tissue structures in the oral cavity toward the top of the head. Furthermore, the length of any external structure 214 that is intended to be placed into association with tissue structures in, on, or near the floor of the mouth is desirably sized such that it does not press or push into the neck area near the hyoid bone/thyroid cartilage and larynx. For example, a given external structure 214 can include a concave pocket region 218 (see FIG. 19E), which receives tissue underlying the floor of the mouth as the scaffold structure 138 displaces structures in the floor of the mouth away from the oral cavity. As another example, a given external structure 214 that is intended to be placed into association with tissue structures in, on, or near the floor of the mouth can include, under the chin, one or more components that buckle outward (toward the feet) when the mandible opens. As another example, a given external structure 214 that is intended to be placed into association with tissue structures in, on, or near the floor of the mouth can include, under the chin, one or more sensors that monitor pressure changes and/or volume changes affecting tissue structures in, on, or near the floor of the mouth, coupled to a component that responds by minimizing these changes. In this way, the external carrier structure 214 does not compress the floor of the mouth to interfere with achievement of the desired therapeutic objectives, e.g., the effect that the scaffold structure 138 is intended to provide.

The array of magnets 212 on the external carrier structure 214 can comprise permanent magnets. Alternatively, the array of magnets 212 on the external carrier structure 214 can comprise electro-magnets, which can be selectively turned on when the desired therapeutic effect is desired (e.g., during sleep) and turned off when the effect is not desired (e.g., when the individual is awake). The activation of the electromagnets can be controlled by the individual, or can be activated in response to the detection of a sleep apnea event by an external or internal monitoring unit.

The magnets 210 carried by the scaffold structure 138 can comprise one or more electromagnets that can be selectively turned on when the desired therapeutic effect is desired (e.g., during sleep) and turned off when the effect is not desired (e.g., when the individual is awake). The incorporation of selectively activated electromagnets on the scaffold structure 138 makes possible the elimination use of an external carrier structure 214.

Figure 19F:
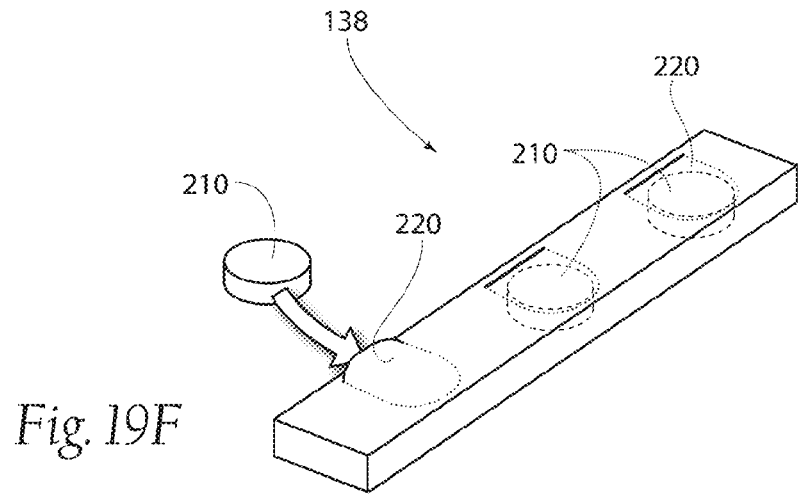
FIG. 19F/G/H are side perspective views of representative embodiments of scaffold structures like that shown in FIG. 19A, which include one or more magnets or ferrous materials that are releasably attached to the scaffold structures.
Figure 19G:
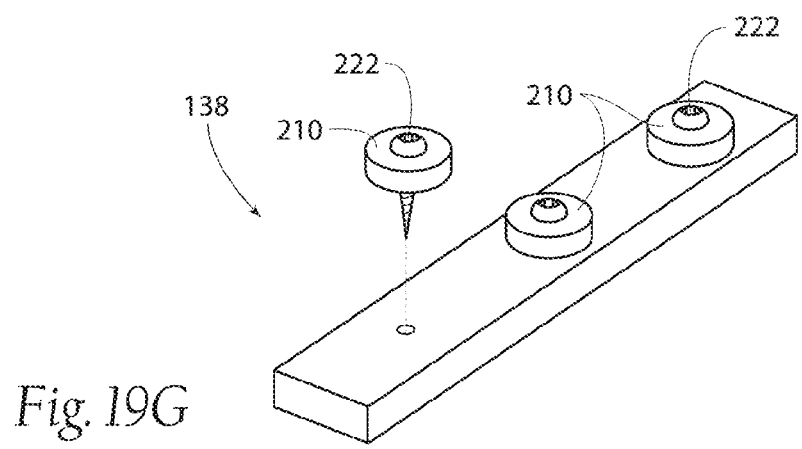
FIG. 19I is a plane view of a shaped scaffold structure comprising a rigid encapsulation of a magnet that is sized and configured to guide or float in, on, or near tissue structures in the floor of the mouth.
FIG. 19J is a plane view of a shaped scaffold structure comprising a rigid encapsulation of a magnet that is sized and configured to be connected to the hyoid bone, or mandible, or connective tissue near the hyoid bone or mandible.
FIG. 19K is a side perspective view of a trampoline scaffold structure, like that shown in FIG. 16, and further including one or more magnets or ferrous materials that are encapsulated in the structure.
FIG. 19L is a side perspective view of a trampoline scaffold structure, like that shown in FIG. 16, and further including one or more magnets or ferrous materials that are releasably attached to the structure.
FIG. 19M is an anatomic side section view of an oral cavity, pharynx, and larynx of an adult human, with the mouth closed, showing magnets carried by an oral appliance in the oral cavity magnetically interacting with the scaffold structure carrying magnets in, on, or near the floor of the mouth, the magnets on the oral appliance and the scaffold structure having the same polarity to exert a repelling magnetic force.
FIG. 19N is an anatomic side section view like that shown in FIG. 19M, with the addition of an external carrier support that carries magnets having the opposite polarity to the magnets carried by the scaffold structure to exert an attracting magnetic field, acting in tandem with the repelling magnetic force exerted between the magnets on the oral appliance and the magnets on the scaffold structure.
Figure 19H:
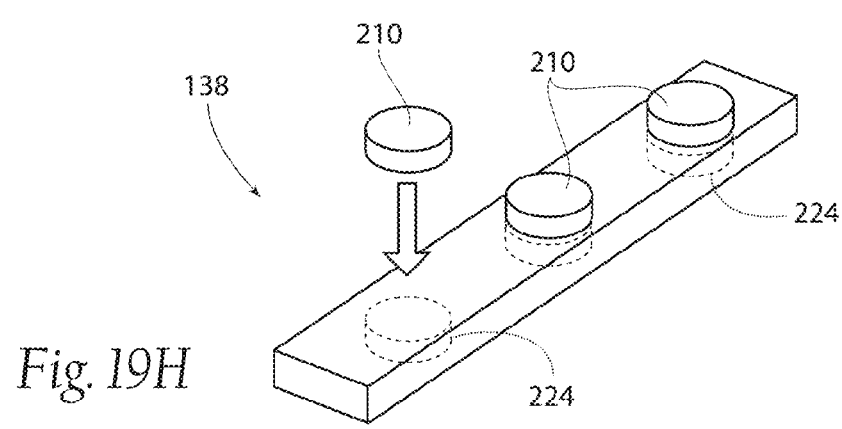

The magnets or ferrous materials 210 can be permanently integrated into, onto, or otherwise affixed to the material of the scaffold structure 138, as FIGS. 19A and 19B show. The magnets or ferrous materials 210 can also be sized and configured for releasable attachment to the material of the scaffold structure 138, as FIGS. 19F to 19H show. The releasable attachment of one or more magnets or ferrous materials 210 to a scaffold structure 138 allows removal of the magnets or ferrous materials when desired, e.g., for MRI. The releasable attachment of one or more magnets or ferrous materials 210 to a scaffold structure 138 also makes it possible to titrate the mechanical properties of the scaffold structure 138. For example, a scaffold structure 138 may be placed on a trial basis without magnets or ferrous materials 210 and its therapeutic effects observed. If enhancement or titration is desired, magnets or ferrous materials 210 can be added until the desired therapeutic effects are achieved.

For example, the one or more magnets or ferrous materials 210 can be releasably fitted into pocket(s) 220 (see FIG. 19F) formed in the body of the scaffold structure 138. Or, the one or more magnets or ferrous materials 210 can be releasably attached by screws or fasteners 222 (see FIG. 19G) to the body of the scaffold structure 138. In these arrangements, the scaffold structure 138 is desirably made from a non-ferrous material. However, the body of the scaffold structure 138 can include a ferrous material 224 (see FIG. 19H), and can carry one or more magnets 210 that possess an opposite magnetic polarity, so that the magnets are releasably attached to the scaffold structure 138 by magnetic attraction.

Figure 19I:
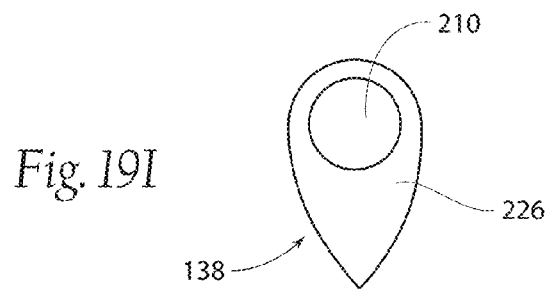

The scaffold structure 138 can comprise a rigid encapsulation 226 of a relatively small magnet 210 (see FIG. 19I). In this arrangement, the scaffold structure 138 can be spherical (ball shaped), or it may be shaped like a tear drop, or like a disk. The surface of the structure 138 is desirably smooth and its overall geometry rounded to allow it to glide or float in tissue. Its position can thereby adjust to external influences. The small, rigid magnetic scaffold structure 138 is not secured to surrounding muscle and tissue comprising the floor of the mouth. It is thereby able to move or "glide" in the adjacent region of tissue and muscle of the floor of the mouth in response to the externally applied magnetic forces. This also allows the scaffold structure 138 to be located and/or moved to the tissue region that is most unstable.

Figure 19J:
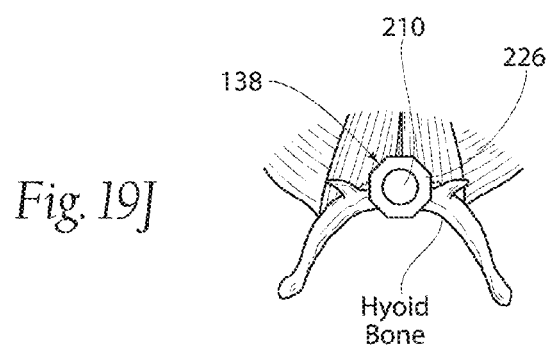

Alternatively, the small, rigid magnetic scaffold structure 138 can be sized and configured so that it does not move by the incorporation of rigid extensions or rectilinear or curvilinear geometries (see FIG. 19J). Such immobile magnetic scaffold structure(s) 138 can be connected to the hyoid bone or mandible or connective tissue near the hyoid bone, or mandible.

Figure 19K:
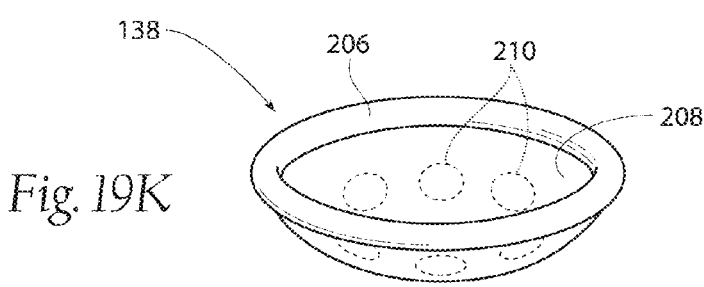
Figure 19L:
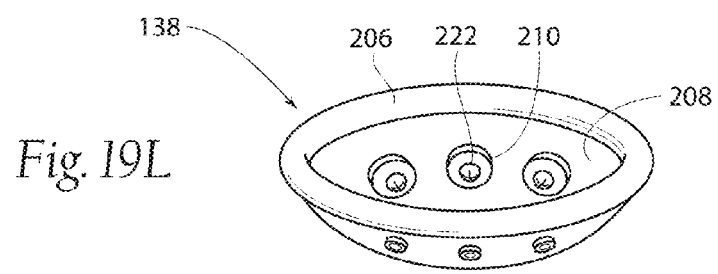

Alternatively, the magnetic scaffold structure 138 can mimic the structure of the floor of the mouth, comprising a resilient, trampoline-like structure 206/208, as previously described, and as shown in FIG. 19K. In this arrangement, one or more magnets or ferrous materials 210 can be permanently incorporated throughout the trampoline-like structure 138 (see FIG. 19K), e.g., ferromagnetic material suspended in silicone. Magnetic interaction with one or more opposite polarity magnets 212 externally carried by the external carrier structure 214 (like that shown in FIG. 19D) attracts the magnets or ferrous materials 210, thereby drawing the flexible webbing or mesh material 208 of the structure 138 in the desired caudal direction, to affect the desired therapeutic effect in the floor of the mouth. The one or more magnets or ferrous materials 210 can carried in pockets or secured by screws or fasteners 222 (see FIG. 19L), for releasable attachment to the trampoline-like structure 138.

Figure 19M:
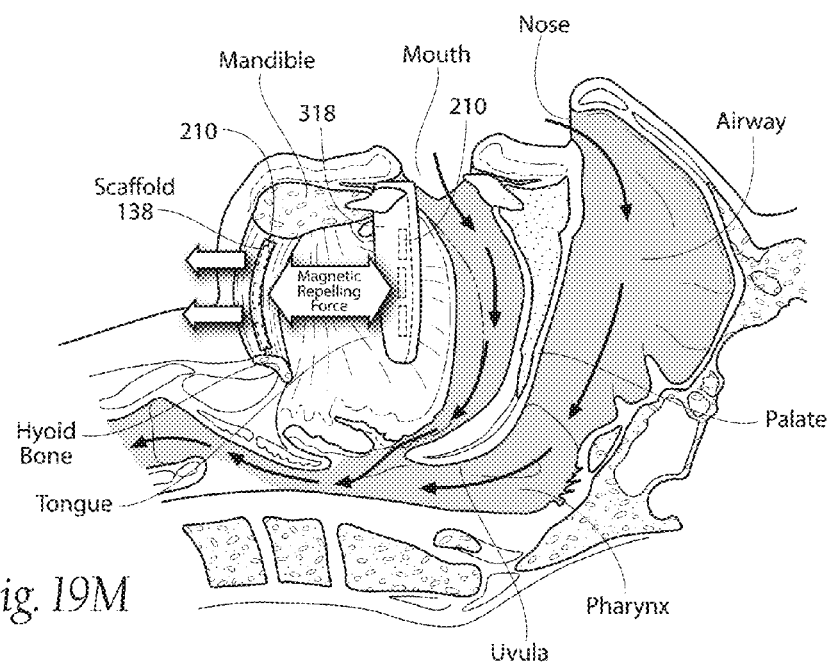
Figure 19N:
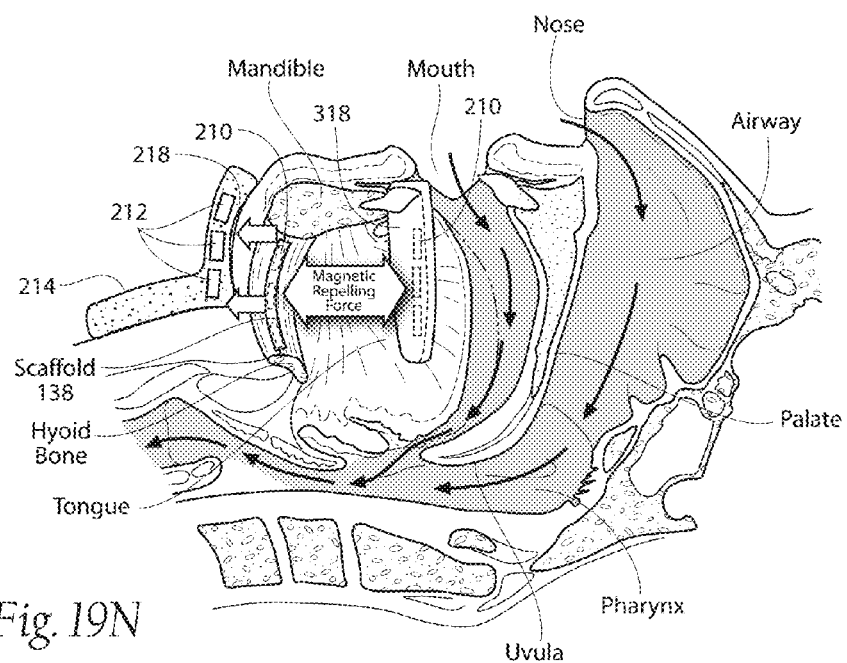

Magnets or magnetic structures implanted in, on, or near the floor of the mouth can also interact with magnets 210 carried by an oral appliance 318 fitted to teeth on the upper or lower mandible (see FIG. 19M). In this arrangement, an array of magnets 210 on the oral appliance 318 interact with the magnetically actuated scaffold structure 138 implanted in, on, or near the floor of the mouth (i.e., by magnetic repelling between magnets of the same polarity) to preferentially condition the magnetically actuated structure 138 to resist buckling of tissue structures in, on, or near the floor of the mouth in a cranial direction and/or to preferentially bias or brace muscles in the floor of the mouth tissue in a caudal direction, or otherwise cause a bending or elongation or stiffening or activation of the magnetically actuated structure 138, to displace the floor of the mouth away from the oral cavity. As FIG. 19N shows, the beneficial effect of locating magnetic repelling arrays inside the oral cavity can be complemented by the simultaneous placement of a magnetic attracting array 212 carried on an external carrier structure 214.

9. Leaf Spring Mounted Scaffold Structures

Figure 20A:
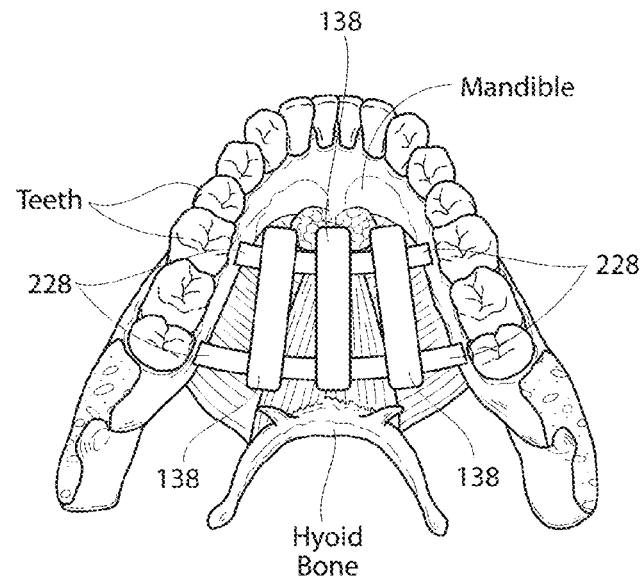
FIGS. 20A and 20B are anatomic superior views of the floor of the mouth showing the implantation of scaffold structures that include flexible leaf-spring regions.
Figure 20B:
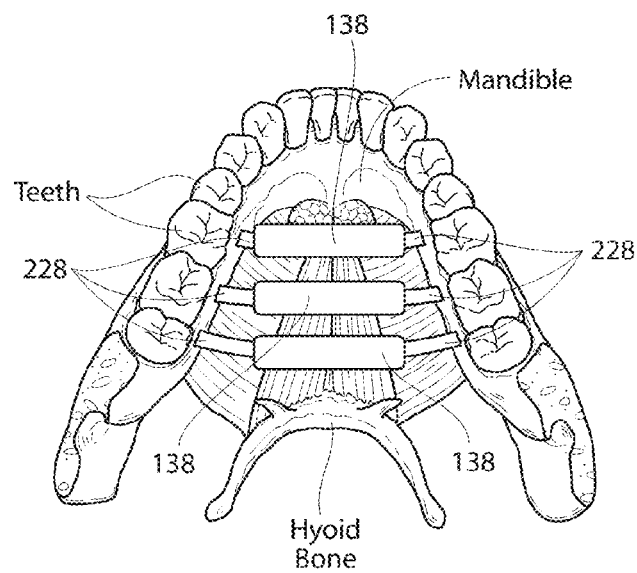

As shown in FIGS. 20A and 20B, the scaffold structure 138 can include flexible leaf spring regions 228 anchored to the lateral aspects of the mandible and, if desired, to the hyoid bone. FIG. 20A shows the mounting by leaf-springs 228 of anterior-to-posterior scaffold structures 138. FIG. 20B shows mounting by leaf-springs 228 of lateral scaffold structures 138.

The leaf spring regions 228 provide flexibility to the scaffold structure 138 and can also provide resistance to buckling of tissue structures in, on, or near the floor of the mouth in a cranial direction and/or to preferentially bend or bias the scaffold structure 138 in a caudal direction, to direct tissue regions in the floor of the mouth toward the feet and away from the airway.

The leaf spring regions 228 can be made of a shape activated material or incorporate a component that is activated by mechanical, thermal, electrical, and/or magnetic energy, so that they can be placed into tension in response to the application of energy (e.g., at night) and selectively relaxed when tension is not required (e.g., during the day). For example, the leaf spring regions 228 can themselves carry magnets that interact with magnets carried by an oral appliance fitted to teeth on the upper or lower mandible (in the manner shown in FIG. 19M). In this arrangement, an array of magnets on the oral appliance interact with the magnets on the leaf springs (i.e., by magnetic repelling between magnets of the same polarity) to preferentially condition the leaf spring regions 228 to resist buckling of tissue structures in, on, or near the floor of the mouth in a cranial direction and/or to preferentially bias or brace muscles in the floor of the mouth tissue in a caudal direction. Alternatively, or in combination, the leaf spring regions 228 can carry magnets that interact with a magnetic attracting array carried on an external carrier structure.

10. Fiber Scaffold Structures

The scaffold structure 138 can incorporate twisted or braided fibers, which are sized and configured to be implanted in one or more tissue structures in, on, or near the floor of the mouth. A single type fiber could be used, or the scaffold structure 138 can comprise two different fibers braided or twisted together. One fiber may be selected to encourage a fibrotic response, e.g., polyester or silk suture material, or a polyurethane-polyurea copolymer such as "Spandex" or "Elastane" or "Lycra" or "Elaspan" or "Creora" or "ROICA" or "Dorlastan" or "Linel" or "ESPA". A fiber may be selected to be bio-resorbable, e.g., collagen or synthetic materials such as the PDS suture material. Alternatively, a fiber may be selected that is non-resorbable, polypropylene suture material. The twisted or braided fiber structure stiffens and/or shapes the tissue structures in, on, or near the floor of the mouth into which it is implanted, either due to the mechanical properties of the fiber(s) or due to a fibrotic response, or both. The fibers may be bonded together along the axial length of the scaffold structure to provide added stiffness.

C. Representative Placement in Selected Tissue Regions in, on, or Near the Floor of the Mouth Representative embodiments will now be described for the sake of illustration and not limitation.

1. Between Mylohyoid and Geniohyoid Muscles FIGS. 7 A/B/C, 13 A

In one representative embodiment (shown in FIGS. 7A/B/C and FIG. 13A), the scaffold structure 138 is placed between a mylohyoid muscle and a geniohyoid muscle in, on, or near the floor of the mouth. Both suprahyoid muscles originate at the mandible and are inserted in the hyoid bone.

The mylohyoid serves to elevate the hyoid bone, the floor of the mouth, and tongue during swallowing and speaking.

The geniohyoid serves to pull the hyoid bone anterosuperiorly (forward and up), shorten the floor of the mouth, and widen the pharynx.

Placement of a scaffold structure 138 between these two suprahyoid muscles in, on, or near the floor of the mouth provides mechanical support within the tissue region that resists the formation of undesired physiologic conditions in the floor of the mouth caused by a diminution or absence of the native activities of these suprahyoid muscles during sleep. The scaffold structure 138 can be placed an anterior-to-posterior orientation, or in a lateral orientation.

When placed in an anterior-to-posterior orientation, the size and alignment of the scaffold structure 138 relative to the hyoid bone is important. Desirably, the anterior-to-posterior (A-P) dimension of the scaffold structure 138 should be less than the distance between the hyoid bone and the mandible. The scaffold structure 138 should span between the hyoid bone and the mandible without tension, so as not to limit flexure of the neck or produce a significant posterior force on the hyoid bone. Comparable considerations apply when the scaffold structure 138 is oriented laterally across the mandible or adjacent to the hyoid bone.

Further, it is generally desirable that the posterior region of an A-P scaffold structure 138 or a lateral scaffold structure 138 adjacent the hyoid bone rests generally in alignment next to the hyoid bone and in the plane of the hyoid bone. It is generally desirable that the posterior end of the scaffold structure 138 is aligned with the hyoid bone and the axis of the scaffold structure 138 extends between the mandible and hyoid to ensure that the scaffold structure 138 is fully engaged with the tissue at, near, or in the floor of the mouth, and also so that the scaffold structure 138 may restrict posterior motion of the mandible and/or stabilize the hyoid bone. In these situations, it is undesirable that the entire posterior region of the scaffold structure 138 aligns below the plane of (i.e., under or below) the hyoid bone. This can occur if the scaffold structure 138 is sized too large, or if the thickness or strength of the muscles in which the scaffold structure 138 is implanted vary or are weak or weaken. Improper placement or migration of the posterior region of the scaffold structure 138 out of the proper close, in-plane alignment with the hyoid bone, to a location under or below the hyoid bone, interferes with achieving the desired therapeutic effect that the scaffold structure 138 is intended to provide.

In other situations, however, it may be acceptable and even desirable that the posterior edge of the scaffold structure is partially or fully inferior to the hyoid bone. In one specific embodiment, the posterior end of the scaffold structure 138 is attached to the thyroid cartilage and under tension. In this case, the scaffold structure 138 is engaged with a portion of tissue in, on, or near the floor of the mouth, and the attachment to the cartilage pulls the posterior end of the scaffold structure 138 inferiorly, causing outward displacement of the floor of the mouth tissue (and an increase in oral cavity volume), resulting in the posterior end of the scaffold structure 138 aligning inferiorly to the hyoid bone. It may be desirable to place this attachment after a period of time has passed after implantation of the scaffold structure 138. This allows the tissue surrounding the scaffold structure 138 to integrate with and stabilize around the scaffold structure 138 prior to attaching to the cartilage and applying inferior tension.

When properly placed in the desired ordination between the mylohyoid muscle and a geniohyoid muscle in, on, or near the floor of the mouth, the scaffold structure 138 provides mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold structure 138 and muscles can also serve to stabilize a desirable tissue orientation affected by the mylohyoid muscle, which is favorable to maintaining an open airway. The mechanical support of the scaffold structure 138 thereby resists formation of a contrary tissue orientation when the muscles relax during sleep, contrary gravity conditions exist, and/or the mouth opens, characterized by a lack of resistance to a posterior dropping of the floor of the mouth and the tongue, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, would otherwise arise due to a diminution or absence of the native activity or the mylohyoid during sleep. By resisting this contrary tissue orientation, the scaffold structure 138 resists a narrowing or obstruction of the pharyngeal airway and resulting apneic episode.

When placed between a mylohyoid muscle and a geniohyoid muscle in, on, or near the floor of the mouth, the interaction between the scaffold structure 138 and muscles can also provide mechanical support to tissue in, on, or near the floor of the mouth that stabilizes a desirable tissue orientation affected by the geniohyoid muscle, which is favorable to maintaining an open pharyngeal airway. The mechanical support of the scaffold structure 138 thereby resists formation of a contrary tissue orientation, when the muscles relax during sleep, contrary gravity conditions exist, and/or the mouth opens, characterized by a lack of resistance to movement of the hyoid bone posteriorly and inferiorly (backward and down), widening the floor of the mouth, and narrowing the pharynx, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, could otherwise arise due to a diminution or absence of the native activity or the geniohyoid during sleep. By resisting this other contrary tissue orientation, the scaffold structure 138 further resists a narrowing or obstruction of the pharyngeal airway and resulting apneic episode.

Figure 28A:
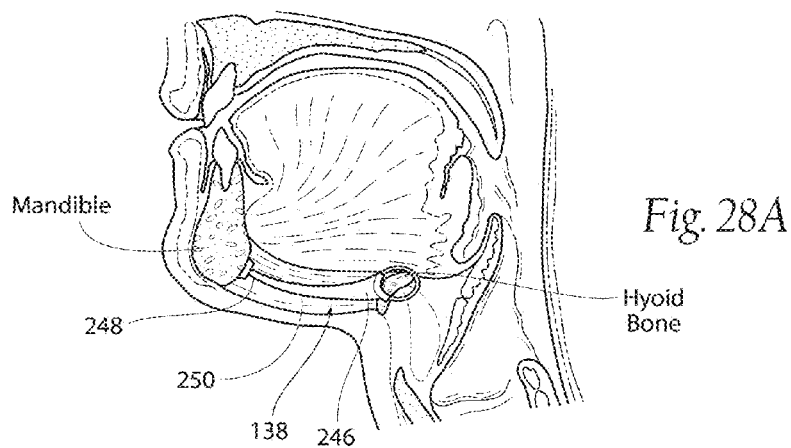
FIG. 28A is an anatomic view of an oral cavity, pharynx, and larynx of an adult human, with the mouth closed, showing a representative embodiment of a system comprising a scaffold structure implanted in, or, or near the floor of the mouth and further coupled to the hyoid bone and mandible to achieve hyoid bone stabilization (anterior), the scaffold structure further including variable regions of stiffness ranging from greater stiffness to less stiffness in an anterior to posterior direction from the mandible to the hyoid bone.

The scaffold structure 138 may be implanted in muscles tissue in the floor of the mouth without attachment to the rigid structures of the mandible and/or hyoid bone. Alternatively, the scaffold structure 138 may be attached to one or both of these rigid bone structures, e.g., by screws, suture, clamping, or elastic materials, as will be described in greater detail later. A representative embodiment of a scaffold structure 138 fixed to both the mandible and hyoid bone is shown in FIG. 28A. By attaching the ends of a flexible scaffold structure 138 to rigid structures, the shape of the implant can be influenced. As shown in FIG. 28A, the flexible scaffold structure 138 can be fixed with preferential bend, to resist buckling of tissue structures in, on, or near the floor of the mouth in a cranial direction and/or to preferentially bias the scaffold structure 138 in a caudal direction to establish a counter force that directs the tissue structures out of the airway, drawing the hyoid bone forward. Alternatively, the flexible scaffold structure 138 can be activated by an energy source, e.g., mechanical and/or electrical and/or thermal energy and/or magnetic interaction or the like, to assume the outward bend or to stiffen upon demand. The connection point between the scaffold structure 138 and the rigid bone structure or structures can include a hinge or a spring-loaded hinge to enhance the tissue shaping functions of the scaffold structure 138, as shown in FIGS. 49 A/B.

2. Between Geniohyoid and Genioglossus Muscles

Figure 21:
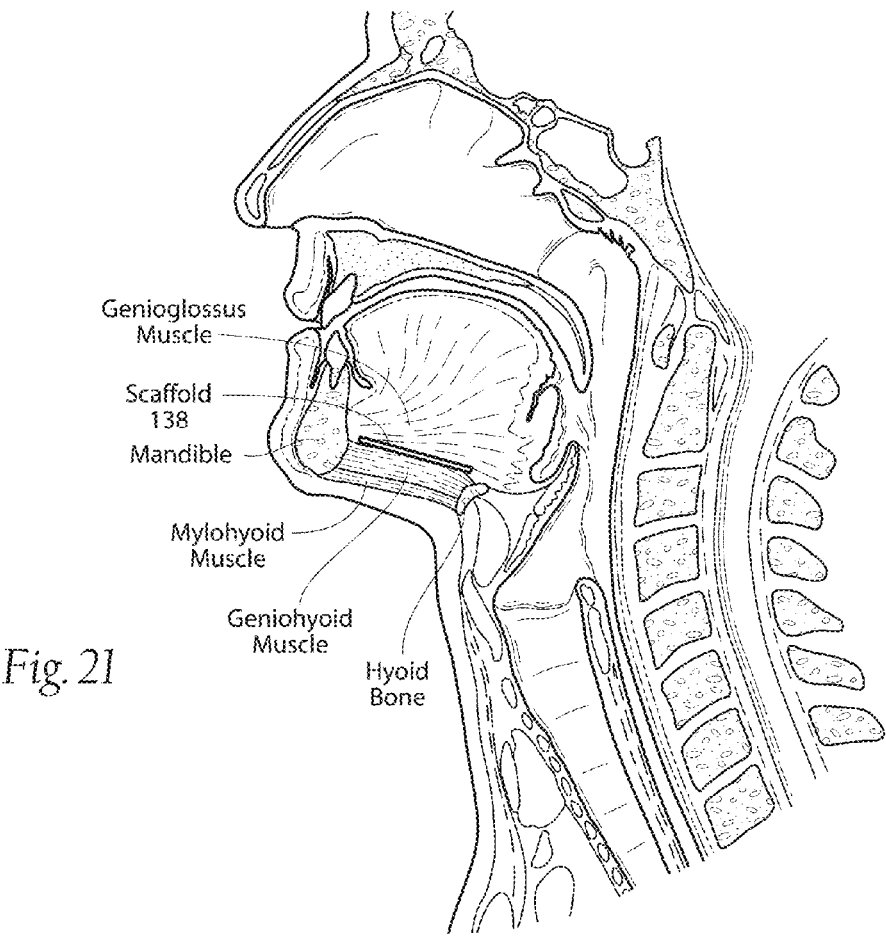
FIGS. 21 and 22 are, respectively anatomic views of an oral cavity, pharynx, and larynx of an adult human, with the mouth closed (FIG. 21) and an inferior view of the floor of the mouth (FIG. 22), showing the presence of a scaffold structure implanted between the geniohyoid and genioglossus muscles.

In another representative embodiment (shown in FIG. 21), the scaffold structure 138 is placed between a geniohyoid muscle and the genioglossus muscle (and not substantially within the genioglossus muscle itself) in, on, or near the floor of the mouth. The scaffold structure 138 can be placed an anterior-to-posterior orientation, or in a lateral orientation.

The geniohyoid muscle is a suprahyoid muscle that originates at the mandible and is inserted in the hyoid bone. The geniohyoid muscle serves to pull the hyoid bone anterosuperiorly (forward and up), shorten the floor of the mouth, and widen the pharynx.

The genioglossus muscle originates at the superior part of the mental spine of the mandible and is inserted in the dorsum of the tongue as well as the body of the hydroid bone. The genioglossus muscle serves pull the tongue anteriorly for protrusion.

Placement of a scaffold structure 138 between the genioglossus muscle (which inserts into the hyoid bone) and a suprahyoid muscle (which also inserts into the hyoid bone) (and not substantially within the genioglossus muscle itself) provides mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold structure 138 and muscles can also serve to resist the formation of undesired physiologic conditions in the floor of the mouth caused by a diminution or absence of the native activities of these muscles during sleep.

For example, when placed between a geniohyoid muscle and the genioglossus muscle in, on, or near the floor of the mouth, the scaffold structure 138 can provide mechanical support to tissue in, on, or near the floor of the mouth that stabilizes a desirable tissue orientation affected by the geniohyoid muscle, which is favorable to maintaining an open pharyngeal airway. The mechanical support of the scaffold structure 138 thereby resists formation of a contrary tissue orientation, when the muscles relax during sleep, contrary gravity conditions exist, and/or the mouth opens, characterized by a lack of resistance to movement of the hyoid bone posteriorly and inferiorly (backward and down), widening the floor of the mouth, and narrowing the pharynx, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, would otherwise arise due to a diminution or absence of the native activity or the geniohyoid during sleep. By resisting this contrary tissue orientation, the scaffold structure 138 resists a narrowing or obstruction of the pharyngeal airway and resulting apneic episode.

Furthermore, when placed between the geniohyoid muscle and the genioglossus muscle in, on, or near the floor of the mouth, the scaffold structure 138 provides mechanical support to tissue in the floor of the mouth that stabilizes a desirable tissue orientation affected by the genioglossus muscle, which is favorable to maintaining an open pharyngeal airway. The mechanical support of the scaffold structure 138 thereby resists formation of a contrary tissue orientation, when the muscles relax during sleep, contrary gravity conditions exist, and/or the mouth opens, characterized by a lack of resistance to posterior movement of the tongue, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, could otherwise arise due to a diminution or absence of the native activity or the genioglossus during sleep. By resisting this contrary tissue orientation, the scaffold structure 138 resists a narrowing or obstruction of the pharyngeal airway and resulting apneic episode.

As before explained, the scaffold structure 138, if desired, may be attached to one or both of the rigid bone structures of the mandible and hyoid bone, e.g., by screws, suture, clamping, or elastic materials, as will be described in greater detail later. By attaching the ends of a flexible scaffold structure 138 to rigid structures, the shape of the implant can be influenced. As shown in FIG. 7D, the flexible scaffold structure 138 can be stiffened or shaped to resist buckling of tissue structures in, on, or near the floor of the mouth in a cranial direction and/or possess a preferential bend to preferentially bias the scaffold structure 138 in a caudal direction to establish a counter force that directs the tissue structures out of the airway, drawing the hyoid bone forward. Alternatively, the flexible scaffold structure 138 can be activated by an energy source, e.g., mechanical and/or electrical and/or thermal energy and/or magnetic interaction or the like, to assume the outward bend or to stiffen upon demand. The connection point between the scaffold structure 138 and the rigid bone structure or structures can include a hinge or a spring-loaded hinge 268 to enhance the tissue shaping functions of the scaffold structure 138, as shown in FIGS. 49 A/B.

3. Between Digastric and Mylohyoid Muscles

Figure 22:
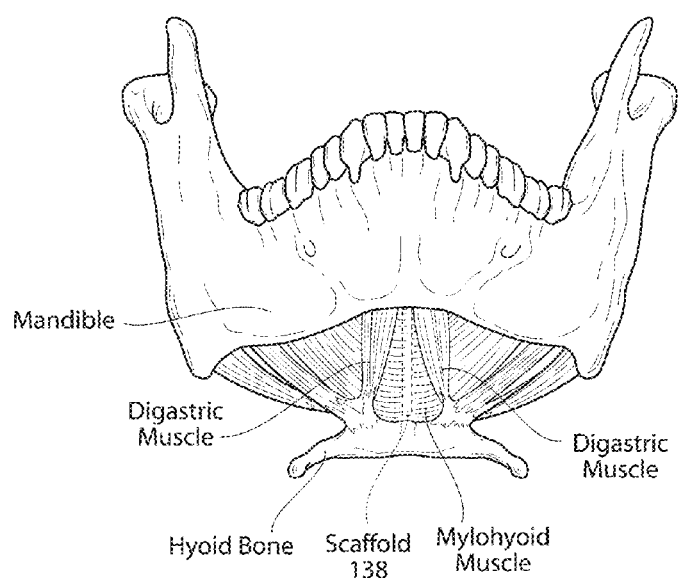

In another representative embodiment (shown in FIG. 22), the scaffold structure 138 is placed between a digastric muscle and a mylohyoid muscle in, on, or near the floor of the mouth. Both are suprahyoid muscles that originates at the mandible and is inserted in the hyoid bone. The scaffold structure can be placed in an anterior-to-posterior orientation, or in a lateral orientation.

The digastric muscle serves to depress (close) the mandible and raise the hyoid bone during swallowing and speaking.

The mylohyoid serves to elevate the hyoid bone, the floor of the mouth, and tongue during swallowing and speaking.

For example, when placed between the suprahyoid digastric and mylohyoid muscles, the scaffold structure 138 can provide mechanical support to tissue structures in, on, or near the floor of the mouth that resists collapse of these tissue structures into the airway when the muscles relax during sleep, contrary gravity conditions exist, and/or the mouth opens.

Further, the interaction between the scaffold structure 138 and muscles can also serve to resist the formation of undesired physiologic conditions in the floor of the mouth caused by a diminution or absence of the native activities of these muscles during sleep.

For example, when placed between a digastric muscle and a mylohyoid muscle in, on, or near the floor of the mouth, the scaffold structure 138 provides mechanical support to tissue in, on, or near the floor of the mouth that stabilizes a desirable tissue orientation affected by the digastric muscle, which is favorable to maintaining an open pharyngeal airway. The mechanical support of the scaffold structure 138 thereby resists formation of a contrary tissue orientation, when the muscles relax during sleep, contrary gravity conditions exist, and/or the mouth opens, characterized by a lack of resistance to the depression (closing) of the mandible, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, would otherwise arise due to a diminution or absence of the native activity or the digastric during sleep. By resisting this contrary tissue orientation, the scaffold structure 138 resists a narrowing or obstruction of the pharyngeal airway and resulting apneic episode.

Furthermore, when placed between the digastric muscle and the mylohyoid muscle in, on, or near the floor of the mouth, the scaffold structure 138 provides mechanical support to tissue in the floor of the mouth that stabilizes a desirable tissue orientation affected by the mylohyoid muscle, which is favorable to maintaining an open pharyngeal airway. The mechanical support of the scaffold structure 138 thereby resists formation of a contrary tissue orientation, when the muscles relax during sleep, contrary gravity conditions exist, and/or the mouth opens, characterized by a lack of resistance to a dropping of the floor of the mouth and the tongue, which is not favorable to maintaining an open pharyngeal airway and which, instead, leads to a narrowing or obstruction of the pharyngeal airway. The mechanical support of the scaffold structure 138 moderates the undesirable physiologic conditions that, in the absence of the scaffold structure 138, would otherwise arise due to a diminution or absence of the native activity or the mylohyoid during sleep. By resisting this contrary tissue orientation, the scaffold structure 138 resists a narrowing or obstruction of the pharyngeal airway and resulting apneic episode.

As before explained, the scaffold structure 138, if desired, may be attached to one or both of the rigid bone structures of the mandible and hyoid bone, e.g., by screws, suture, clamping, or elastic materials, as will be described in greater detail later. By attaching the ends of a flexible scaffold structure 138 to rigid structures, the shape of the implant can be influenced. As shown in FIG. 7D, the flexible scaffold structure 138 can be stiffened or shaped to resist buckling of tissue structures in, on, or near the floor of the mouth in a cranial direction and/or to possess a preferentially bend to bias the scaffold structure 138 in a caudal direction to establish a counter force that directs the tissue structures out of the airway, drawing the hyoid bone forward. Alternatively, the flexible scaffold structure 138 can be activated by an energy source, e.g., mechanical and/or electrical and/or thermal energy and/or magnetic interaction or the like, to assume the outward bend or to stiffen upon demand. The connection point between the scaffold structure 138 and the rigid bone structure or structures can include a hinge or a spring-loaded hinge 228 to enhance the tissue shaping functions of the scaffold structure 138, as shown in FIGS. 49 A/B.

D. Representative Implantation Methods/Systems

A representative method for implanting a scaffold structure 138 like that shown in FIG. 7B includes making a transverse superficial incision under the chin, desirably along the natural chin fold. The method includes cutting platysma muscle to provide access to the mylohoid muscle. Access to the mylohoid muscle can be obtained between the two digastrics muscles, which do not need to be cut. The method includes cutting and dissecting the mylohyoid muscle between the digastric muscles to gain access to the targeted muscle plane.

The method includes placing the scaffold structure 138 in this plane so that the thin dimension of the scaffold structure 138 is in the superior/inferior direction, with the length and width of the scaffold structure 138 extending in the lateral as well as anterior/posterior directions.

The method can optionally suturing the implant to surrounding tissue as desired for stabilization. As before explained, the scaffold structure 138, if desired, may be attached to one or both of the rigid bone structures of the mandible and hyoid bone, e.g., by screws, suture, clamping, or elastic materials, as will be described in greater detail later. The most desired location for suturing is around the hyoid bone or to the connective tissue attached to the hyoid bone. It is desirable that the manner of attachment itself not be overly rigid, but flexible enough to accommodate the dynamic flexure of muscles that occurs in the floor of the mouth. Besides suturing, mechanical or elastic fasteners, e.g., springs; coils; elastic bands; synthetic fibers having elasticity, e.g., a polyurethane-polyurea copolymer such as "Spandex" or "Elastane" or "Lycra" or "Elaspan" or "Creora" or "ROICA" or "Dorlastan" or "Linel" or "ESPA"; screws, staples, C-clamps, rings (permitting rotation but limiting linear motion), or the like, which can be quickly secured in a minimally invasive manner, can be desirably used. The flexible attachment materials can be surface treated (e.g., ePTFE encapsulation) to limit fibrotic encapsulation to maintain tissue flexibility around them. The manner of attachment can comprise a combination of a mechanical fastener coupled to bone (e.g., the hyoid bone) and a flexible link coupling the mechanical fastener to the scaffold structure 138. The scaffold structure 138 body may have an extension into the genioglossus or next superior or inferior muscle planes for additional stabilization of the scaffold structure 138 body, as well as provide stabilization for the genioglossus or the next superior or inferior muscle planes themselves. Other attachment methods include lateral and/or anterior and/or posterior extensions that engage connective tissue near the mandible or hyoid bone. These extensions may extend under the mandible, for example, to provide stabilization as well as further restriction of movement of tissue toward the airway. As above described, these extensions may include elastic or spring-like properties to further orient the tissue structures in the floor of the mouth in a caudal direction. The extensions themselves may be connected to connective tissue or bone by sutures of any of the attachment methods described herein.

The method includes suturing the targeted muscle plane closed, and then closing the superficial skin incision.

IV. Hyoid Bone Stabilization

A. Overview

As shown in FIGS. 3C, 3E, and 3F, the muscles in the floor of the floor of the mouth occupy a generally triangular-shaped area bounded by the hyoid bone and the front and sides of the mandible. The geometric center of this region (i.e., its centroid) lays adjacent to the hyoid bone. As before described, the most unstable tissue region in the floor of the mouth is often at or near the centroid of the floor of the mouth, which, relative to the distance between the hyoid bone and the mandible, is closer to the hyoid bone than it is to the mandible (that is, relative to the midpoint of the distance between the hyoid bone and the mandible, the region of instability is between the hyoid bone and the midpoint and not between the midpoint and the mandible). Contributing to this instability in this region is the rotation of the weight of the tongue about the hyoid bone in the supine position, and the anatomic consideration that tissue spreads out and is less dense near the midline of the hyoid bone than it is near the anterior mandible. For these reasons, efforts to stabilize tissue in, at, or near the floor of the mouth should not neglect supporting tissue structures at or near the hyoid bone, as well as supporting and stabilizing the hyoid bone itself. Scaffold structures in the floor of the mouth that take this consideration into account have been disclosed, e.g., in FIGS. 12E; 18A, and 18B.

B. Representative Embodiments

1. Hyoid Bone Stabilization (Caudal)

Figure 23A:
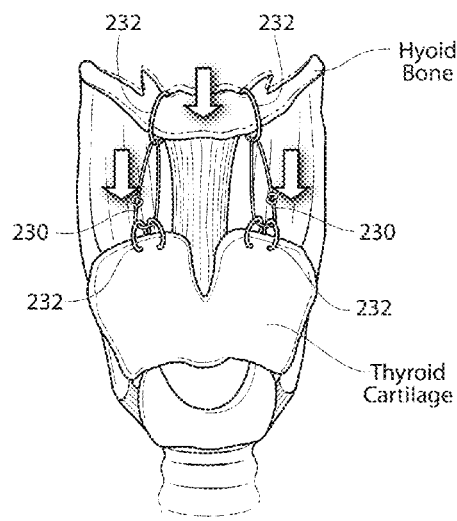
FIGS. 23A, 23B, 24A, and 24B are anterior anatomic views of the hyoid bone, pharynx, larynx, and thyroid cartilage of an adult human, showing representative embodiments of hyoid bone stabilization (caudal) systems.
Figure 23B:
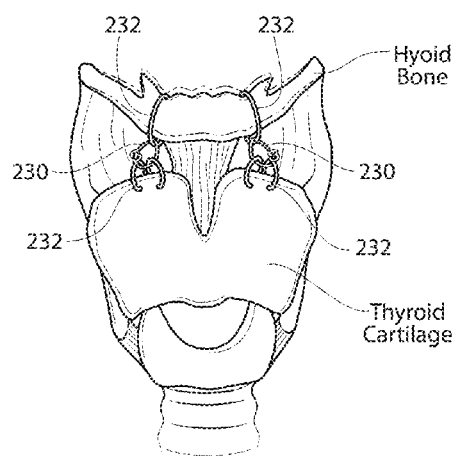
Figure 24A:
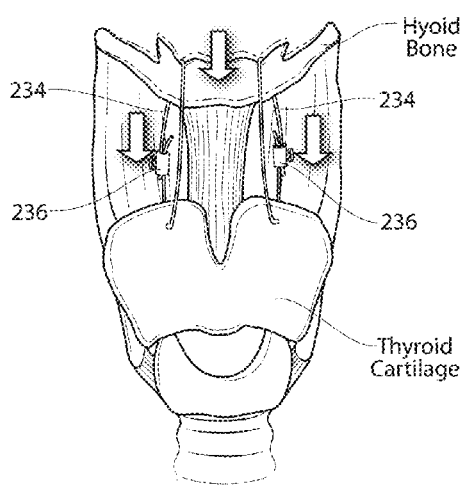
Figure 24B:
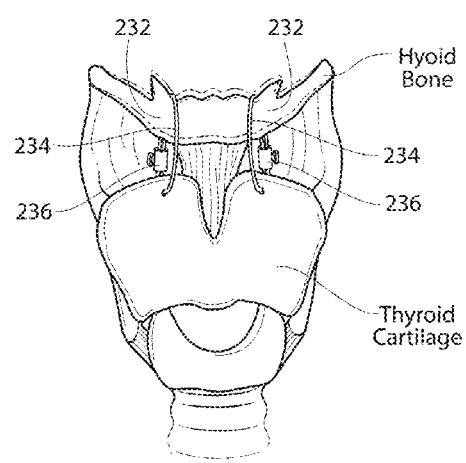

Either undertaken alone or in combination with the implantation of a scaffold structure 138 in, on, or near the floor of the mouth, posterior movement of the hyoid bone can be diminished or prevented by suturing the hyoid bone to the thyroid cartilage or surrounding connective tissue (see FIGS. 23A/B and 24A/B, which, in shorthand, will be called hyoid bone stabilization (caudal). Hyoid bone stabilization (caudal) pulls or pivots the hyoid bone toward the thyroid cartilage (as indicated by the arrows in FIGS. 23A and 24A), and, if desired, can pull the hyoid bone into substantially the same plane as the thyroid cartilage (as shown in FIGS. 23B and 24B), to provide stabilization for the hyoid bone. Hyoid bone stabilization (caudal) also pulls the tongue base in an anterior (forward) direction, which also is beneficial to keeping the airway open.

As shown in FIGS. 23A/B, the effects of hyoid bone stabilization (caudal) can be enhanced by the use of attachments 230 between the hyoid bone and inferior and/or anterior tissue structures, such as the thyroid cartilage, with or without the placement of a scaffold structure 138 in, on, or near the floor of the mouth. The attachments 230 can be rigid, but are more preferably flexible, and most preferably flexible and elastic. As shown in FIGS. 23A/B, flexible and elastic materials 230 such as springs; coils; elastic bands; synthetic fibers having elasticity, e.g., a polyurethane-polyurea copolymer such as "Spandex" or "Elastane" or "Lycra" or "Elaspan" or "Creora" or "ROICA" or "Dorlastan" or "Linel" or "ESPA" can form flexible and elastic linkages between the hyoid bone and the thyroid cartilage. As also shown in FIGS. 23A/B, the flexible and elastic material 230 can be coupled to the hyoid bone and the thyroid cartilage by rigid rings 232, which permit rotation but limit linear motion. These linkages 230/232 can be quickly secured in a minimally invasive manner. The linkage materials 230/232 can be surface treated (e.g., ePTFE encapsulation) to limit fibrotic encapsulation to maintain tissue flexibility around them.

Alternatively, or in combination, the effects of hyoid bone stabilization (caudal) can be enhanced by the use of flexible but not elastic, non-fatiguing metal or plastic materials 234, such as wire rope or braided wire to link the hyoid bone to the thyroid cartilage. Crimping mechanisms 236, like the screw mechanism shown in FIGS. 23A/B, can be used to secure the ends of the wire or braided rope materials together. These materials 234/236 provide tensile strength but resist fatigue and breaking during use.

Alternatively, a form of hyoid bone stabilization (caudal) can be achieved by surgically cutting the center region of the hyoid bone and rotating it forward and down, and then reattaching to the lateral portions of the hyoid bone. This serves to realign musculature in the floor of the mouth, twisting tissue in the floor of the mouth and genioglossus downward. The hyoid bone treated in this manner can, if desired, additionally attached to the thyroid cartilage.

Figure 25A:
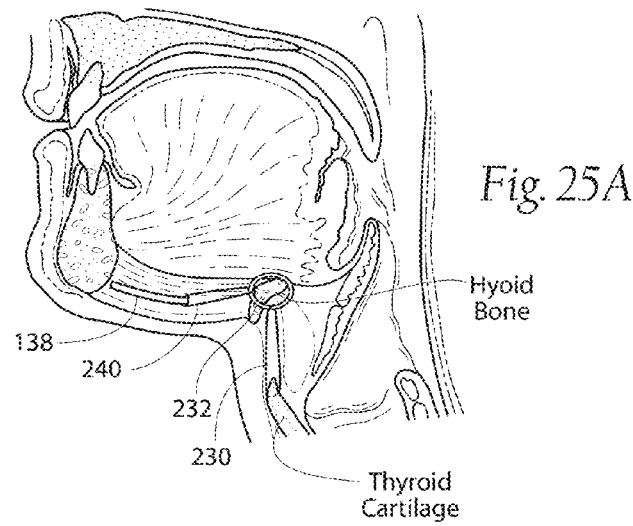
FIGS. 25A and 25B are anatomic views of an oral cavity, pharynx, and larynx of an adult human, with the mouth closed, showing a representative embodiment of system comprising a scaffold structure implanted in, on, or near the floor of the mouth and further coupled to the hyoid bone, in combination with hyoid bone stabilization (caudal).
Figure 25B:
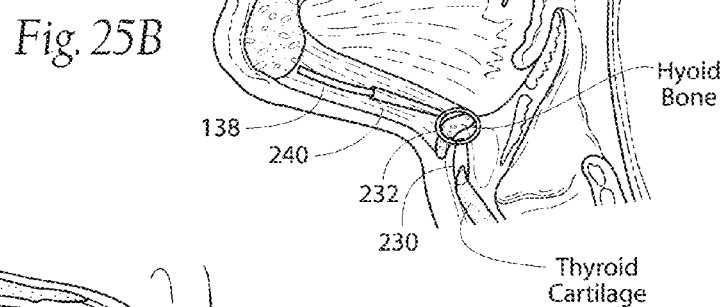

The effects of hyoid bone stabilization (caudal) can be enhanced by systems that comprise a combination of hyoid bone stabilization (caudal) with a scaffold structure 138 placed in, on, or near the floor of the mouth. As shown in FIGS. 25A and 25B, a representative system includes elastic and flexible attachments 230 between the hyoid bone and inferior and/or anterior tissue structures, such as the thyroid cartilage (as just described), and an anterior-to-posterior scaffold structure 138 implanted in, on, or near the floor of the mouth, like the scaffold structure 138 shown in FIG. 12A. In FIGS. 25A and 25B, the scaffold structure 138 is further illustrated as being attached by material 240 to the hyoid bone. The attachment material 240 can comprise, e.g., flexible and elastic linkage material coupled by a rigid ring 232 or the non-elastic suture to the hyoid bone. As shown in FIG. 25A, the flexible attachment 230 between the hyoid bone and thyroid cartilage can be attached to the same ring 232. The flexible and elastic attachments 230 between the hyoid bone and inferior and/or anterior tissue structures, such as the thyroid cartilage (as just described), pulls or pivots the hyoid bone toward the thyroid cartilage (as indicated by the arrows in FIG. 25A, and, if desired, can pull the hyoid bone into substantially the same plane as the thyroid cartilage (as shown in FIG. 25B), to provide stabilization for the hyoid bone. Alternatively, the scaffold structure 138 is not attached to the hyoid bone.

Instead of a scaffold structure 138 that extends anterior-to-posterior, a scaffold structure 138 that extends laterally near the hyoid bone, like that shown in 18B, either attached or not attached to the hyoid bone, can be used in combination with hyoid bone stabilization (caudal).

The scaffold structure 138 can be stiffened or shaped to resist buckling of tissue structures in, on, or near the floor of the mouth in a cranial direction and/or to possess a preferentially bend to bias the scaffold structure 138 in a caudal direction toward the feet, as previously described, or include a component that is activated by mechanical and/or thermal and/or electrical and/or magnetic energy, that, in association with an external carrier structure, draws the scaffold structure 138 caudally. Such combination systems makes possible a more coordinated "gentle" influence of tissues, rather than a more forceful treatment with only one mechanism of action.

Figure 25C:
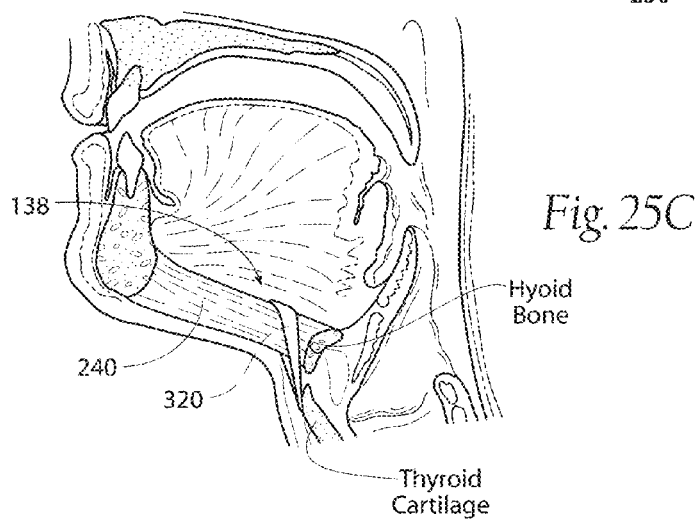
FIG. 25C is an anatomic view of an oral cavity, pharynx, and larynx of an adult human, with the mouth closed, showing a representative embodiment of system comprising a bridle implanted in, on, or near the floor of the mouth and coupled to the thyroid cartilage to resist buckling of tissue structures in, on, or near the floor of the mouth in a cranial direction.

As shown in FIG. 25C, the scaffold structure 138 can take the form of a bridle assembly 320 sized and configured to encompass tissue structures in, on, or near the floor of the mouth. As shown in FIG. 25C, the bridle assembly 320 is sized and configured to be passed through tissue structures in, on, or near the floor of the mouth (and, if desired, also encompassing a portion of the genioglossus muscle). The inferior region of the bridle assembly 320 is attached to the thyroid cartilage or adjacent connective tissue. The bridle assembly 320 is preferably flexible, and most preferably flexible and elastic, comprising springs; coils; elastic bands; synthetic fibers having elasticity, e.g., a polyurethane-polyurea copolymer such as "Spandex" or "Elastane" or "Lycra" or "Elaspan" or "Creora" or "ROICA" or "Dorlastan" or "Linel" or "ESPA." A bridle assembly 320 that is secured to a robust inferior tissue structure like the thyroid cartilage, and that encompasses more superior tissue structures in, on, or near the floor of the mouth, serves to resist buckling of tissue structures in, on, or near the floor of the mouth in a cranial direction.

2. Hyoid Bone Stabilization (Anterior)

Figure 26A:
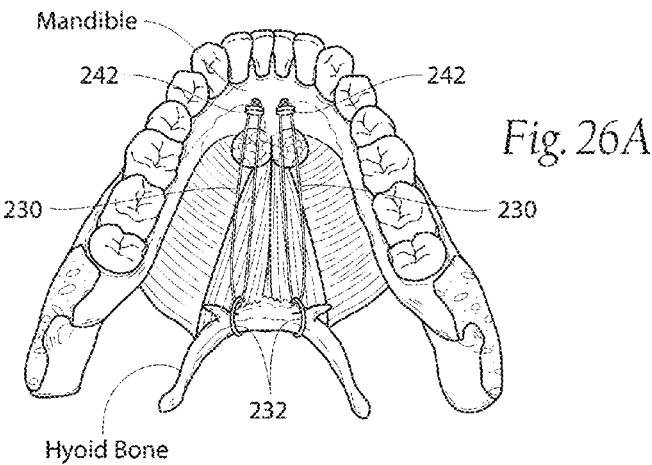
FIG. 26A is a superior view of the floor of the mouth, showing a representative embodiment of a hyoid bone stabilization (anterior) system.

Either undertaken alone or in combination with the implantation of a scaffold structure 138 in the floor of the mouth, posterior movement of the hyoid bone can be diminished or prevented by linking the hyoid bone to the lower mandible (as FIG. 26A shows), which, in shorthand, will be called hyoid bone stabilization (anterior). Hyoid bone stabilization (anterior) is accomplished by advancing and suspending the hyoid bone and associated musculature anteriorly by the use of sutures looped around the hyoid bone and attached across the oral cavity to screws 242 implanted in the lower mandible.

As in the case of hyoid bone stabilization (caudal), and as shown in shown in FIG. 26A, the effects of hyoid bone stabilization (anterior) can be enhanced by the use of attachments 230 between the hyoid bone and the lower mandible, with or without the placement of a scaffold structure in, on, or near the floor of the mouth. The attachments 230 can be rigid, but are more preferably flexible, and most preferably flexible and elastic. As shown in FIG. 26, flexible and elastic materials 230 such as springs; coils; elastic bands; synthetic fibers having elasticity, e.g., a polyurethane-polyurea copolymer such as "Spandex" or "Elastane" or "Lycra" or "Elaspan" or "Creora" or "ROICA" or "Dorlastan" or "Linel" or "ESPA" can form flexible and elastic linkages between the hyoid bone and the screws 242 in the lower mandible. As also shown in FIG. 26A, the flexible and elastic material 230 can be coupled to the hyoid bone and/or the thyroid cartilage by rigid rings 232, which permit rotation but limit linear motion. As before described, these linkages 230/232 can be quickly secured in a minimally invasive manner. The linkage materials 230/232 can be surface treated (e.g., ePTFE encapsulation) to limit fibrotic encapsulation to maintain tissue flexibility around them.

Alternatively, or in combination, the effects of hyoid bone stabilization (anterior) can be enhanced by the use of flexible but not elastic, non-fatiguing metal or plastic materials 234 (like that shown earlier in FIG. 23), such as wire rope or braided wire to link the hyoid bone to the thyroid cartilage. Crimping mechanisms 236, like those shown earlier in FIG. 23, can be used to secure the ends of the wire or braided rope materials together. These materials provide tensile strength but resist fatigue and breaking during use.

Figure 26B:
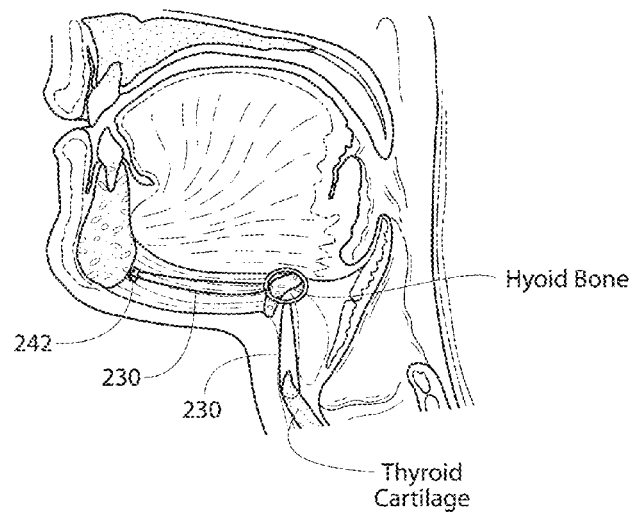
FIG. 26B is a side anatomic view of the oral cavity and floor of the mouth, showing a representative embodiment of a system comprising a combination of hyoid bone stabilization (caudal) and hyoid bone stabilization (anterior) using separate attachment mechanisms between the mandible and hyoid bone and between the hyoid bone and the thyroid cartilage.
Figure 26C:
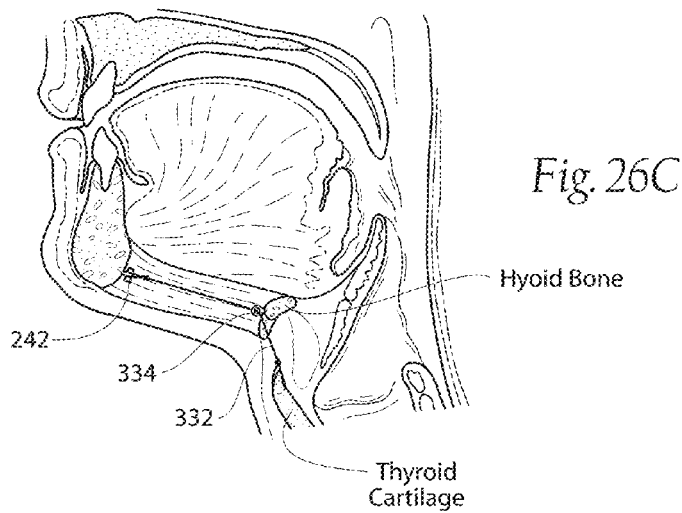
FIG. 26C is a side anatomic view of the oral cavity and floor of the mouth, showing a representative embodiment of a system comprising a combination of hyoid bone stabilization (caudal) and hyoid bone stabilization (anterior) using a unitary triangular linkage mechanism, with a posterior region of the mechanism coupled to the thyroid cartilage (or adjacent connective tissue), and anterior region of the mechanism coupled to the mandible (or adjacent connective tissue), and an intermediate region of the mechanism sliding through a guide (e.g., a ring or tube) coupled anteriorly to the hyoid bone.
Figure 26D:
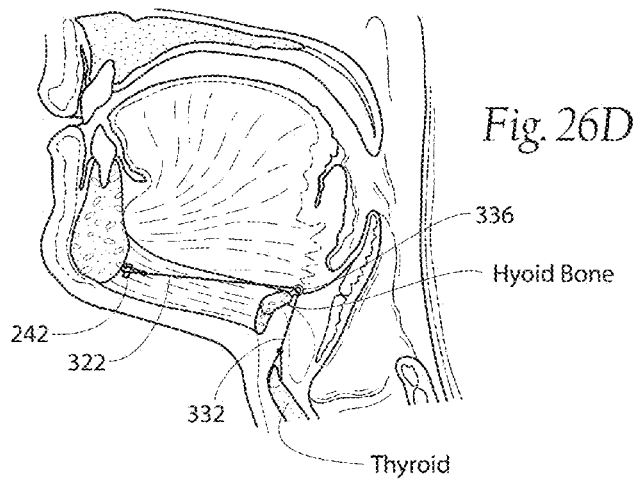
FIG. 26D is a side anatomic view of the oral cavity and floor of the mouth, showing an alternative arrangement of the unitary triangular linkage mechanism as shown in FIG. 26C, in which the intermediate region slides of the mechanism through a guide posterior to the hyoid bone.

The effects of hyoid bone stabilization (anterior) can be enhanced by systems that comprise a combination of hyoid bone stabilization (anterior) and hyoid bone stabilization (caudal), as shown in FIG. 26B. In this arrangement, linkages 230 can extend both between the hyoid bone and thyroid cartilage and between the hyoid bone and screws 242 in the lower mandible. As shown in FIG. 26C, a unitary triangular linkage mechanism 322 can be placed instead of individual linkages, with a posterior region of the mechanism coupled to the thyroid cartilage (or adjacent connective tissue), and anterior region of the mechanism coupled to the mandible (or adjacent connective tissue) (e.g., by screws 242), and an intermediate region of the mechanism sliding through a guide 324 (e.g., a ring or tube) coupled anteriorly to the hyoid bone. In an alternative arrangement, shown in FIG. 26D, the intermediate region of the unitary triangular linkage mechanism 322 slides through a guide 326 posterior to the hyoid bone. The unitary triangular linkage mechanism 322 can be rigid, but is more preferably flexible, and most preferably flexible and elastic.

Figure 27:
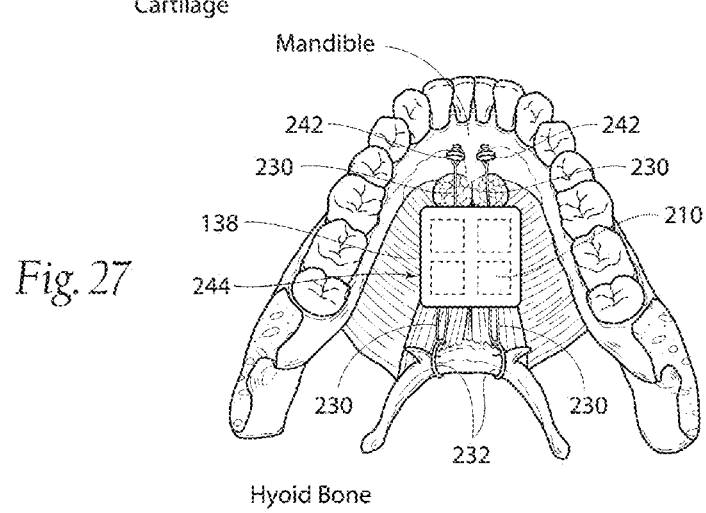
FIG. 27 is a superior view of the floor of the mouth, showing a representative embodiment of a system comprising a scaffold structure implanted in, or, or near the floor of the mouth and further coupled to the hyoid bone, in combination with hyoid bone stabilization (anterior).

The effects of hyoid bone stabilization (anterior) can also be enhanced by systems that comprise a combination of hyoid bone stabilization (anterior) with a scaffold structure 138 placed in, on, or near the floor of the mouth. As shown in FIG. 27, a representative system 244 includes elastic and flexible attachments 230 between the hyoid bone and a posterior region of the scaffold structure 138, which is implanted in the floor of the mouth. Flexible and elastic attachments 230 also extend between the anterior region of the scaffold structure 138 and screws 242 implanted in the lower mandible. The scaffold structure 138 can be stiffened or shaped to resist buckling of tissue structures in, on, or near the floor of the mouth in a cranial direction and/or to possess a preferentially bend to bias the scaffold structure 138 in a caudal direction toward the feet, as previously described, or carry one or more components that are activated by mechanical and/or thermal and/or electrical and/or magnetic energy (magnets 210 are shown in FIG. 27) that, in association with an external carrier structure 214 (like that shown in FIG. 19D), draw the scaffold structure caudally.

As shown in FIG. 28A, taking into account that the most unstable tissue region in the floor of the mouth is often closer to the hyoid bone than it is to the mandible, the scaffold structure 138 implanted in, on, or near the floor of the mouth can possess variable regions of stiffness. More particularly, the scaffold structure 138 can possess greater stiffness or rigidity (e.g., by having a different durometer material or a different thickness) in regions 246 nearer to the hyoid bone than in regions 248 nearer to the mandible. The regions 246 of greater rigidity nearer to the hyoid bone provide more support in the more unstable tissue region than elsewhere in the floor of the mouth, where less rigidity serves as a benefit, e.g., the regions 248 nearer to the mobile mandible. The transition region 250 between the two more rigid and less rigid regions 246/248 can be malleable to dynamically adapt to the morphology of mobile tissue structures in the floor of the mouth.

Figure 28B:
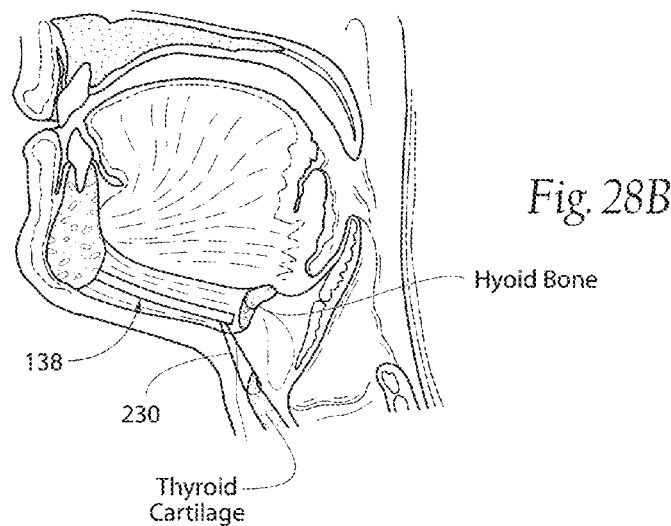
FIG. 28B is an anatomic view of an oral cavity, pharynx, and larynx of an adult human, with the mouth closed, showing a representative embodiment of a system comprising a scaffold structure implanted in, or, or near the floor of the mouth, coupled to the mandible and further coupled to the thyroid cartilage.

In FIG. 28A, the posterior end of the scaffold structure 138 is coupled to the hyoid bone, and therefore lays in general alignment with the hyoid bone. As shown in FIG. 28B, the posterior end of the scaffold structure, in an alternative arrangement, is coupled by attachments 230 to the thyroid cartilage or to connective tissue near the thyroid cartilage. The attachments 230 can be rigid, but are more preferably flexible, and most preferably flexible and elastic. The attachments pull the posterior end of the scaffold structure 138 out of alignment with the hyoid bone, into a position inferior to the hyoid bone. In this inferior angular orientation in, on, or near the floor of the mouth extending between and coupled to the mandible and the thyroid cartilage, the scaffold structure 138 resists buckling of tissue structures in, on, or near the floor of the mouth in a cranial direction, in effect biasing the tissue structures in a caudal direction toward the feet. The scaffold structure 138 can be encapsulated in a silicone or another biocompatible material. The scaffold structure 138 can be surface treated (e.g., ePTFE encapsulation) to limit fibrotic encapsulation to maintain tissue flexibility around it.

Figure 29:
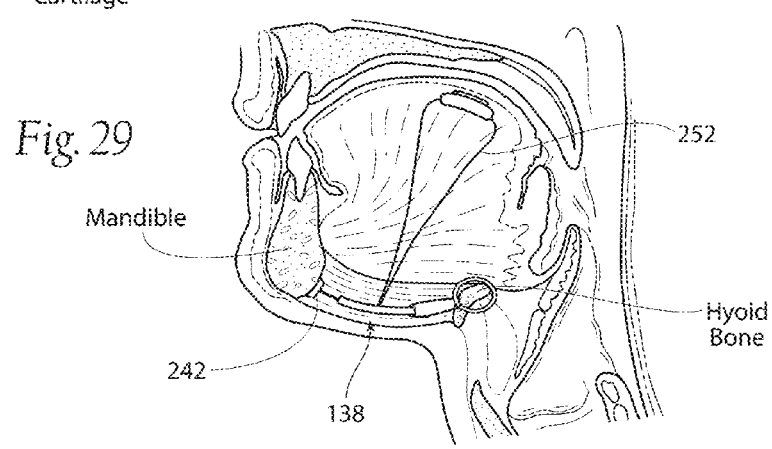
FIGS. 29 and 30 are anatomic views of an oral cavity, pharynx, and larynx of an adult human, with the mouth closed, showing a representative embodiment of a system comprising a scaffold structure implanted in, or, or near the floor of the mouth and further coupled to the hyoid bone and mandible to achieve hyoid bone stabilization (anterior), in combination with a tongue suspension device coupled to the scaffold structure, the tongue suspension device comprising a lasso-like structure in FIG. 29 and comprising a structure having one or more struts in FIG. 30.
Figure 30:
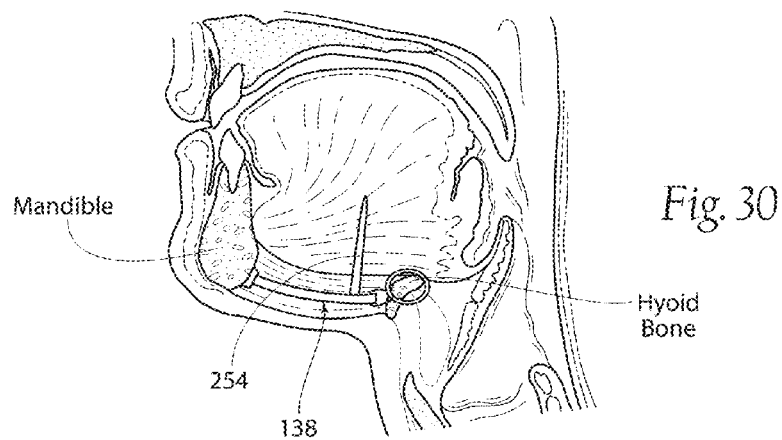

As further shown in FIG. 29, the scaffold structure 138 in, on, or near the floor of the mouth can also serve as an anchoring structure for a tongue suspension structure 252, to combine hyoid bone stabilization (anterior) with tongue suspension. It should likewise be appreciated that tongue suspension can be combined with hyoid bone stabilization (caudal) through use of a scaffold structure in, on, or near the floor of the mouth, and that hyoid bone stabilization (caudal), hyoid bone stabilization (anterior), and tongue suspension can be combined by use of an anchoring structure in, on, or near the floor of the mouth. In either arrangement, coupled to the implant scaffold structure 138 in, on or near the floor of the mouth is a tongue suspension structure 252, sized and configured for placement in or on a tongue. The tongue suspension structure 252 can, e.g., comprise a looped suture structure anchored by the scaffold structure 138 (as FIG. 29 shows), or it can comprise a tine or pronged tissue implant 254 anchored by the scaffold structure 138 (as shown in FIG. 30). Further examples of anchored tine or pronged implants in the tongue in other contexts will be described later.

The integration of hyoid bone stabilization (anterior)/hyoid bone stabilization (caudal) with an implant structure 138 in, on, or near the floor of the mouth and with tongue suspension makes possible a coordinated "gentle" influence of tissues, rather than a more forceful treatment with only one mechanism of action.

Thus, it can be appreciated that tissue structures in, on, or near the floor of the mouth can themselves serve as a unique anchoring point for establishing one or more flexible linkages between the mandible and/or hyoid bone and/or tongue for the purpose of tongue suspension and/or genioglossus advancement and/or hyoid bone stabilization (anterior) and/or hyoid bone stabilization (caudal), to resist collapse of the airway, with or without the implantation of a scaffold structure 138 in, on, or near the floor of the mouth.

Figure 31:
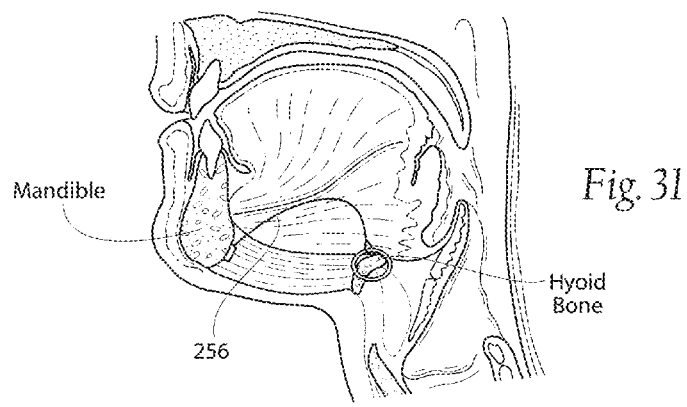
FIGS. 31 and 32 are anatomic views of an oral cavity, pharynx, and larynx of an adult human, with the mouth closed, showing representative embodiments of systems that include a tension member placed in, on, or near the floor of the floor of the mouth, establishing a flexible linkage between the hyoid bone and/or mandible and/or tongue.
Figure 32:
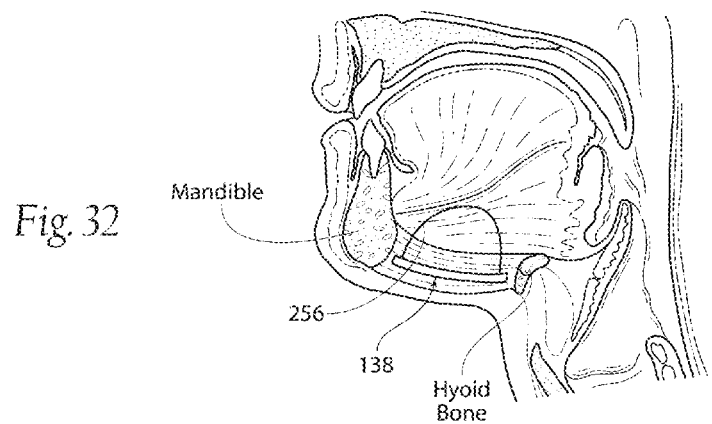

For example, as shown in FIG. 31, a tension member 256 can be placed in the floor of the mouth coupled anteriorly to the lower mandible and posteriorly to the hyoid bone. The tension member 256 draws tissue structures in the floor of the mouth downward, toward the feet, to keep the airway open. Alternatively, as shown in FIG. 32, the tension member 256 can be coupled anteriorly and posteriorly to connective tissue near the lower mandible and hyoid bone, or to a scaffold structure 138 or combinations thereof with connection to bone and to connective tissue and to the scaffold structure 138.

V. Stabilization of the Tongue
  A. Overview

Representative tongue suspension structures have been described. Other structures that otherwise stabilize the tongue can be deployed, either alone or in combination with the implantation of a scaffold structure 138 in the floor of the mouth.

B. Representative Embodiments
    1. Struts

Figure 33A:
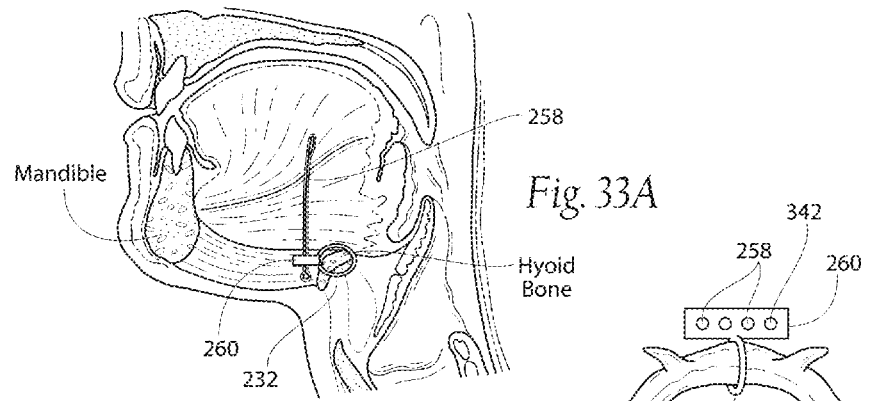
FIG. 33A is an anatomic view of an oral cavity, pharynx, and larynx of an adult human, with the mouth closed, showing a representative embodiment of a tongue stabilization system comprising one or more struts that are coupled to a mount that is, in turn, attached to the hyoid bone, the struts extending in a superior direction in an lateral array into the tongue.
Figure 33B:
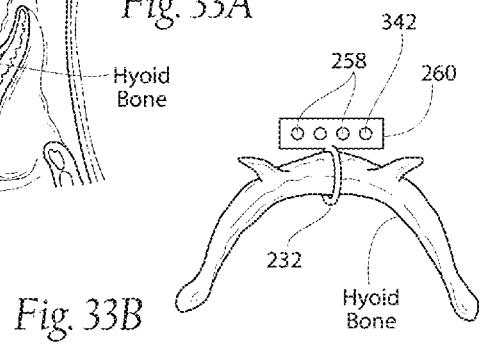
FIG. 33B is an anatomic superior view of a hyoid bone, showing the mount shown in FIG. 33A attached to the hyoid bone.
Figure 34:
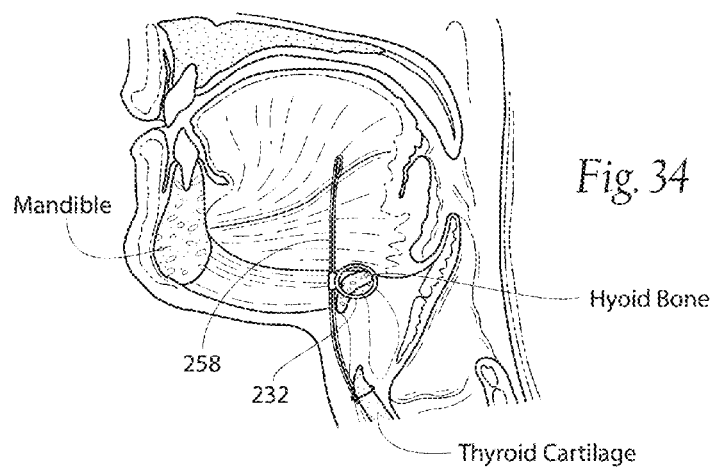
FIG. 34 is an anatomic view of an oral cavity, pharynx, and larynx of an adult human, with the mouth closed, showing a representative embodiment of a system comprising one or more struts that are coupled to the hyoid bone and that extends in a superior direction into the tongue to provide tongue stabilization, the struts also extending in an inferior direction for attachment to or abutment against the thyroid cartilage to provide hyoid bone stabilization (caudal).

For example, as shown in FIGS. 33A and 33B, stabilization of the base of the tongue can be achieved using one or more struts 258 that are coupled to a mount 260, which can be further secured to the hyoid bone or to connective tissue near the hyoid bone. The one or more struts 258 extend in a superior direction, desirably into a posterior region of the tongue. The one or more struts 258 can, if desired, be implanted directly in connective tissue near the hyoid bone or within tissue structures in, on, or near the floor of the mouth, without a mount 260. As shown in FIG. 34, for example, one or more struts 258 can be attached to the thyroid cartilage, and/or to the hyoid bone and rest anterior to the thyroid cartilage. As other examples, the one or more struts 258 can be attached to connective tissue in the floor of the mouth (FIG. 35A) and/or connected to a scaffold structure 138 in, on, or near the floor of the mouth (which also serves as the mount 260) (FIG. 35B). The mount 260 can comprise a body made from a biocompatible metallic or polymer or fiber material, or a combination thereof, or a metallic or polymer or fiber material that is suitably coated, impregnated, or otherwise treated with a material to impart biocompatibility, or a combination of such materials. Alternatively, the mount 260 can comprise a bio-resorbable structure made, e.g., of a bio-adsorbable material.

Figure 35A:
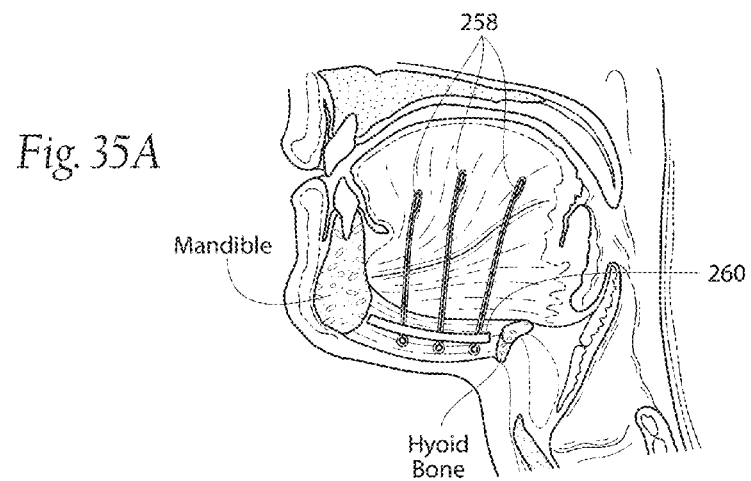
FIG. 35A is an anatomic view of an oral cavity, pharynx, and larynx of an adult human, with the mouth closed, showing a representative embodiment of a system comprising an array of one or more anterior-to-posterior struts that are coupled to tissue in, on, or near the floor of the mouth to provide tongue stabilization, in combination with an anterior to posterior scaffold structure implanted in, on, or near the floor of the mouth to provide mechanical support to structures in the floor of the mouth.
Figure 35B:
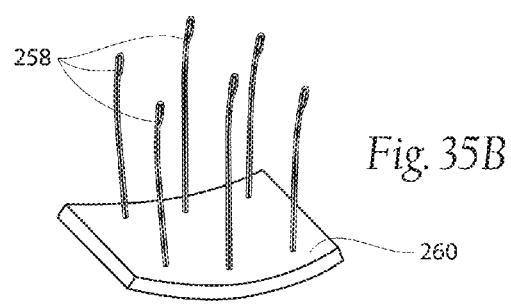
FIG. 35B is superior perspective view showing a representative embodiment of a system comprising an array of one or more anterior-to-posterior and laterally placed struts that extend in a superior direction into the tongue to provide tongue stabilization, the struts being coupled to a scaffold structure sized and configured to be implanted in, on, or near the floor of the mouth to provide mechanical support to structures in, on, or near the floor of the mouth, in combination with tongue stabilization.

Struts 258 may be arranged in a lateral array on the mount 260 in, on, or near the floor of the mouth (as FIGS. 33A and 33B show), or they can be arranged in an anterior-to-posterior array (as FIG. 35A shows), or combinations thereof (as FIG. 35B shows).

Figure 36A:
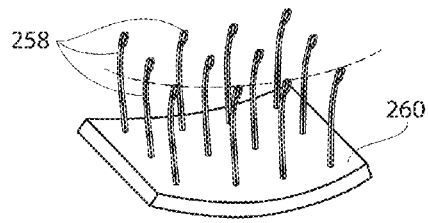
FIGS. 36A, 36B, 36C, 36D, and 36E are perspective views of systems comprising arrays of one or more anterior-to-posterior and laterally placed struts, like that shown in FIG. 35B, showing how the lengths of the struts can be varied to achieve the desired therapeutic objectives.
Figure 36B:
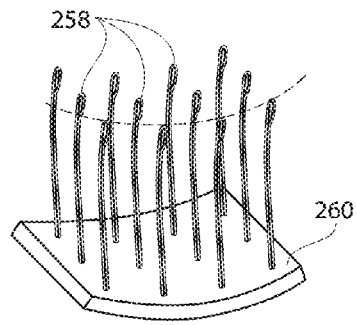
Figure 36C:
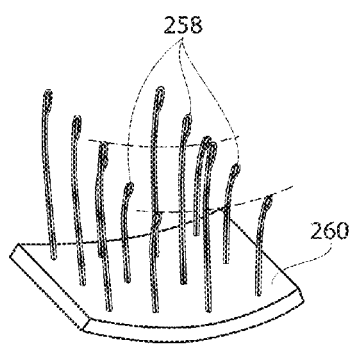
Figure 36D:
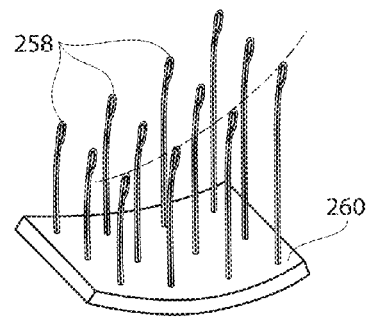
Figure 36E:
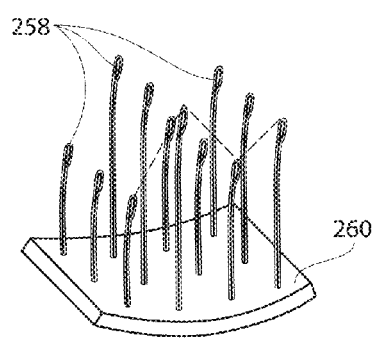

The relative magnitude of the lengths or heights of a single strut 258 or array of struts, measured in a superior direction from the mount 260 into the tongue, can vary, according to the therapeutic objectives, e.g., from shorter (see FIG. 36A) to longer (see FIG. 36B). A given array can include repetitive, progressive, and/or random combinations of lengths thereof (see FIGS. 36C, 36D, and 36E).

Furthermore, the angular orientation of a single strut 258 or an array of struts relative to the sagittal plane can also vary according to the therapeutic objectives, e.g., from generally aligned in an inferior-to-superior direction along the sagittal plane (see Position 1 in FIGS. 37A and 37B), to being angled within a continuous range in an anterior or posterior direction within the sagittal plane (see Positions 2 and 3 in FIG. 37A), and/or angled in a continuous range in left or right lateral directions (coronally) from the sagittal plane (see Positions 4 and 5 in FIG. 37B), and including a continuous range of posterolateral and anteriolateral orientations. A given array can, of course, include repetitive, progressive, and/or random combinations of angular orientations. The one or more struts 258 are desirably free of hooked surfaces, so that they can be inserted and removed with little or no tissue trauma. In any embodiment, the length(s) and/or angular orientation(s) of the one or more struts 258 serve as restraint(s) to resist posterior movement of the tongue. In addition to selection of length and angular orientation, the struts 258 can be sized and configured to posse an anterior bias to urge tissue toward an anterior position. In this representative arrangement, the one or more struts 258 desirably possess a spring constant to serve as a leaf-spring to pull the tongue forward. The one or more struts 258 can also serve this purpose by comprising a mechanically actuated material, and/or an electrically actuated shaped material, and/or a thermally activated shaped material, and/or a magnetically actuated material. Alternatively, or in the combination, the one or more struts 258 can be made from metal (such as nitinol) or polymers or fibers and further comprise springs, coils, elastic fibers made from synthetic fibers having elasticity, e.g., a polyurethane-polyurea copolymer such as "Spandex", wire such as nitinol, or a composite of these and other flexible polymers. The struts 258 can be surface treated (e.g., ePTFE encapsulation) to limit fibrotic encapsulation to maintain tissue flexibility around it.

As FIG. 37C shows, an anterior bias can be applied to the struts 258 by mounting the struts 258 along an axle 328, which is rotationally coupled to the mount 260. The axle 328 can be rotationally biased by a coil spring 330 against a clockwise rotation, to thereby urge the struts 258 in an anterior direction, resisting movement of the base of the tongue in a posterior position. A manually adjustable tensioning mechanism 332 can be coupled to the coil spring 330 that increases or decreases (i.e., titrates) the spring constant applied to the axle 328.

FIG. 37D shows an alternative arrangement, in which a strut 258 is biased toward an anterior position by a spring 334 that is attached to the mount 260 anterior to the strut 258 and is coupled to the strut 258. The spring 334 applies anterior tension to the strut 258. As before described, a manually adjustable tensioning mechanism 336 can be coupled to the tension spring 334 that increases or decreases (i.e., titrates) the spring constant applied to the strut 238.

Figure 37E:
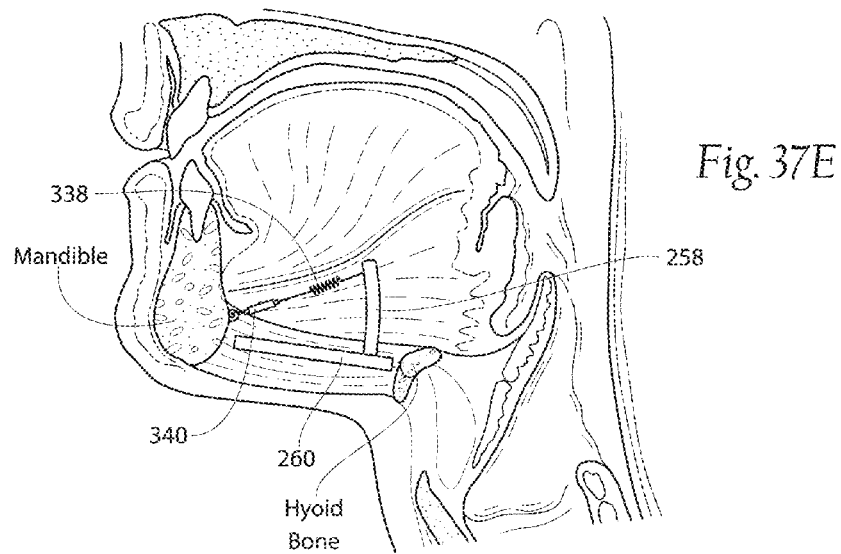

In FIG. 37E, a strut 258 is biased toward an anterior position by a spring 338 that is secured to the mandible or adjacent connective tissue and coupled to the strut 258. A manually adjustable tensioning mechanism 340 (e.g., a turnbuckle) can be coupled to the tension spring 338 that increases or decreases (i.e., titrates) the spring constant applied to the strut 238. A given strut 258 can also be biased toward an anterior position by anterior springs coupled to the mount (as in FIG. 37D) as well as the mandible or connective tissue (as in FIG. 37E). It should be appreciated that various spring-tensioned embodiments for the struts 258 are possible.

Figure 38:
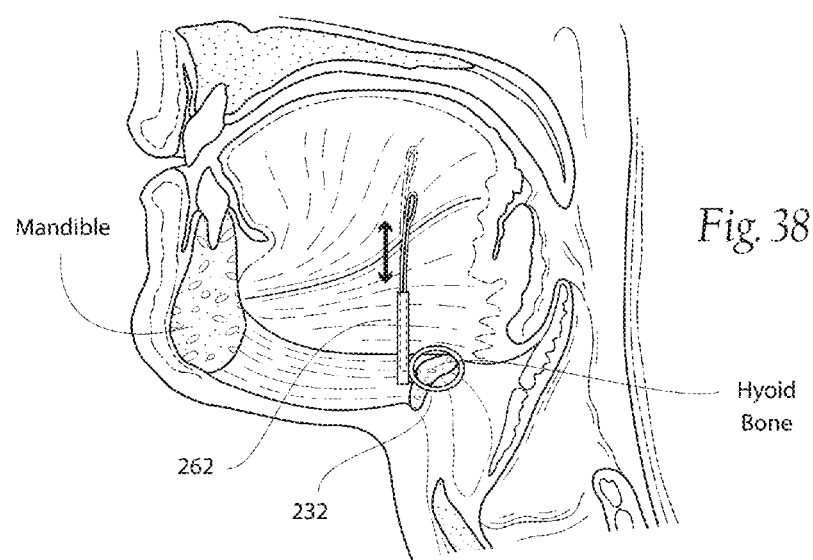
FIG. 38 is an anatomic view of an oral cavity, pharynx, and larynx of an adult human, with the mouth closed, showing a representative embodiment of a tongue stabilization system comprising one or more struts that are coupled to the hyoid bone and that extend in a superior direction into the tongue, the struts comprising piston-like structures that lengthen and shorten to adopt to the dynamic environment of the tongue.

Given the dynamic environment of the tongue during speech and swallowing, the one or more struts can comprise piston-type structures 262 (see FIG. 38) that can shorten and lengthen to adapt to the dynamic movement of the tongue. The piston-like structures 262 can be encapsulated with an elastic polymer or ePTFE to limit fibrotic encapsulation. As shown in FIG. 38, the piston-like strut structure 262 is attached by a ring 232 to the hyoid bone.

The mount 260 can be sized and configured to permit the selective and insertion and removal of struts of different heights and/or angular orientations to form diverse arrays. In this way, the number and arrangement of struts 258 can be finely titrated to achieve the desired therapeutic effect. One representative embodiment of this technical feature is shown in FIGS. 33A and 33B. In this embodiment, the mount 260 includes mounting apertures 342 that permit detachable frictional fit engagement of one or more struts 258 in a lateral array.

Figure 39A:
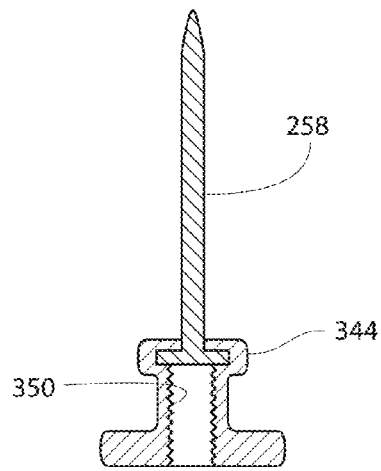
FIGS. 39A to 39F are side views of a representative embodiment showing an active mounting for a strut like that shown in FIG. 35B, comprising an elastomeric mounting boot and a companion placement tool for releasably seating the strut in a mount.
Figure 39B:
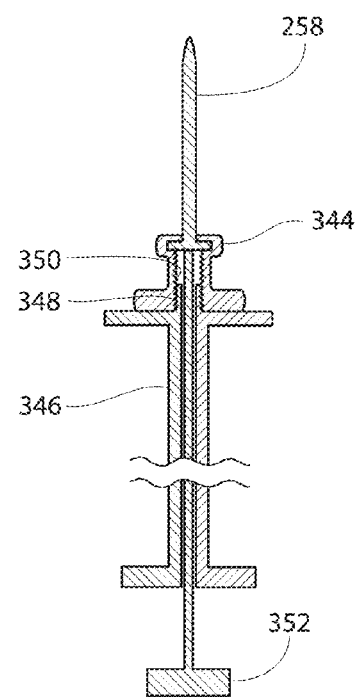
Figure 39C:
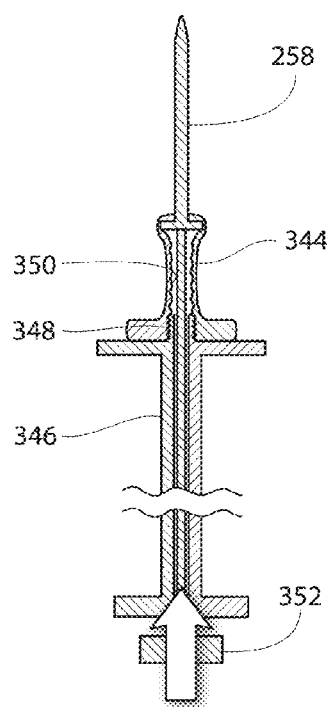
Figure 39D:
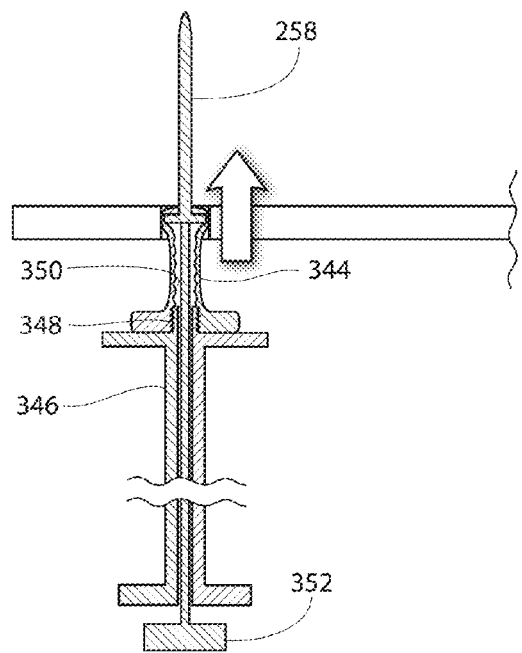
Figure 39E:
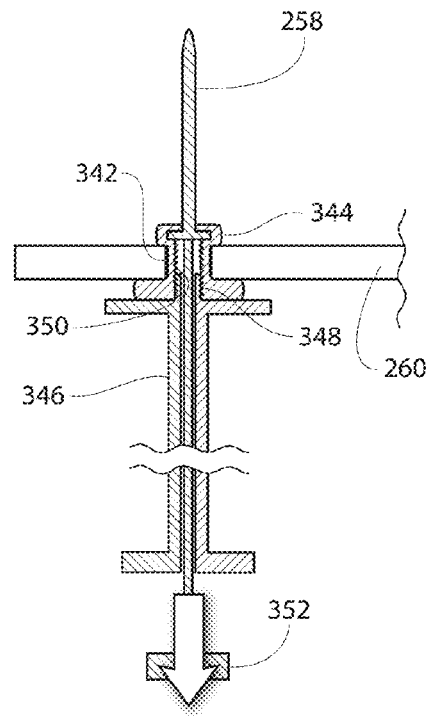
Figure 39F:
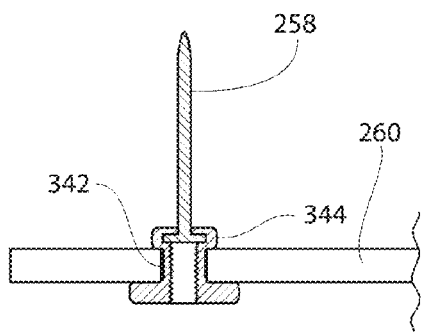

In another representative embodiment, one or more struts can be secured to the mount by an active mounting. For example, as shown FIG. 39A, a given strut 258 includes a mounting boot 344 made, e.g., from an expandable, elastomeric material. The boot 344 has a normally expanded condition (shown in FIG. 39A), which seats the strut securely within a mounting aperture (see FIG. 39F). A companion placement tool 346 (see FIG. 39B) can be included, which comprises a threaded distal end 348 that engages a threaded interior region 350 within the mounting boot 344. The placement tool 346 includes a plunger 352. After the placement tool 346 and mounting boot 344 have been threadably engaged (see FIG. 39C), depressing the plunger 352 distally stretches and elongates the mounting boot 344, to reduce its normal diameter. In a reduced diameter, the elongated boot 344 can be passed into or removed from a selected mounting aperture 342 of a mount 260 (see FIG. 39D). Moving the plunger 352 proximally allows the elastomeric memory of the mounting boot 344 to return the boot 344 to its normal expanded diameter (see FIG. 39E). The boot 344 seats the strut 258 within the mounting aperture 342, and the placement tool 346 can then be unthreaded from the mounting boot 344 and withdrawn, leaving the strut 258 secured to the mount 260 (see FIG. 39F).

Figure 40A:
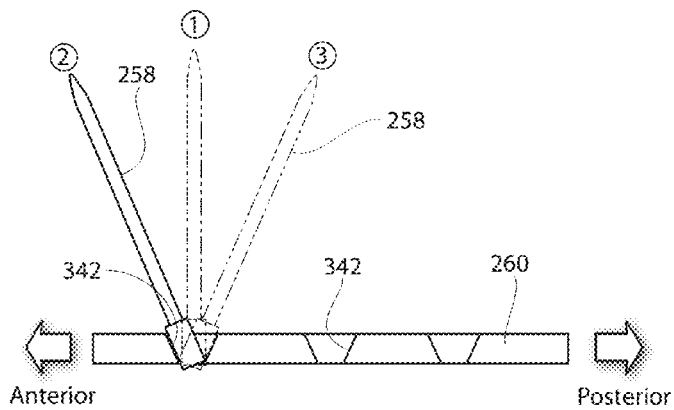
FIGS. 40A and 40B are lateral side and edge views of a mount for one or more struts, like that shown in FIG. 35B, the mount having conical mounting apertures to vary the angular orientation of the struts.
Figure 40B:
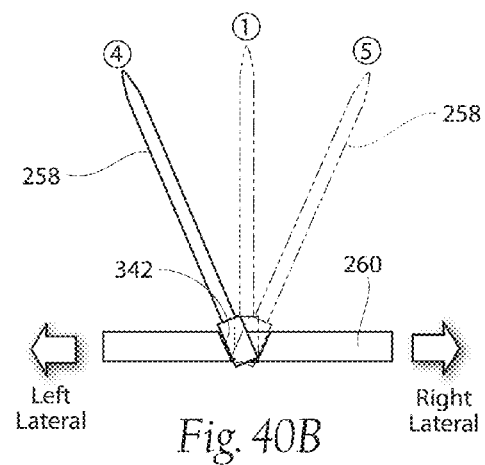
Figure 40C:
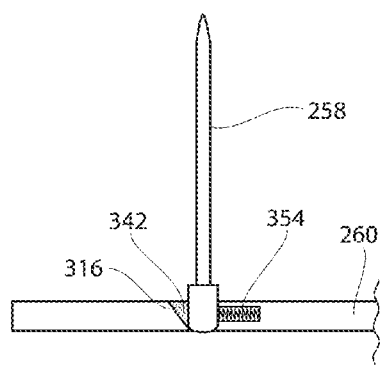
FIGS. 40C and 40D are lateral side views of a mount having conical mounting apertures like that shown in FIGS. 40A and 40B, illustrating the use of bioadsorbable material placed within a mounting aperture to vary the angular orientation of a strut over time.
Figure 40D:
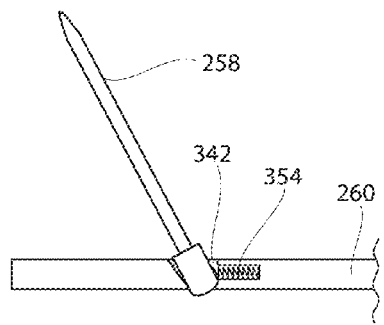

The mounting apertures 342 can also be sized and configured to affect the angular orientations of the struts 258. For example, the interiors of one or more mounting apertures 342 on a given mount can be shaped or tapered to comprise a truncated cone (see FIGS. 40A and 40B). A strut 258 can be secured within the aperture 342 (e.g., by a locking screw) within a range of angular orientations from 0°—aligned superior-to-inferior along the sagittal plane (Position 1 in FIG. 40A)—to a maximum angle established by the slope of the truncated cone, e.g., between 20° to 30° anterior (Position 2 in FIG. 40A), posterior (Position 2 in FIG. 40A), left lateral (Position 4 in FIG. 40B), right lateral (Position 5 in FIG. 40B), and infinite number of anteriolateral and posterolateral positions within this range. As FIG. 40C shows, a resorbable material 316 can be placed into the shaped mounting aperture 342 in opposition to a strut 258 against which a leaning force is applied (e.g., by a spring 354). As FIG. 40C shows, the resorbable material 316 initial resists angular tipping of the strut 258 in the direction of the material 316. However, as FIG. 40D shows, as the material 316 is resorbed, the strut 258 will incrementally tip toward the opposite tapered wall of the aperture 342 and assume a desired angular orientation. The presence of the resorbable material 316 allows tension to be applied to the tongue over time or during a set interval.

Figure 41A:
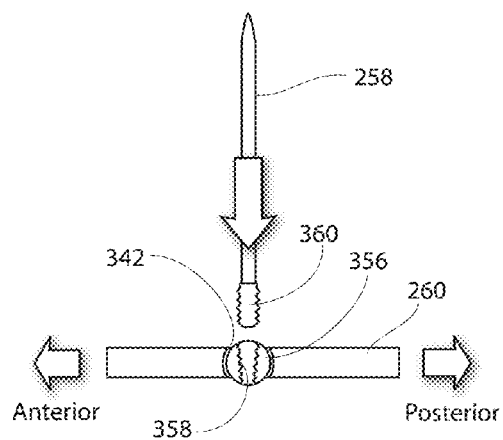
FIGS. 41A and 41B are lateral side views of a mount for one or more struts, like that shown in FIG. 35B, the mount having an expandable ball joint to vary the angular orientation of the struts.
Figure 41B:
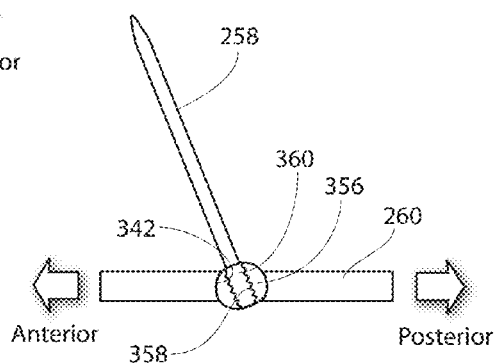

An alternative representative embodiment that also provides a continuous range of angular orientations is shown in FIGS. 41A and 41B. In this embodiment, a pivoting ball joint 356 is carried within one or more of the mounting apertures 342 (see FIG. 41A). The ball joint 356 includes a threaded bore 358. The companion strut 258 includes a coupling 360 that threadably mates with the threaded bore 358 (see FIG. 41B). The coupling 360 is sized and configured to taper, so that, when threaded into the bore 358, the ball joint 356 expands to lock it in a desired angular orientation, as FIG. 41B shows. In this way, the strut 258 can be secured within the mounting aperture 342 within a desired continuous range of angular orientations established by the pivoting ball joint 356.

Figure 42:
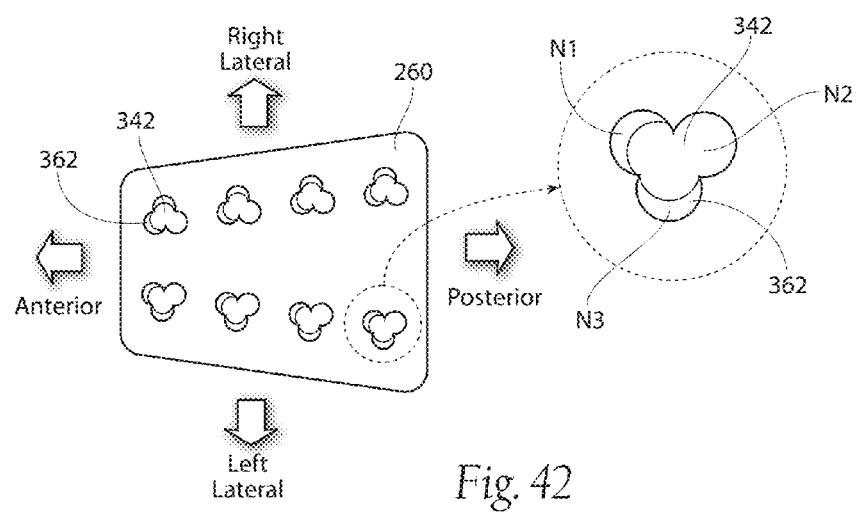
FIG. 42 is a top view of a mount for one or more struts, like that shown in FIG. 35B, the mount having mounting apertures with formed nodes to vary the angular orientation of the struts.

An alternative representative embodiment that provides an array of predefined angular orientations is shown in FIG. 42. In this embodiment, a mounting aperture 342 includes discrete, preformed mounting nodes 362, each pre-sized and pre-shaped to secure a strut 258 on the mount (e.g., by a spring-biased detent within each node) in a particular predefined angular orientation. For example, as shown in FIG. 42, a first preformed node (N1) is sized and shaped to secure a strut 258 in an angled anterior orientation; a second preformed node (N2) is sized and shape to secure a strut 258 in an upright superior-inferior orientation; and a third node (N3) is sized and shaped to secure a strut 258 in an angled anterior and lateral orientation. Of course, other prescribed angular orientations can be provided by including pre-sized and pre-shaped nodes in a mounting aperture.

Figure 43A:
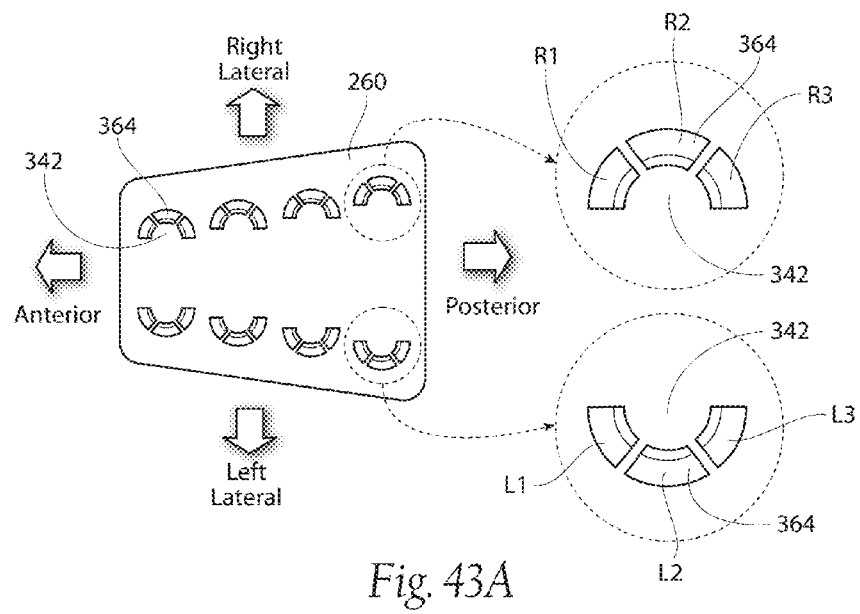
FIGS. 43A, 43B, and 43C are, respectively, a top view, a lateral side view, and an edge view of a mount for one or more struts, like that shown in FIG. 35B, the mount having mounting apertures arranged along an arc and shaped to vary the angular orientation of the struts.
Figure 43B:
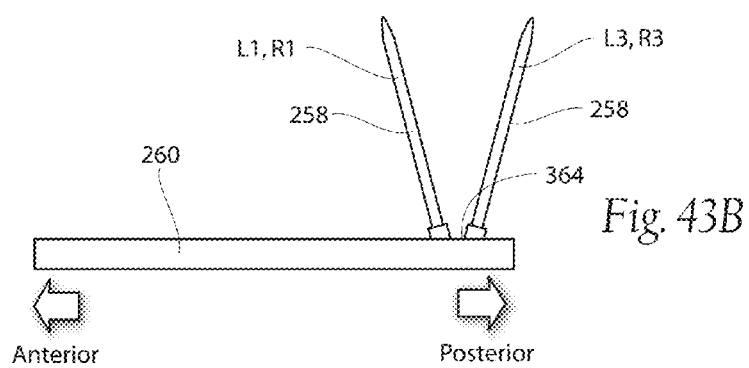
Figure 43C:
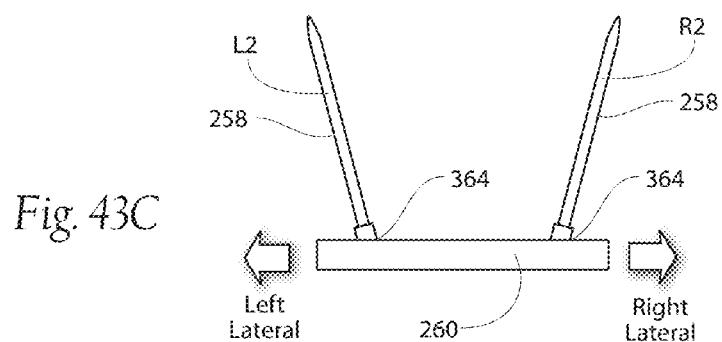

Another alternative representative embodiment that provides array of predefined angular orientations is shown in FIGS. 43A to 43C. In this embodiment, the mounting apertures include preformed cone shaped slots 364 arranged in an arcuate pattern on the mount 260. In FIG. 43A, there are six slots 364. Three slots 364 are arranged in an arcuate pattern on the left lateral side of the mount (designated from anterior to posterior L1, L2, and L3 in FIG. 43A). Three slots 364 are arranged in an arcuate pattern on the right lateral side of the mount (designated from anterior to posterior R1, R2, and R3 in FIG. 43A). Each slot (L1, L2, L3, R1, R2, and R3) is sized and configured to define a predefined angular orientation for a strut 258 secured within it. For example, a strut 258 secured in slot L1 or R1 will be angularly oriented in an anterior direction on the respective left and right lateral sizes (see FIG. 43B). A strut 258 secured in slot L2 or R2 will be angularly oriented in a lateral direction on the respective left and right lateral sizes (see FIG. 43C). A strut 258 secured in slot L3 or R3 will be angularly oriented in a posterior direction on the respective left and right lateral sizes (see FIG. 43C).

Figure 44A:
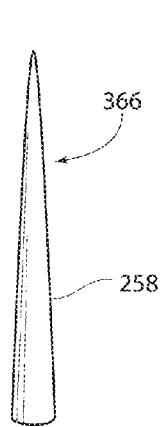
FIGS. 44A and 44B are side views of a tapered strut and companion placement tool.
Figure 44B:
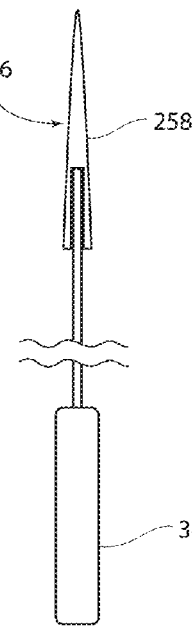

The one or more struts 258 can be sized and configured with various cross sections, e.g., generally curvilinear (i.e., round or oval), or a generally rectilinear (i.e., square or rectangular or triangular, or combinations thereof. The one or more struts 258, whether curvilinear or rectilinear in cross section, can include a tapered region 366 at least along a portion of its axial length (see FIG. 44A), meaning that the width or diameter of the one or more struts 258 incrementally decreases along its axial length in a distal direction to aid inserting into tongue tissue. As FIG. 44B shows, a stylet 368 may be used to insert a given tapered strut 258, followed by the attachment of the proximal end to the mount 260 implanted in, on, or near the floor of the mouth, as previously described.

Figure 44C:
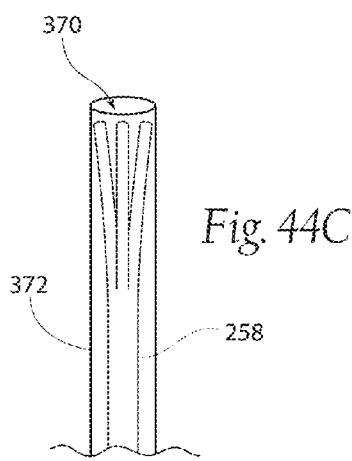
FIGS. 44C and 44D are side views of a strut and companion placement tool, the strut having a splayed distal end.
Figure 44D:
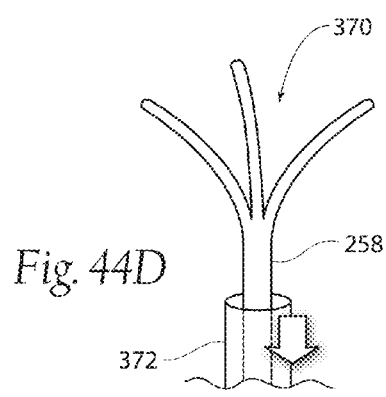

Alternatively, the distal ends of the one or more struts 258 may be sized and configured to expand or enlarge upon insertion, to increase the purchase of the struts in tissue. A representative embodiment is shown in FIGS. 44C and 44D, in which a strut 258 includes a resiliently splayed distal end 370, in which the distal end 370 is normally resiliently separated into two or more diverging branches. When inserted through a hollow needle or cannula 372 (see FIG. 44C), the splayed distal end 370 is retained in a low profile condition. When freed from the hollow needle or cannula 372 (see FIG. 44D), the distal end 370 resilient springs into its splayed configuration, increasing the surface area of the strut 258 at its distal end to resist its migration in tissue.

Figure 44E:
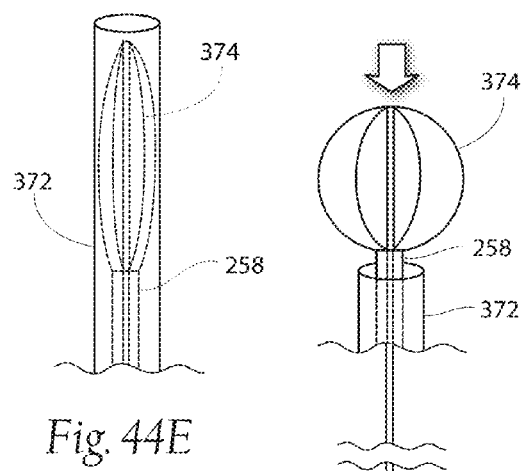
FIGS. 44E and 44F are side views of a strut and companion placement tool, the strut having an expandable distal end.
Figure 44F:
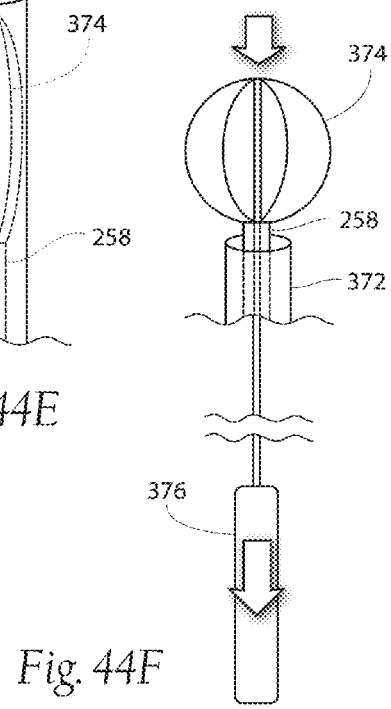

Another representative embodiment is shown in FIGS. 44E and 44F, in which a strut 258 includes an expandable basket structure 374 on its distal end. When inserted through a hollow needle or cannula 372 (see FIG. 44E), the basket 374 is collapsed in a low profile condition. Outside the hollow needle or cannula 372 (see FIG. 44F), a stylet 376 placed through the needle or cannula 372 and engages the basket 374 to mechanically open the basket 374 (like an umbrella), increasing the surface area of the strut 258 at its distal end to resist its migration in tissue. The stylet 376 can also, when desired, reengage the basket 374 to mechanically collapse the basket 374 to allow non-traumatic removal or repositioning of the strut 258.

In another representative embodiment, the one or more struts 258 may include preformed curve 378 at its distal end, as shown in FIG. 45A. As shown in FIG. 45A, the strut 258 can also be tapered in a proximal to distal direction, as previously described and shown in FIG. 44A. As FIG. 45B shows, the curved distal end 378 may be rotated after placement in tissue to create an anterior and lateral pull or tension on the tongue tissue. Lateral tension may be particularly beneficial if the tongue has a deep midline groove that can be opened with lateral tension.

It can be appreciated that systems comprising one or more struts 258 carried by a mount implanted in, on, or near the floor of the mouth, as described, can be adjusted in terms of number, lengths, and diverse ranges of anterior and/or posterior orientation and/or anterior/lateral and/or posterior/lateral orientation, either during initial implantation or during follow up at a later date. Such systems make possible fine adjustment and titration in order to optimize the magnitude and direction of tension applied to tongue tissue to prevent posterior collapse and obstruction of the airway.

Systems comprising one or more struts 258 carried by a mount 260 implanted in, on, or near the floor of the mouth, as described, also make possible straightforward implantation techniques. Implantation of such systems can be accomplished through a single incision or portal to place the mount 260 and struts 258, without open incisions within the oral cavity. This straightforward approach is advantageous when compared to other conventional methods that constrain the tongue (e.g., other genioglossus advancement techniques), which require multiple, invasive entries or portals for installation. And, as also described, the mount 260 can be sized and configured to perform the added function of a scaffold structure 138.

2. Flexible Tongue Lever

Figure 46C:
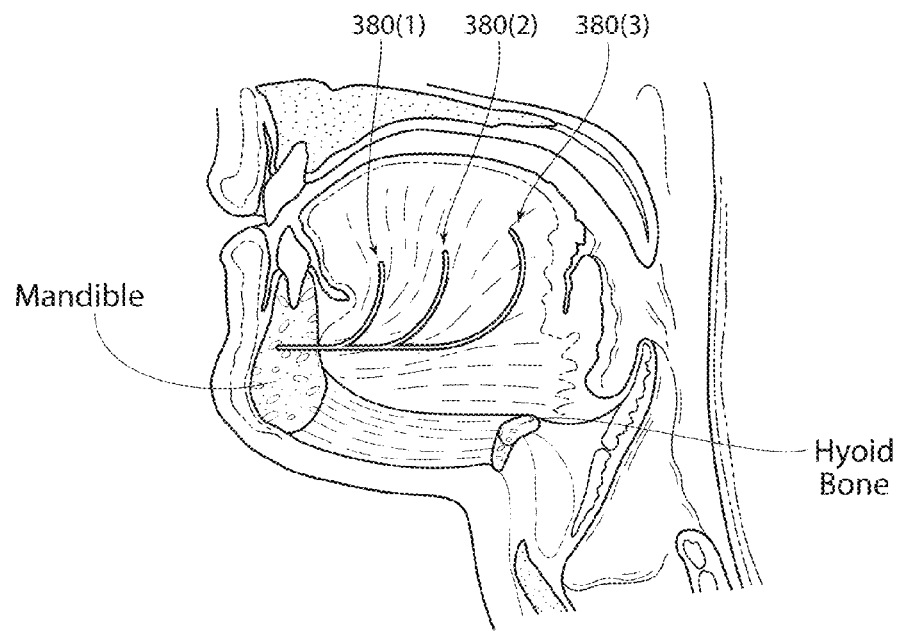
FIG. 46C is anatomic view of an oral cavity, pharynx, and larynx of an adult human, with the mouth closed, showing another representative embodiment of a flexible tongue lever system.

As shown in FIG. 46A, stabilization of the base of the tongue can be achieved using a tongue lever 380. The tongue lever 380 includes a generally straight, flexible anterior section 382 and a curved, flexible posterior region 384 coupled to the anterior section 382. The anterior section 382 is attached (e.g., by adhesive, clips, or screws) anteriorly to the mandible, or to connective tissue near the mandible, or to structures in, on, or near the floor of the mouth. The posterior section 384 extends in a curved, j-shaped path through tissue in a posterior region of the tongue.

As FIG. 46B shows, as the mandible drops with an opening of the mouth, the tongue lever 380 applies an anterior force to the tongue, resisting posterior movement of the base of the tongue into the airway. The flexible, curved posterior section 384 of the lever 380 engages more tissue than a conventional tongue suspension hook. It also provides more flexibility than a convention suture loop or basket used for tongue suspension, which is attached at two ends rather than one. The flexible tongue lever 380 may therefore be placed with much less tension than a conventional tongue suspension device. The generally straight, flexible anterior section 382 of the lever can also be elastic as well as flexible, and in one example, need only withstand moderate force (e.g., approximately 40 to 70 grams of force) to restrict posterior tongue motion.

During motion, such as swallowing, the flexible tongue lever 380 extends/flattens out, to thereby reduce likelihood of tissue tolerance issues or migration.

In an alternative arrangement (see FIG. 46C), more than one flexible tongue lever 380(1), 380(2), 380(3) may be separately implanted extending into different anterior and posterior regions of the tongue to resist posterior movement of the base of the tongue into the airway.

3. Combination Systems

The effects of tongue stabilization can be enhanced by systems that comprise a combination of a tongue stabilization structure or structures and a scaffold structure 138 placed in, on, or near the floor of the mouth. For example, the mount 260 shown in FIGS. 33A and 33B can include the technical features of a laterally implanted scaffold structure 138, as previously described.

Figure 47A:
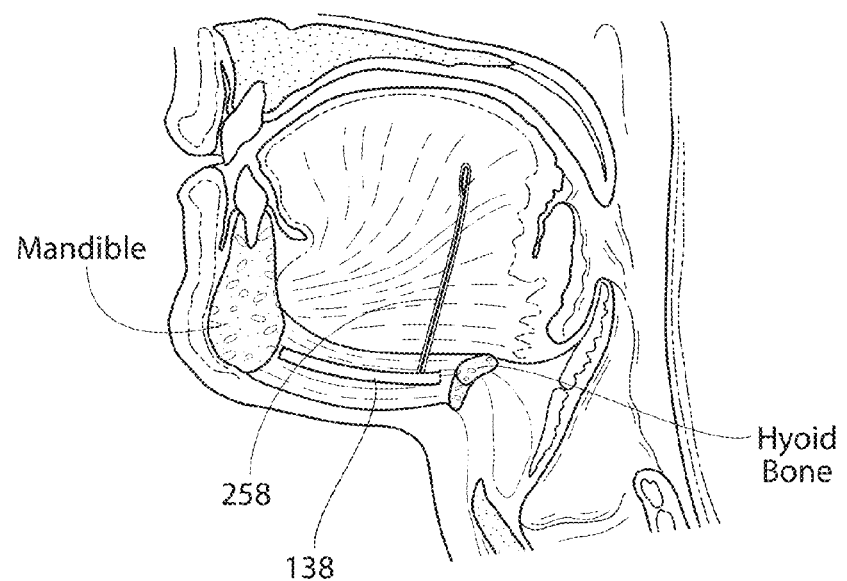
FIG. 47A is an anatomic view of an oral cavity, pharynx, and larynx of an adult human, with the mouth closed, showing a representative embodiment of a system comprising one or more struts that extend in a superior direction into the tongue to provide tongue stabilization and that is coupled to a scaffold structure implanted in, on, or near the floor of the mouth to provide mechanical support to structures in the floor of the mouth, in combination with tongue stabilization.

In FIG. 35B, the implanted struts 258 are used in combination with a scaffold structure 138 implanted in an anterior-to-posterior orientation in, on, or near the floor of the mouth. FIG. 47A shows another embodiment of one or more struts 258 integrated with a scaffold structure 138 implanted in, on, or near the floor of the mouth. In FIG. 47 (as in FIGS. 35A and 35B), for purpose of illustration, the scaffold structure 138 extends in an anterior-to-posterior direction within the floor of the mouth without attachment to the hyoid bone, but could, if desired, be also attached to the hyoid bone and/or the mandible and/or the thyroid cartilage. The scaffold structure 138 lends support for tissue structures in, on, or near the floor of the mouth to resist buckling of the tissue structures in, on, or near the floor of the mouth in a cranial direction and/or to preferentially bias the scaffold structure 138 in a caudal direction. The presence of the strut 258 serves as a restraint to resist posterior movement of the tongue, and thereby achieve tongue suspension. The scaffold structure 138 complements the therapeutic effects of tongue stabilization.

Figure 47B:
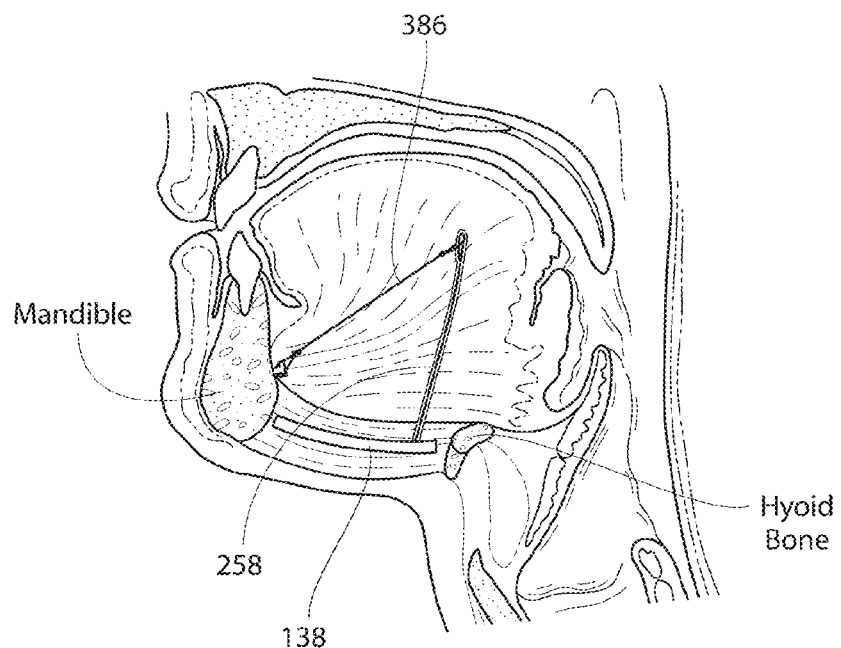
FIGS. 47B and 47C of the system shown in FIG. 47A, with the distal region of the strut coupled, respectively to the mandible or to the anterior region of the scaffold structure to alter the force vectors of tongue stabilization.
Figure 47C:
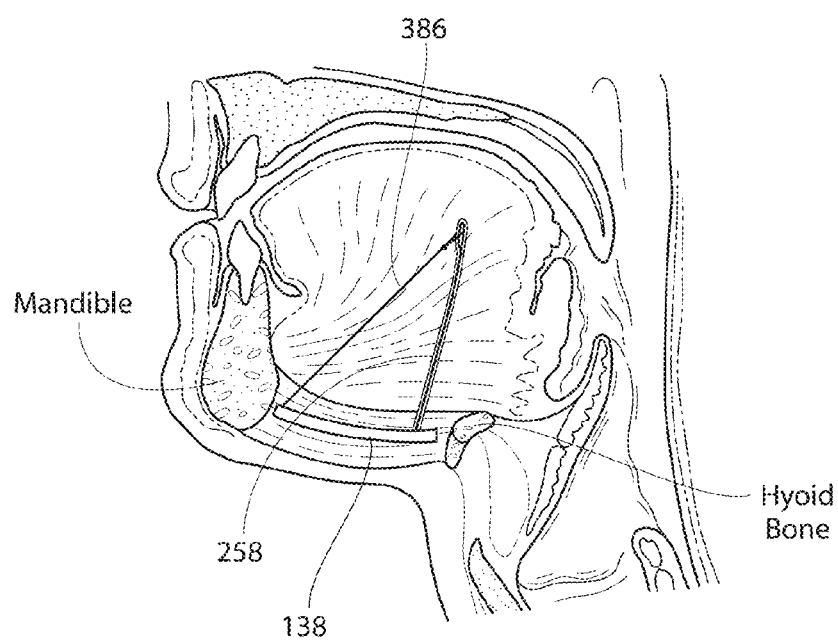

In FIG. 47B the strut 230 includes an anterior connection member 386 coupled to the mandible. In FIG. 47C, the strut 230 includes an anterior connection member 386 coupled to the anterior end of the scaffold structure 138. The connection members 386 can be rigid, but are more preferably flexible, and most preferably flexible and elastic. The anterior connection members 386 coupled to the strut 258 alter the force vector of the tongue suspension. The anterior coupling of the strut 138 to the mandible and/or anterior end of the scaffold structure 138 creates a resulting force vector that has both an anterior component and an inferior component to resists posterior movement of the base of the tongue into the airway. The scaffold structure 138 can be variably stiffened in the manner previously described, but need not be.

Figure 48A:
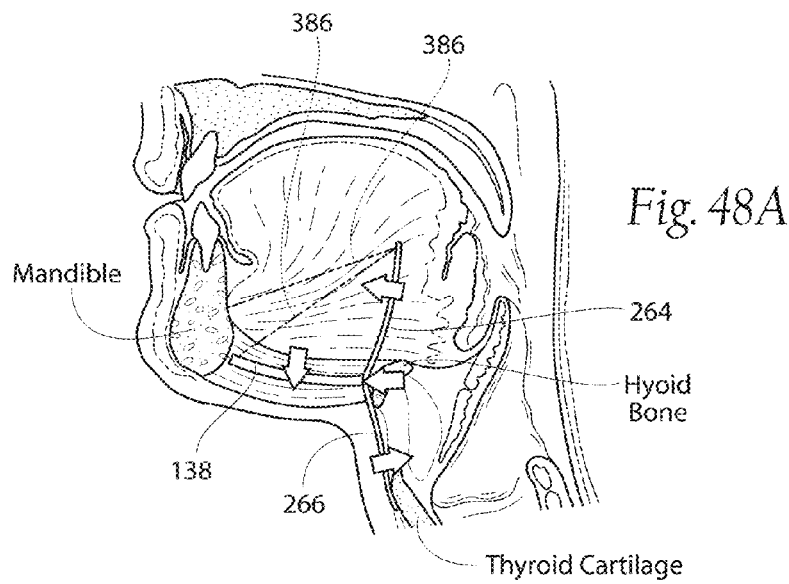
FIG. 48A is an anatomic view of an oral cavity, pharynx, and larynx of an adult human, with the mouth closed, showing a representative embodiment of a system comprising one or more fork-like struts that extend in a superior direction into the tongue to provide tongue stabilization, the struts also extending in an inferior direction to the thyroid cartilage to provide hyoid bone stabilization, the struts also coupled to a scaffold structure implanted in, on, or near the floor of the mouth that is sized and configured to preferentially bend in a caudal direction to provide mechanical support to structures in the floor of the mouth, in combination with tongue stabilization and hyoid bone stabilization.
Figure 48B:
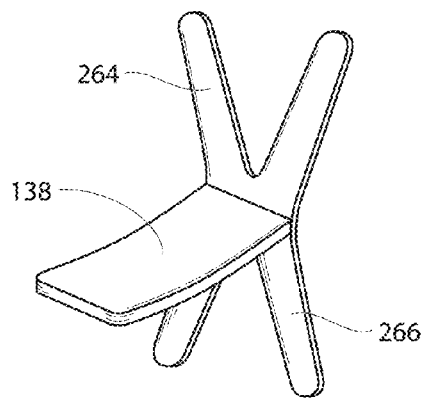
FIG. 48B is a side perspective view of the scaffold structure with superior and inferior fork-like struts shown in side elevation view in FIG. 48A.

FIGS. 48A and 48B show a scaffold structure 138 implanted in an anterior-to-posterior orientation in, on, or near the floor of the mouth. The posterior end of the scaffold structure can be coupled to the hyoid bone in a manner previously described, but it need not be. The scaffold structure 138 can be variably stiffened in the manner previously described, but need not be. The scaffold structure 138 is preferentially biased in a caudal direction, as previously described, or includes one or more components that are actuated by mechanical and/or thermal and/or electrical and/or magnetic energy, in association with an external carrier structure 214 (see, e.g., FIG. 19B), draw the scaffold structure 138 toward the feet, to mechanically support tissue in, on, or near the floor of the mouth in a desired orientation to resist collapse of the airway. The posterior end of the scaffold structure 138 also includes an elastic fork-like strut 264 (also see FIG. 48B) that extends upward into the tongue, to provide tongue stabilization as previously described to resist collapse of the airway, in combination with complementary therapeutic effect of the scaffold structure. The posterior end of the scaffold structure also includes an elastic fork-like strut 266 (also see FIG. 48B) that extends downward anterior to the thyroid cartilage, to provide stabilization and support to the hyoid bone, to resist posterior motion of the hyoid bone, in combination with stabilization of the tongue and the complementary therapeutic effect of the scaffold structure itself. As shown by the arrows in FIG. 48A, the preferential downward bias of the scaffold structure enhances the pulling force on the tongue provided by the superior strut, as well as enhances the anterior support for the hyoid bone provided by the inferior strut. This cooperative combination of forces serves to resists collapse of the airway. As shown in phantom lines in FIG. 48A, the strut 230 can further include an anterior connection member coupled to the mandible and/or anterior end of the scaffold structure. The anterior coupling of the strut to the mandible and/or anterior end of the scaffold structure alters the force vector of the tongue suspension, to create a resulting force vector that has both an anterior component and an inferior component that resists posterior movement of the base of the tongue into the airway.

It should be appreciated that the scaffold structure 138 shown in FIG. 48 can include only the anterior strut 264, or only the superior strut 268 to provide a lesser combination of effects.

Figure 49A:
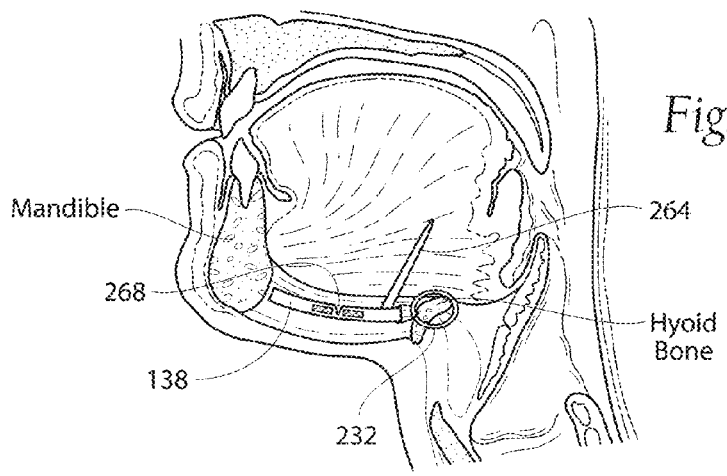
FIG. 49A is an anatomic view of an oral cavity, pharynx, and larynx of an adult human, with the mouth closed, showing a representative embodiment of a system comprising one or more fork-like struts that extend in a superior direction into the tongue to provide tongue stabilization, the struts being coupled to a scaffold structure implanted in, on, or near the floor of the mouth that includes a preformed hinge with adjacent magnets to bend preferentially in a caudal direction.
Figure 49B:
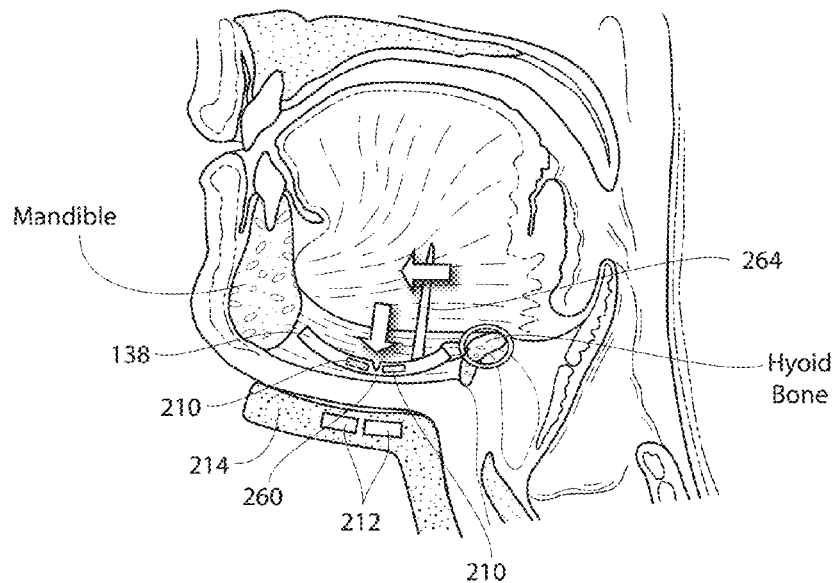
FIG. 49B is view of the system shown in FIG. 49A with an external carrier structure that includes magnets that magnetically interact with the magnets on the scaffold structure to cause the scaffold structure to bend in a caudal direction about the hinge to provide mechanical support to structures in the floor of the mouth, in combination with tongue stabilization.
Figure 49C:
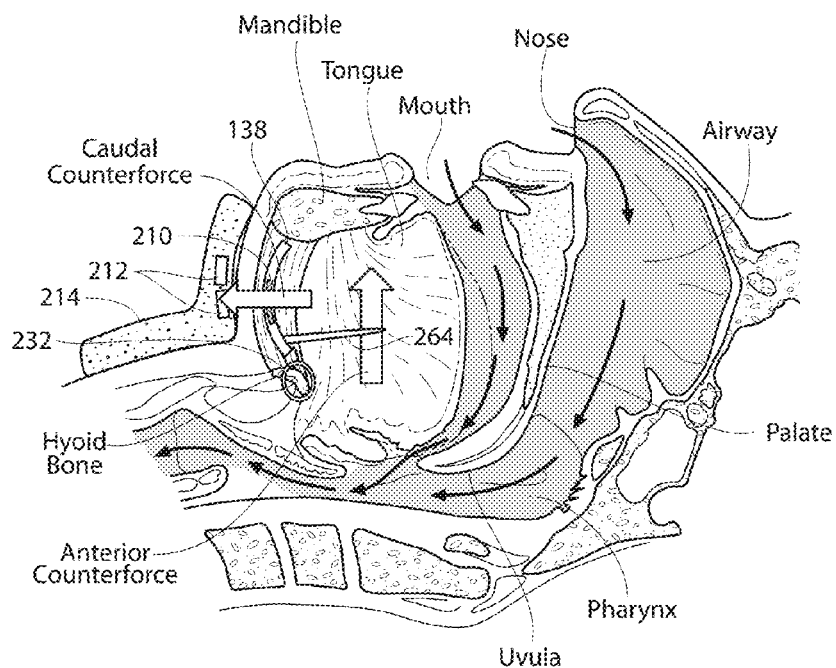
FIG. 49C is an anatomic side section view of an oral cavity, pharynx, and larynx of an adult human, in a supine sleep position with the mouth opened, showing the system shown in FIG. 49B and the magnetic interaction between the magnets on the scaffold structure and the magnets on the external carrier structure to cause the scaffold structure to bend in a caudal direction about the hinge to provide mechanical support to structures in the floor of the mouth, in combination with tongue stabilization.

As shown in FIGS. 49A to 49C, the scaffold structure 138 implanted in, on, or near the floor of the mouth is coupled by one or more rigid rings 230 to the hyoid bone. The scaffold structure 138 includes a superior elastic fork-like strut 264, which extends into the tongue, as also shown in FIGS. 48A and 48B. The scaffold structure 138 further includes a preformed hinge area 268, which can take the form of an area of weakness formed in the structure's material, or a mechanical hinge. The hinge 268 promotes preferential bending in a caudal direction in response to a bending force. In the embodiment shown in FIGS. 49A and 49B, the bending force is applied magnetically. Still, it should be appreciated that the bending force can comprise other forms of energy, e.g., mechanical, electrical, and/or thermal energy, and thereby activated by an external or internal energy source.

More particularly, as shown in FIG. 49A, magnets 210 are carried by the scaffold structure 138 near the hinge 268. An external structure 214 (see FIG. 49B)(and as previously described in connection with FIGS. 19B and 19D) carries external magnets 212. The magnets 210 and 212 are selected to magnetically interact by attracting each another (i.e., they have opposite polarities). When the external structure 214 is worn, the magnetically interaction between the magnets 210 carried by the scaffold structure 138 and the magnets 212 carried by the external structure 214 bends the scaffold structure 138 caudally. As shown by the arrows in FIGS. 39B and 39C, the magnetically induced preferential bending of the scaffold structure 138 in, on, or near the floor of the mouth enhances the pulling force on the tongue provided by the superior strut 264.

The hinged scaffold structure 138 shown in FIG. 49A/B (or any hinged scaffold structure that is sized and configured for implanting in, on, or near the floor of the mouth) can be initially formed to include bioadsorbable components placed in the preformed hinge or area of weakness. The components normally keep the hinge from closing. After implantation, as the bioadsorbable components are progressively absorbed by surrounded tissue, the hinge is, over time, freed and capable of closing in the manner described. As the bioadsorbable components in the spring are progressively absorbed, the preferential bending attributes of the hinged scaffold structure progressively increase to resist buckling of tissue structures in, on, or near the floor of the mouth in a cranial direction.

Figure 50:
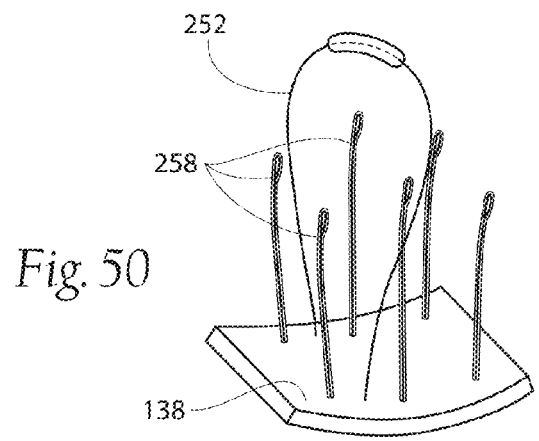
FIG. 50 is a superior perspective view showing a representative embodiment of a system comprising an array of one or more struts that extend in a lateral and anterior-to-posterior direction into the tongue to provide tongue stabilization, the array of struts being coupled to a scaffold structure implanted in, on, or near the floor of the mouth to provide mechanical support to structures in the floor of the mouth, in combination with tongue stabilization, and in which a lasso-like tongue stabilization structure is also coupled to the scaffold structure to provide enhanced tongue stabilization.

As shown in FIG. 50, a scaffold structure 138 implanted in, on, or near the floor of the mouth can also include a lasso-like tongue suspension structure 252 that resists posterior movement of the tongue. The scaffold structure 138 can further include the struts 258 (or 264) as just described (as FIG. 50 shows), for cumulative tongue stabilization effects. Alternatively, a scaffold structure 138 implanted in, on, or near the floor of the mouth without struts can include a lasso-like tongue suspension structure 252. A further representative embodiment incorporating tongue stabilization is shown in FIG. 29 in combination with a system that provides hyoid bone stabilization (anterior).

VI. Further Combinations Hyoid Bone Stabilization/Tongue Stabilization/Floor of the Mouth Implants A. Overview A diverse array of linkage combinations of hyoid bone stabilization (anterior and/or caudal), tongue stabilization (using struts 258/264 or lasso-like structures 252), and scaffold structures 138 implanted in, on, or near the floor of the mouth, to increase, the volume of the oral cavity and otherwise reshape, stiffen, or affect tissue structures can be envisioned.

B. Further Representative Embodiments

For example, an anchor in the genioglossus muscle can be flexibly linked to the floor of the mouth (e.g., to a scaffold structure 138 in the floor of the mouth), to thereby achieve genioglossus advancement/suspension. Hyoid bone stabilization, either anterior or caudal, can be flexibly linked to the floor of the mouth (e.g., to a scaffold structure 138 in the floor of the mouth), or a suspension anchor in the genioglossus muscle can be flexibly linked to a hyoid bone stabilization anterior or caudal system. Mechanisms of stabilization/advancement involving the mandible and/or hyoid bone and/or tongue can be achieved by separate systems, or combined in a single integrated system. Combination systems that include one or more scaffold structures 138 implanted in, on, or near the floor of the mouth make possible a more coordinated "gentle" influence of tissues, rather than a more forceful treatment with only one mechanism of action. For example, a standalone implant in, on, or near the floor of the mouth can be placed along with a standalone genioglossus advancement anchor anchored to bone or connective tissue near bone.

VII. Neuro-Muscular Stimulation in the Floor of the Mouth

Figure 51:
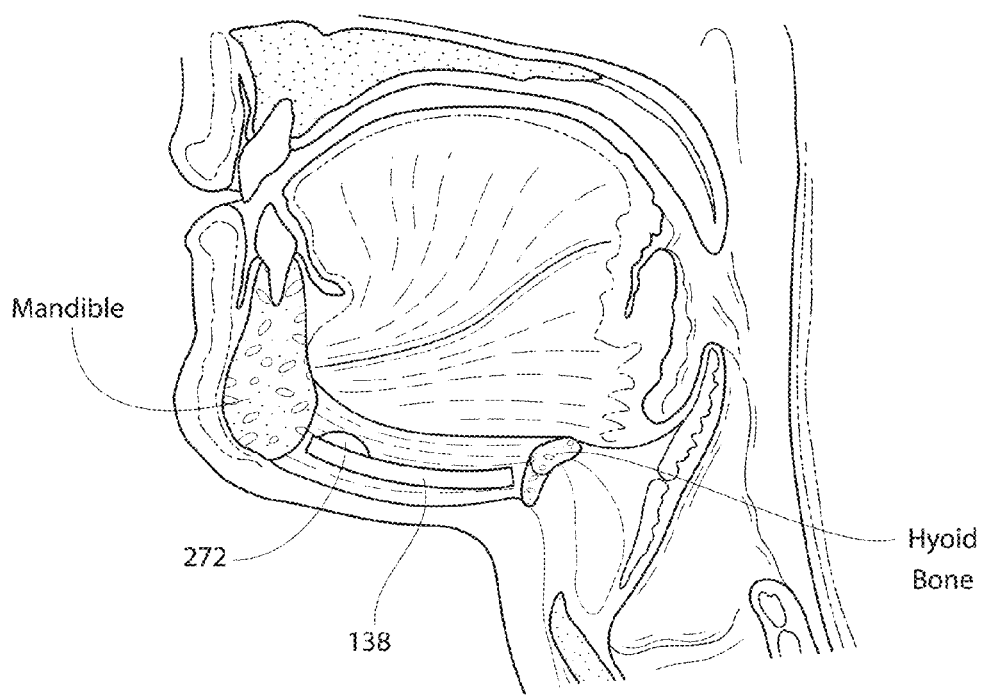
FIG. 51 is a perspective view of a scaffold structure sized and configured to be implanted in, on, or near the floor of the mouth and which further carries an electrical stimulation electrode to affect selective neural-musculature stimulation.

Nerves innervating muscles in, on, or near the floor of the mouth can be electrically stimulated to affect muscle activity and/or to dynamically brace or bias the tissue structures in, on, or near the floor of the mouth against collapse in a cranial direction into the airway, or to apply an anterior lifting force to the back of the tongue, lifting the tongue forward out of the airway. Such stimulation can be performed on a continuous basis when desired, e.g., during sleep, or periodically in response to the detection of a sleep apnea event. A scaffold structure 138 or tissue stiffening device implanted in, on, or near the floor of the mouth can carry an electrical stimulation electrode 272 (see FIG. 51) to affect such stimulation. Likewise, a sensing device(s) 270 can include an electrical stimulation electrode and/or pulse generator to affect such stimulation, either upon command or in response to a sensed condition. Alternatively, or in addition, nerves innervating the genioglossus, e.g., the genioglossus nerve, may be stimulated. The overall stimulation of tissue structures in, on, or near the floor of the mouth can thereby be paced and controlled.

Conventional hypoglossal nerve stimulation devices are implanted far from the hypoglossal nerve in the chest cavity, making implantation of the system and connection of the nerve stimulation lead more invasive, challenging and complicated. A scaffold stricture 138 placed in, on, or near tissue structures in the floor of the mouth can be sized and configured to house the pulse generator and the sensors for hypoglossal nerve stimulation in close proximity to the hypoglossal nerve itself, obviating the need for complex surgical procedures, while also providing the advantages of tissue stabilization, as already described. Positioned in, on, or near tissue structures in the floor of the mouth, a scaffold structure 138 can also includes sensors to sense genioglossis muscle tone changes, to determine the onset of an apneic event. A scaffold structure 138 can also includes sensors to measure oxygen saturation, breathing effort, vibration, and acoustics, to predict the onset of apneic events. A scaffold structure 138 sized and configured for placement in, on, or near tissue structures in the floor of the mouth can also include the pulse generator and the sensors to make possible brain stimulation from a minimally invasive location in the body.

The above-described embodiments of this invention are merely descriptive of its principles and are not to be limited. The scope of this invention instead shall be determined from the scope of the following claims, including their equivalents.

We claim:

1. A stabilization system for resisting posterior movement of a tongue within a mouth into an airway, a floor of the mouth being defined anteriorly by a mandible; posteriorly by a hyoid; and including suprahyoid muscles attached to the mandible and/or hyoid, the tongue resting within the mouth on suprahyoid muscles outside of the floor of the mouth, the system comprising a mount sized and configured to be implanted free of the mandible outside the tongue between suprahyoid muscles in or on the floor of the mouth and/or outside the tongue between an extrinsic muscle of the tongue and a suprahyoid muscle in or on the floor of the mouth, the mount having a posterior region that, when implanted, is sized and configured to be positioned near the hyoid; and one or more struts coupled to the posterior region of the mount, at least one of the one or more struts being sized and configured to extend in a superior direction from the mount into a posterior region of the tongue, the at least one strut comprising mechanical restraining means including a length of extension into the posterior region of the tongue and/or an angular orientation measured in a superior direction from the posterior region of the mount for applying a resisting force to resist posterior movement of the tongue into the airway.

2. A system according to claim 1
wherein the one or more struts comprise an array of struts coupled in an anterior-to-posterior relationship on the mount or in a lateral relationship on the mount or a combination thereof.

3. A system according to claim 1
wherein the mechanical restraining means includes biasing means for urging the posterior region of the tongue toward an anterior position.

4. A system according to claim 3
the biasing means includes an adjustable tensioning mechanism.

5. A system according to claim 3
wherein the biasing means includes a spring.

6. A system according to claim 3
wherein the mechanical retraining means includes a mechanically actuated material, or an electrically actuated material, or a thermally activated material, or a magnetically activated material, or combinations thereof.

7. A system according to claim 1
wherein the mechanical restraining means includes at least one mounting aperture in the posterior region of the mount to receive the at least one strut to couple the at least one strut to the mount.

8. A system according to claim 7
wherein the at least one mounting aperture holds the at least one strut in a desired angular orientation measured in a superior direction from the posterior region of the mount.

9. A system according to claim 8
wherein the at least one mounting aperture includes means for adjusting the desired angular orientation of the at least one strut.

10. A system according to claim 1
wherein the mount has an anterior region that, when implanted, is sized and configured to face the mandible, and an intermediate region that extends between the anterior region and the posterior region of the mount, the intermediate region comprising mechanical supporting means for bracing and resisting inward buckling of suprahyoid muscles in or on the floor of the mouth into the airway during sleep, whereby the mechanical supporting means creates a counter force that directs tissue structures in the mouth out of the airway.

11. A system according to claim 1 wherein the mount comprises a body comprising a material selected from a group comprising metallic material, polymer material, fiber material, or a combination thereof.

12. A system according to claim 11 wherein the body comprises a bio-resorbable structure.

13. A system according to claim 1 wherein the at least one strut comprises a material selected from a group comprising metallic material, polymer material, fiber material, or a combination thereof.

14. A system according to claim 13 wherein the at least one strut comprises a surface treated to limit fibrotic encapsulation.

* * * * *